US012558292B2

(12) United States Patent
Morinaga et al.

(10) Patent No.: US 12,558,292 B2
(45) Date of Patent: Feb. 24, 2026

(54) MEDICATION SUPPORT APPARATUS AND MEDICATION SUPPORT SYSTEM

(71) Applicants: Takuya Morinaga, Tokyo (JP);
Hirotaka Hayashi, Kanagawa (JP);
Akira Kojima, Kanagawa (JP); Hiroshi
Fujie, Kanagawa (JP); Wataru Nozaki,
Kanagawa (JP)

(72) Inventors: Takuya Morinaga, Tokyo (JP);
Hirotaka Hayashi, Kanagawa (JP);
Akira Kojima, Kanagawa (JP); Hiroshi
Fujie, Kanagawa (JP); Wataru Nozaki,
Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 729 days.

(21) Appl. No.: 17/950,427

(22) Filed: Sep. 22, 2022

(65) Prior Publication Data

US 2023/0096511 A1     Mar. 30, 2023

(30) Foreign Application Priority Data

Sep. 30, 2021     (JP) ................................. 2021-161972

(51) Int. Cl.
*A61J 7/00*          (2006.01)
*G07F 11/62*         (2006.01)
(Continued)

(52) U.S. Cl.
CPC ............ *A61J 7/0084* (2013.01); *G16H 20/13* (2018.01); *G07F 11/62* (2013.01); *G07F 17/0092* (2013.01)

(58) Field of Classification Search
CPC .... G07F 17/0092; G07F 11/165; G07F 11/18; G07F 11/62; G16H 20/13; A61J 7/0069;
(Continued)

(56) References Cited

U.S. PATENT DOCUMENTS 7,123,989 B2 * 10/2006 Pinney ................... G07F 9/026
                                                    700/216
11,510,850 B2 * 11/2022 Hayashi ................ A61J 7/0076
                    (Continued)

FOREIGN PATENT DOCUMENTS

JP          2017-000177 A       1/2017
JP          2017-153646         9/2017
                    (Continued)

OTHER PUBLICATIONS

Japanese Office Action dated Apr. 15, 2025 issued in corresponding Japanese Patent Appln. No. 2021-161972.

*Primary Examiner* — Timothy R Waggoner
(74) *Attorney, Agent, or Firm* — Harness, Dickey & Pierce, P.L.C.

(57)                    ABSTRACT

A medication support apparatus includes a storage, a medicine delivery part, an extraction device, a transfer device, a pack information reader, and processing circuitry. The storage stores a medicine pack with first medication-related information. The medicine pack is arranged at a specific position in the delivery part. The extraction device extracts the medicine pack from the storage. The transfer device transfers the medicine pack extracted from the storage to the specific position in the delivery part. The pack information reader reads the first medication-related information before the transfer device transfers the medicine pack extracted from the storage to the specific position in the delivery part. The processing circuitry manages second medication-related information of the medicine pack, and compares the first medication-related information read by the pack information reader with the second medication-related information to determine whether medication-related information matches between the first medication-related information and the second medication-related information.

20 Claims, 39 Drawing Sheets

(51) Int. Cl.
  *G07F 17/00* (2006.01)
  *G16H 20/13* (2018.01)

(58) Field of Classification Search
  CPC ...... A61J 7/0463; A61J 1/035; A61J 2205/60;
                      A61J 2200/70; A61J 7/0084
  See application file for complete search history.

(56) References Cited

U.S. PATENT DOCUMENTS

| | | | |
|---|---|---|---|
| 2005/0049746 A1* | 3/2005 | Rosenblum ............ | G16H 20/13 |
| | | | 700/232 |
| 2016/0259914 A1* | 9/2016 | Iantorno ................ | G16H 20/13 |
| 2021/0361532 A1 | 11/2021 | Hayashi et al. | |
| 2022/0157426 A1 | 5/2022 | Fujie et al. | |
| 2022/0233406 A1 | 7/2022 | Kojima et al. | |

FOREIGN PATENT DOCUMENTS

| | | |
|---|---|---|
| JP | 2017-192455 | 10/2017 |
| JP | 2018-050936 A | 4/2018 |
| JP | 2018-175297 A | 11/2018 |
| JP | 2020-116273 | 8/2020 |

* cited by examiner

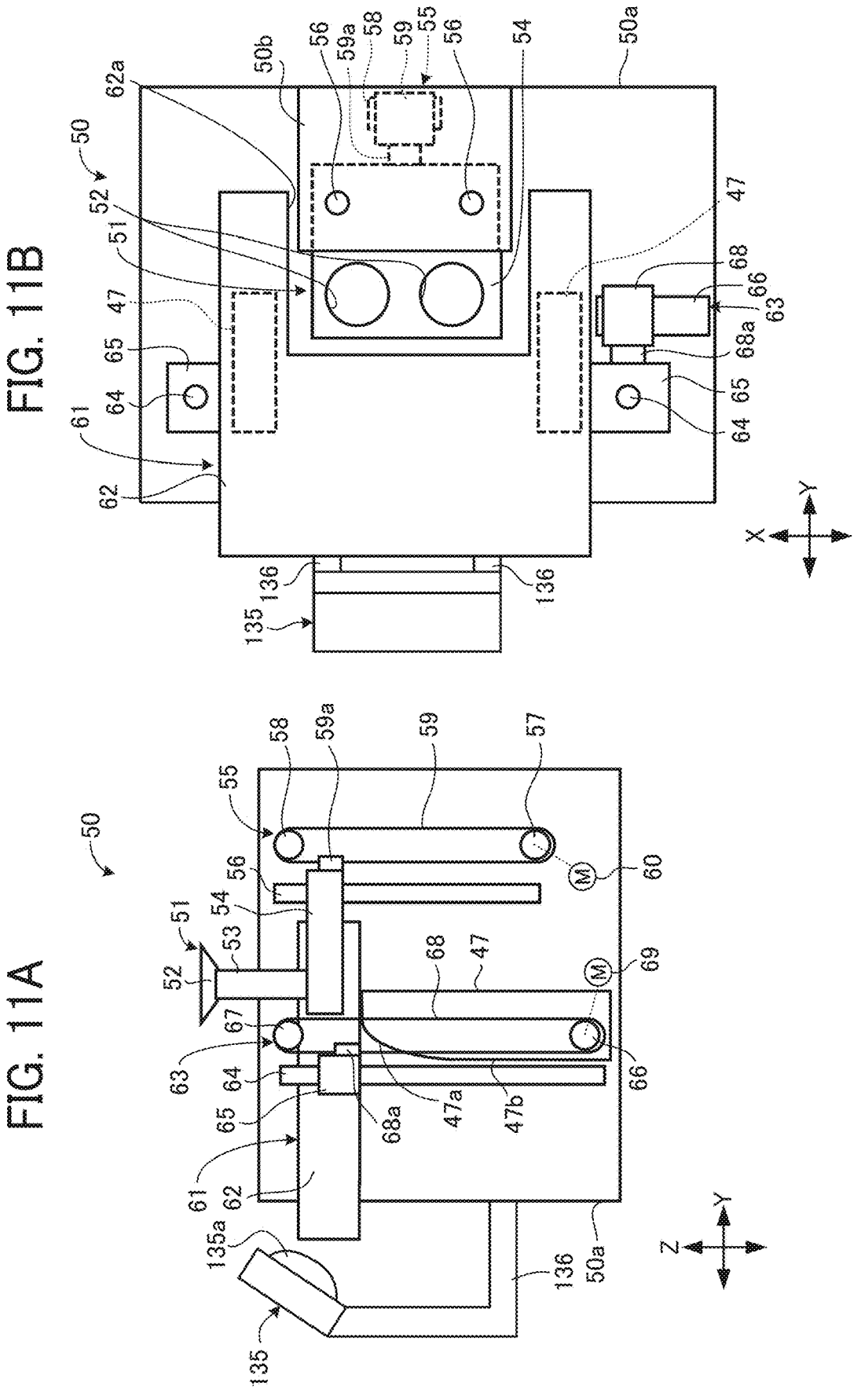

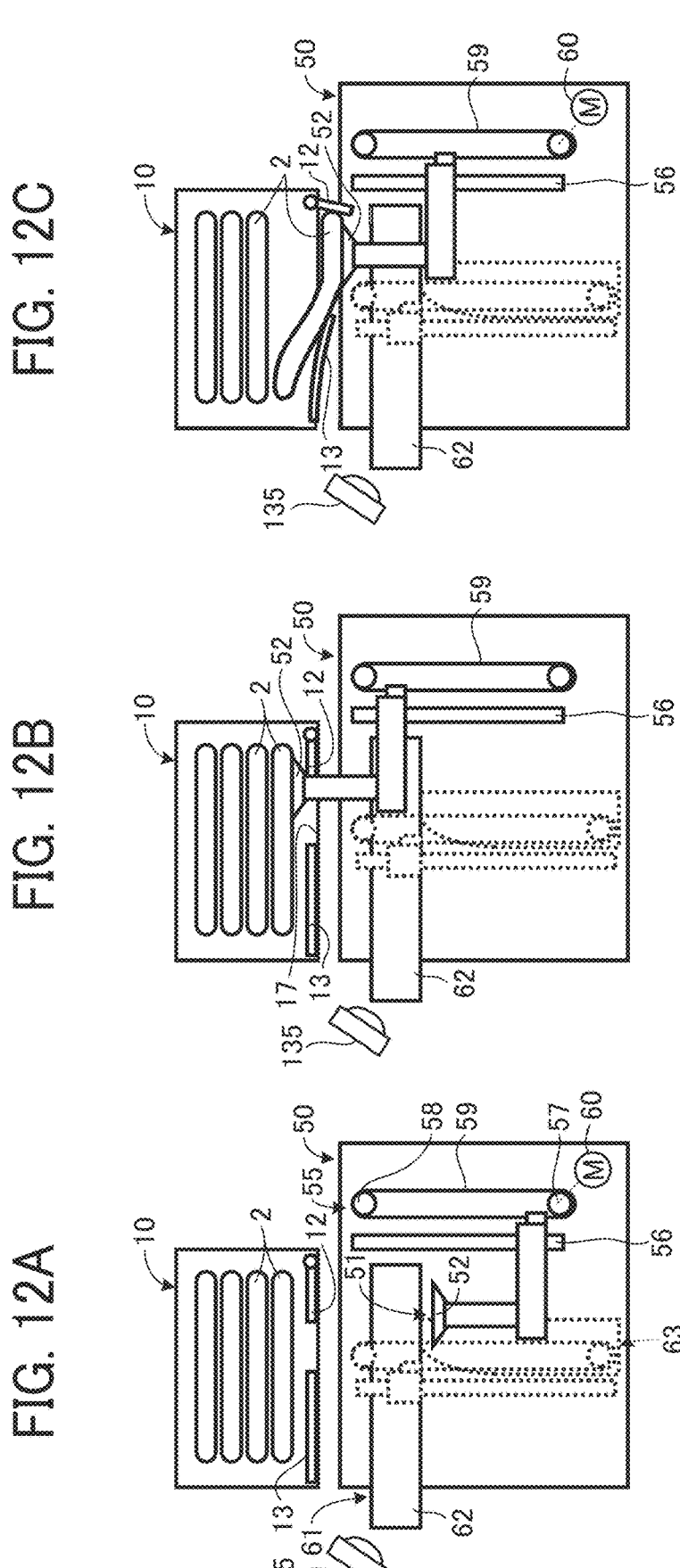

FIG. 12F
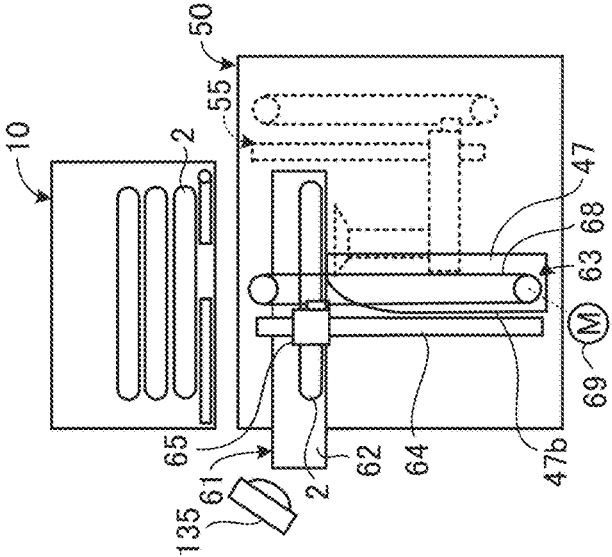
FIG. 12E
FIG. 12D
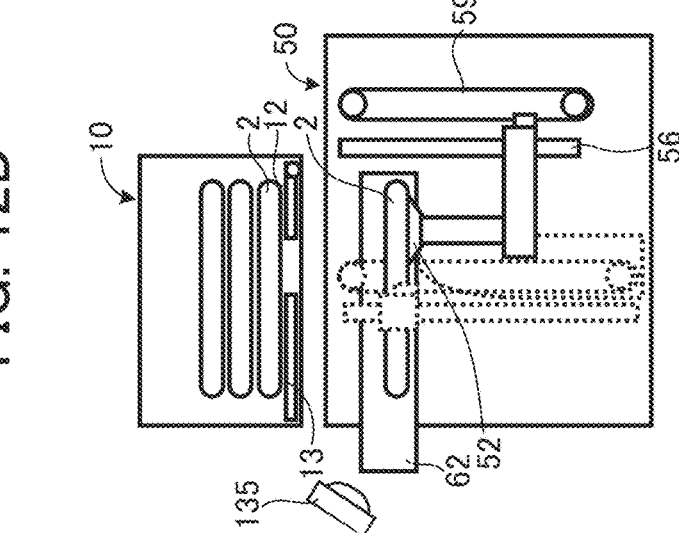

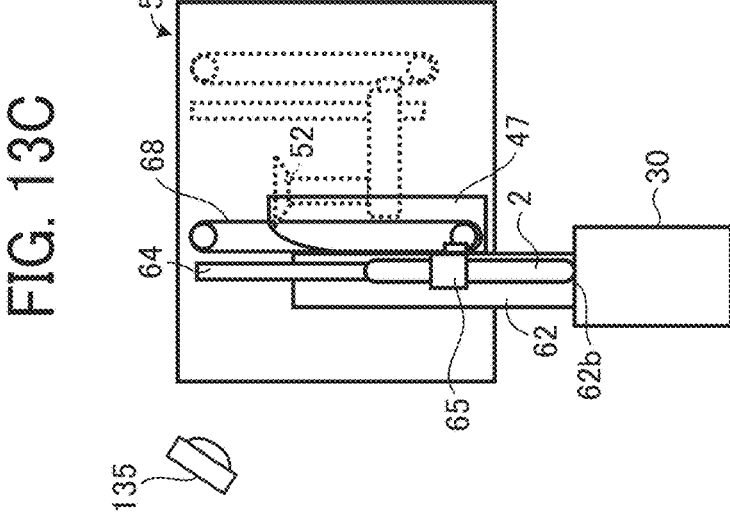

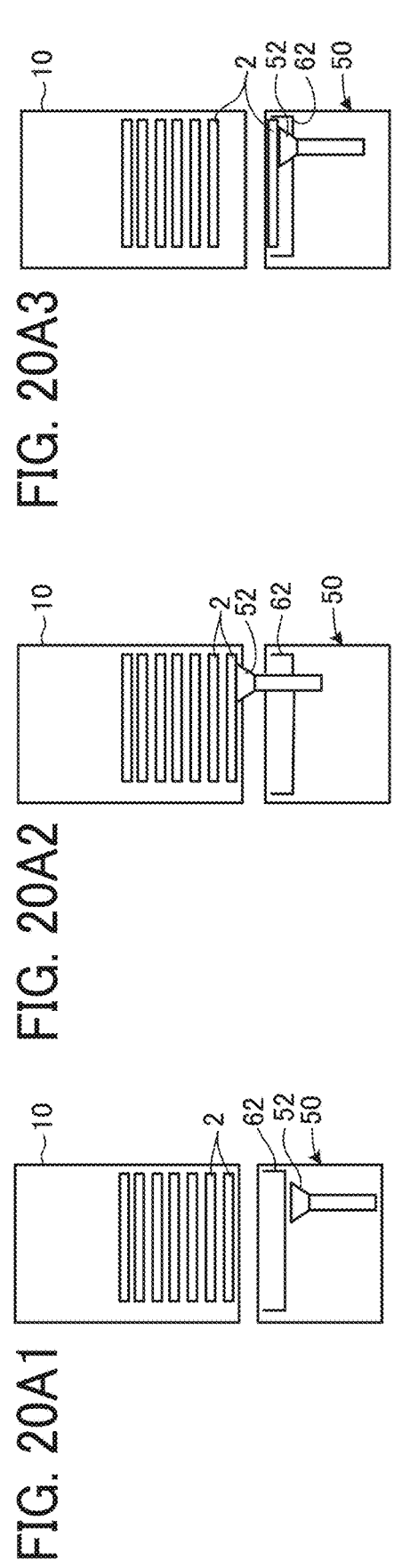
FIG. 20A1
FIG. 20A2
FIG. 20A3
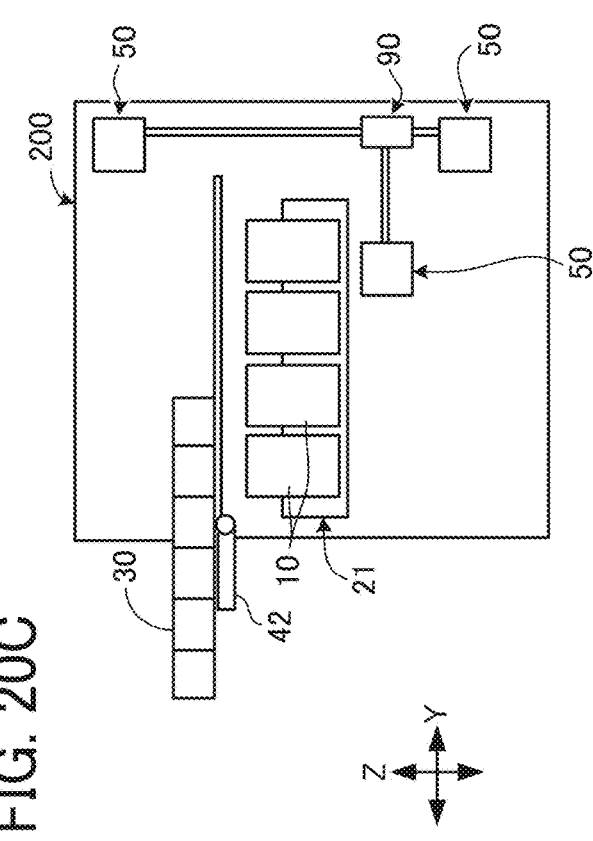
FIG. 20C
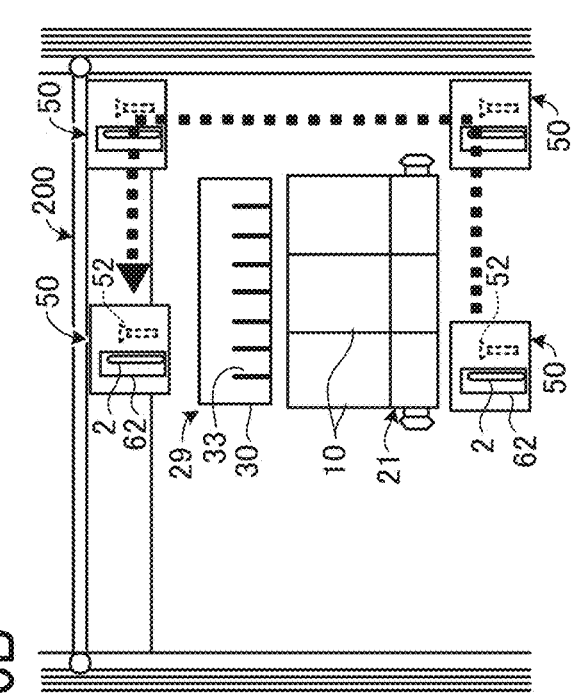
FIG. 20B

Figure 25:
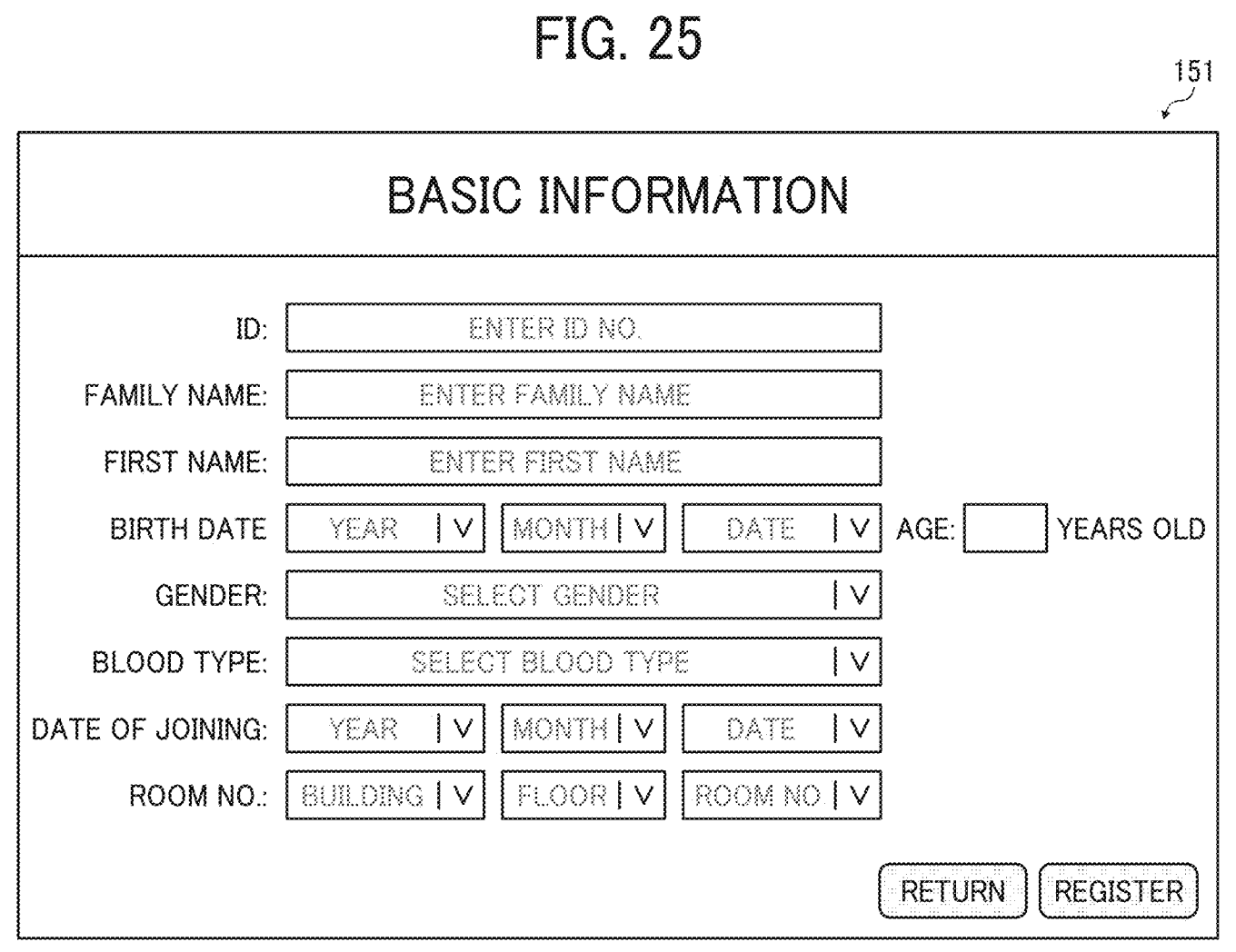

BASIC INFORMATION

| ID: | ENTER ID NO. |
| FAMILY NAME: | ENTER FAMILY NAME |
| FIRST NAME: | ENTER FIRST NAME |
| BIRTH DATE | YEAR |∨ | MONTH |∨ | DATE |∨ | AGE: [ ] YEARS OLD |
| GENDER: | SELECT GENDER |∨ |
| BLOOD TYPE: | SELECT BLOOD TYPE |∨ |
| DATE OF JOINING: | YEAR |∨ | MONTH |∨ | DATE |∨ |
| ROOM NO.: | BUILDING |∨ | FLOOR |∨ | ROOM NO |∨ |

RETURN    REGISTER

FIG. 26

MEDICATION INFORMATION

151

| PACK NO ① | PACK NO ② | PACK NO ③ | PACK NO ④ | PACK NO ⑤ |

NAME: MR. A    ROOM NO.:A-1F-101

| No. | MEDI-CINE | QUANTITY | TYPE |
|-----|-----------|----------|------|
| 1 | MEDI-CINE A | 2 [PIECE(S)] | TABLET ∨ |
| 2 | MEDI-CINE B | 1 [CAPSULE] | CAPSULE ∨ |
| 3 | | | |
| 4 | | | |
| 5 | | | |
| 6 | | | |

< ▨ >

NO. OF PACKS: SELECT NO. OF PACK(S) ∨

STORAGE NO.: SELECT CARTRIDGE NO. ∨

MEDICATION TIMING: SELECT TIMING ∨

STORAGE    DRAWER NO. [ ]    VERTICAL NO. [ ]    HORIZON-TAL NO. [ ]

MEDICINE DELIVERY TRAY    TRAY NO. [ ]    VERTICAL NO. [ ]    HORIZON-TAL NO. [ ]

RETURN    REGISTER

FIG. 28

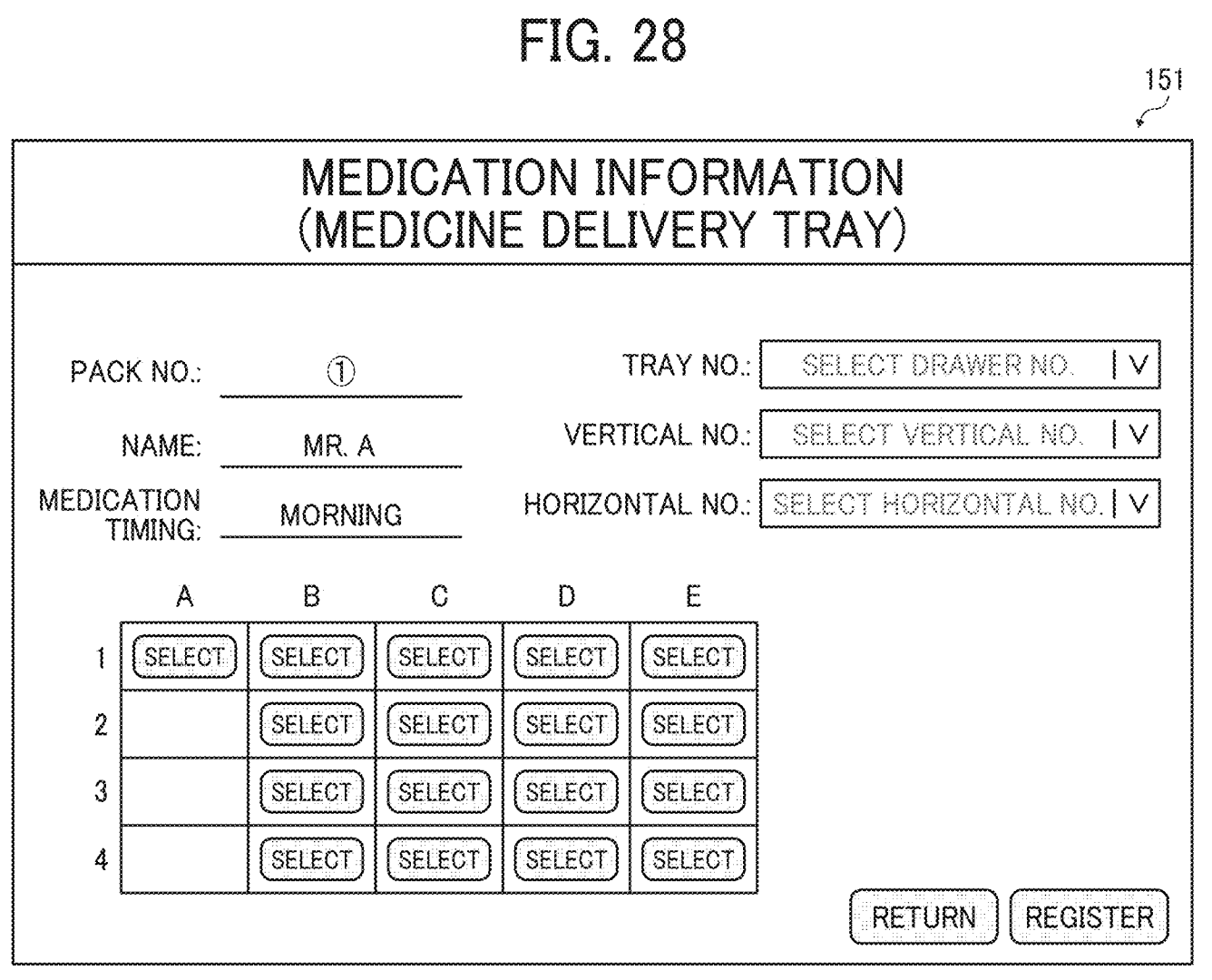

MEDICATION INFORMATION
(MEDICINE DELIVERY TRAY)

PACK NO.:        ①

NAME:        MR. A

MEDICATION
TIMING:        MORNING

TRAY NO.:        SELECT DRAWER NO.    |∨

VERTICAL NO.:        SELECT VERTICAL NO.    |∨

HORIZONTAL NO.:        SELECT HORIZONTAL NO. |∨

|   | A | B | C | D | E |
|---|---|---|---|---|---|
| 1 | SELECT | SELECT | SELECT | SELECT | SELECT |
| 2 |  | SELECT | SELECT | SELECT | SELECT |
| 3 |  | SELECT | SELECT | SELECT | SELECT |
| 4 |  | SELECT | SELECT | SELECT | SELECT |

RETURN        REGISTER

Figure 29:
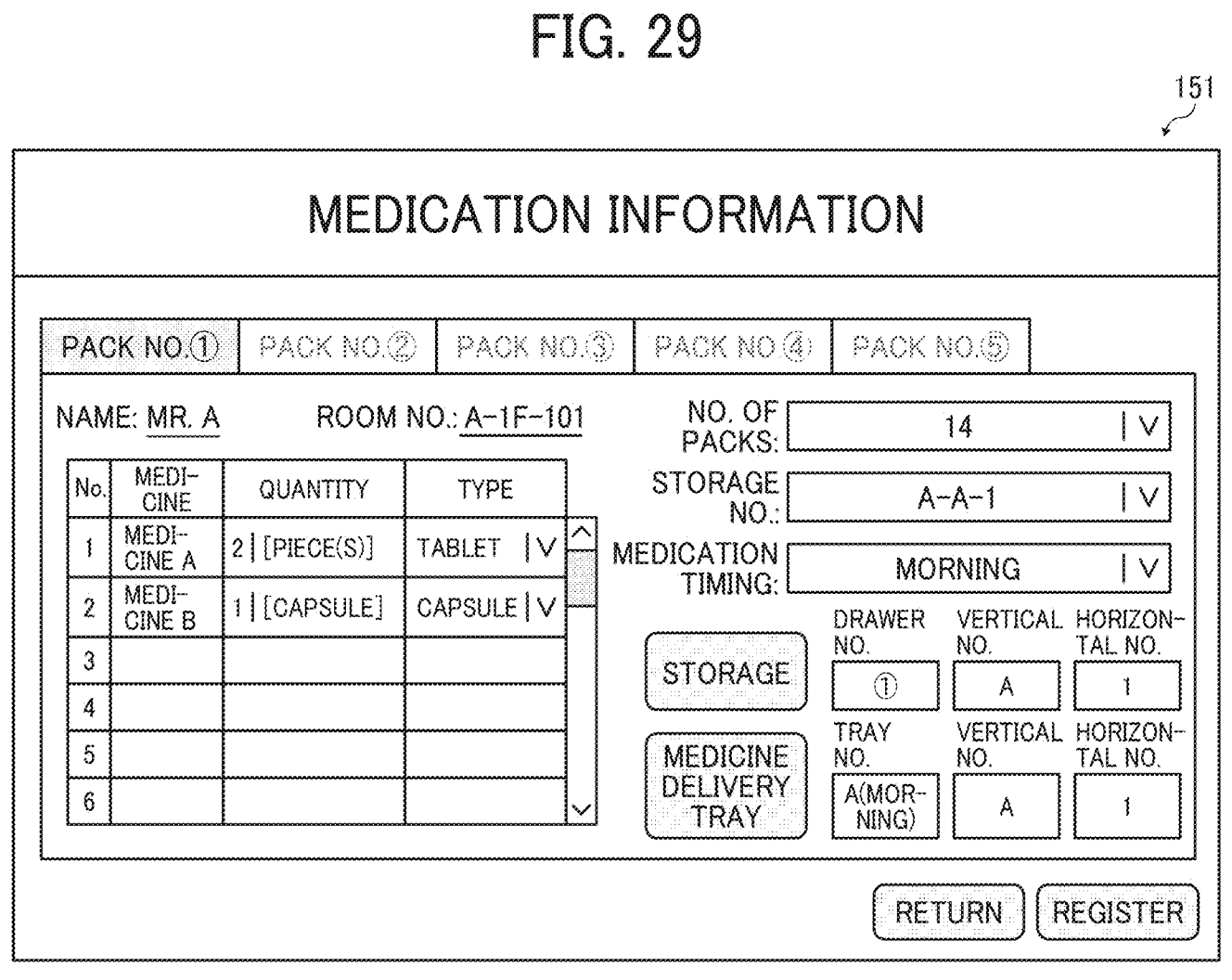

MEDICATION INFORMATION

| PACK NO.① | PACK NO.② | PACK NO.③ | PACK NO.④ | PACK NO.⑤ |
|---|---|---|---|---|

NAME: MR. A    ROOM NO.: A-1F-101

| No. | MEDI-CINE | QUANTITY | TYPE |
|---|---|---|---|
| 1 | MEDI-CINE A | 2 [PIECE(S)] | TABLET ∨ |
| 2 | MEDI-CINE B | 1 [CAPSULE] | CAPSULE ∨ |
| 3 | | | |
| 4 | | | |
| 5 | | | |
| 6 | | | |

‹ ›

NO. OF PACKS: 14 ∨

STORAGE NO.: A-A-1 ∨

MEDICATION TIMING: MORNING ∨

| | DRAWER NO. | VERTICAL NO. | HORIZON-TAL NO. |
|---|---|---|---|
| STORAGE | ① | A | 1 |

| | TRAY NO. | VERTICAL NO. | HORIZON-TAL NO. |
|---|---|---|---|
| MEDICINE DELIVERY TRAY | A(MOR-NING) | A | 1 |

RETURN    REGISTER

FIG. 30

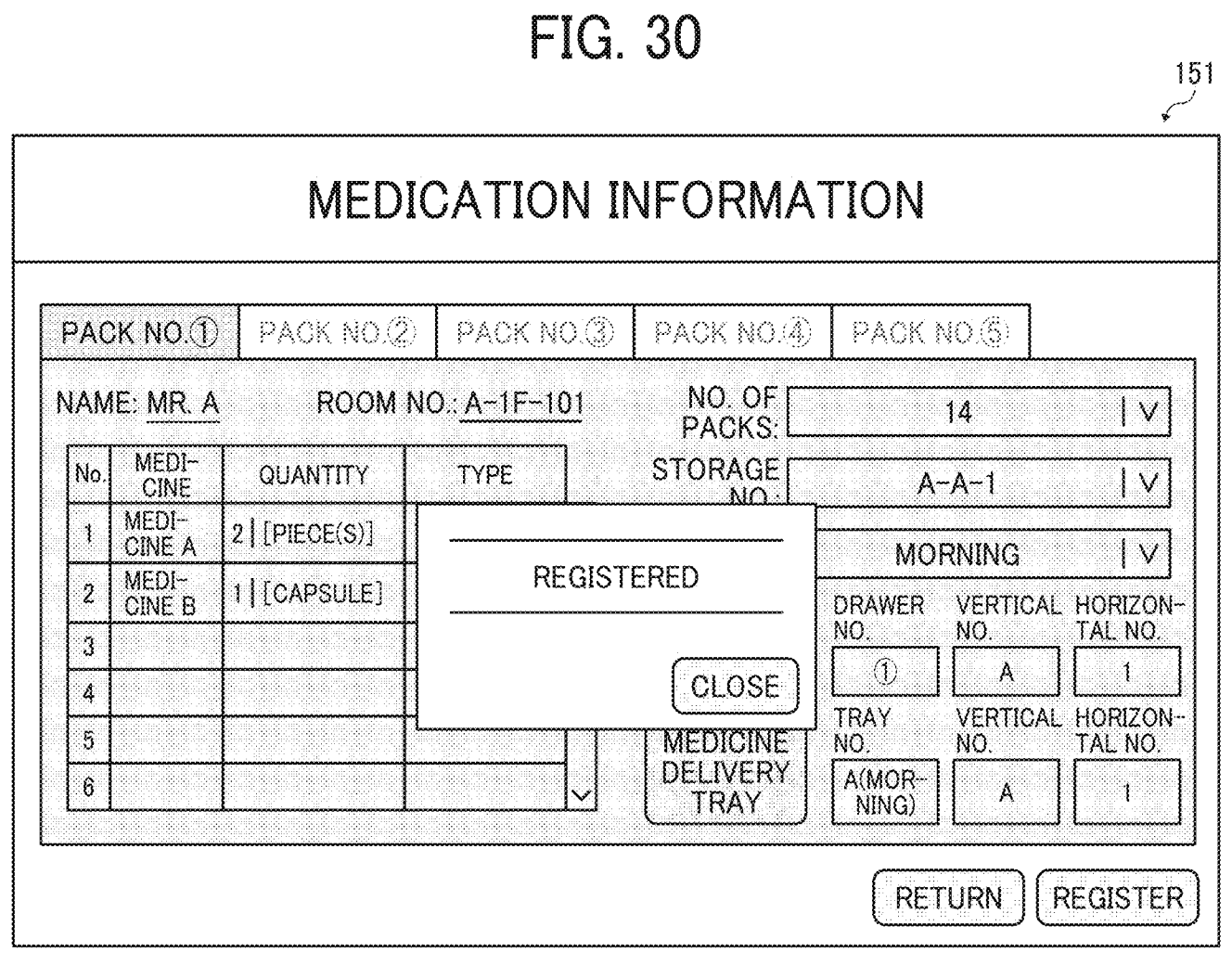

MEDICATION INFORMATION

151

| PACK NO.① | PACK NO.② | PACK NO.③ | PACK NO.④ | PACK NO.⑤ | PACK NO.⑥ |
|---|---|---|---|---|---|

NAME: MR. A    ROOM NO.: A-1F-101    NO. OF PACKS: 14   |∨|

| No. | MEDI-CINE | QUANTITY | TYPE |
|---|---|---|---|
| 1 | MEDI-CINE A | 2 [PIECE(S)] | |
| 2 | MEDI-CINE B | 1 [CAPSULE] | |
| 3 | | | |
| 4 | | | |
| 5 | | | |
| 6 | | | |

STORAGE NO.: A-A-1   |∨|

REGISTERED

CLOSE

MORNING   |∨|

| DRAWER NO. | VERTICAL NO. | HORIZON-TAL NO. |
|---|---|---|
| ① | A | 1 |

| TRAY NO. | VERTICAL NO. | HORIZON-TAL NO. |
|---|---|---|
| A(MOR-NING) | A | 1 |

MEDICINE DELIVERY TRAY

RETURN    REGISTER

FIG. 31

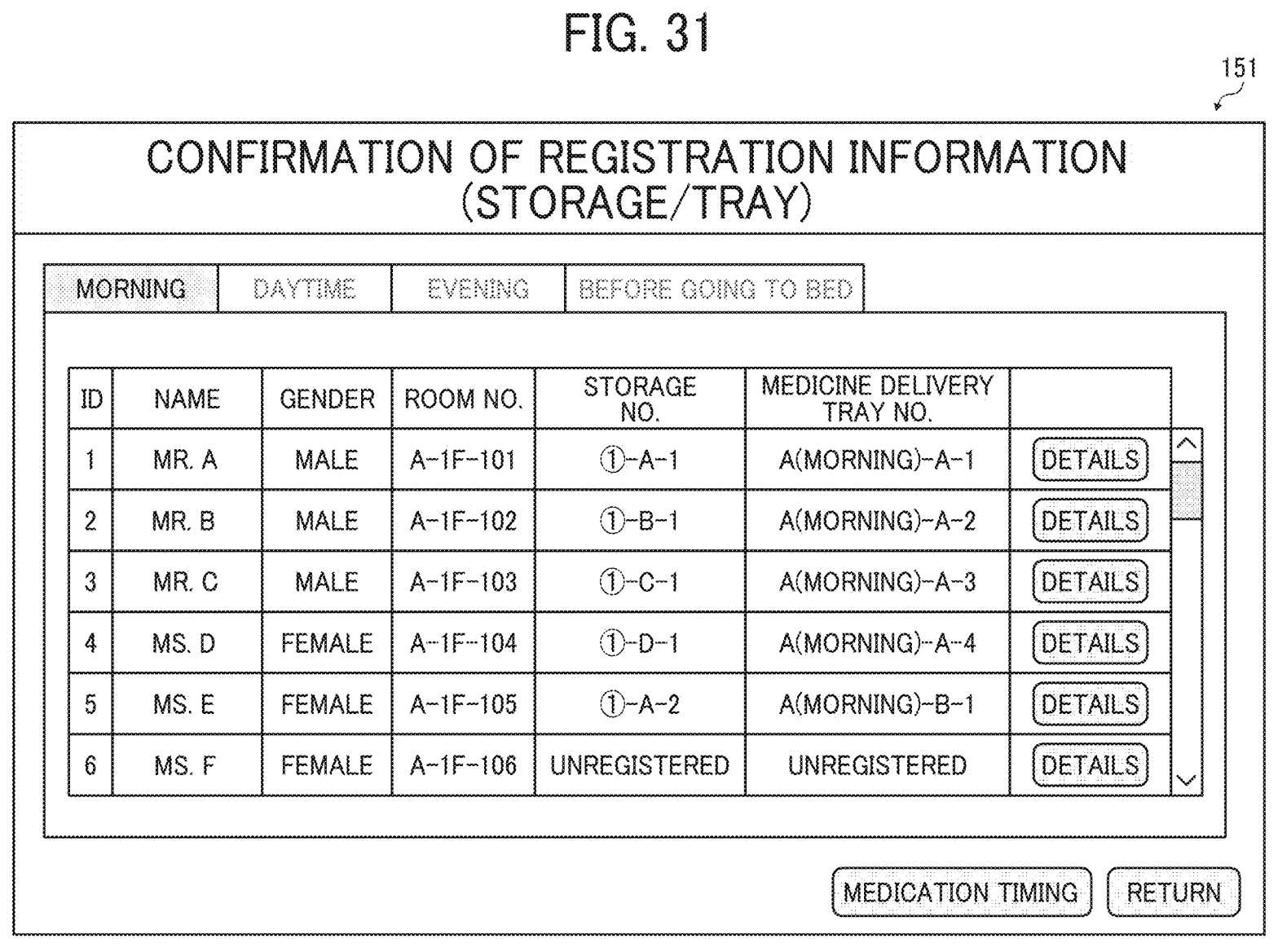

CONFIRMATION OF REGISTRATION INFORMATION (STORAGE/TRAY)

151

| MORNING | DAYTIME | EVENING | BEFORE GOING TO BED |

| ID | NAME | GENDER | ROOM NO. | STORAGE NO. | MEDICINE DELIVERY TRAY NO. | |
|---|---|---|---|---|---|---|
| 1 | MR. A | MALE | A-1F-101 | ①-A-1 | A(MORNING)-A-1 | DETAILS |
| 2 | MR. B | MALE | A-1F-102 | ①-B-1 | A(MORNING)-A-2 | DETAILS |
| 3 | MR. C | MALE | A-1F-103 | ①-C-1 | A(MORNING)-A-3 | DETAILS |
| 4 | MS. D | FEMALE | A-1F-104 | ①-D-1 | A(MORNING)-A-4 | DETAILS |
| 5 | MS. E | FEMALE | A-1F-105 | ①-A-2 | A(MORNING)-B-1 | DETAILS |
| 6 | MS. F | FEMALE | A-1F-106 | UNREGISTERED | UNREGISTERED | DETAILS |

MEDICATION TIMING    RETURN

FIG. 32

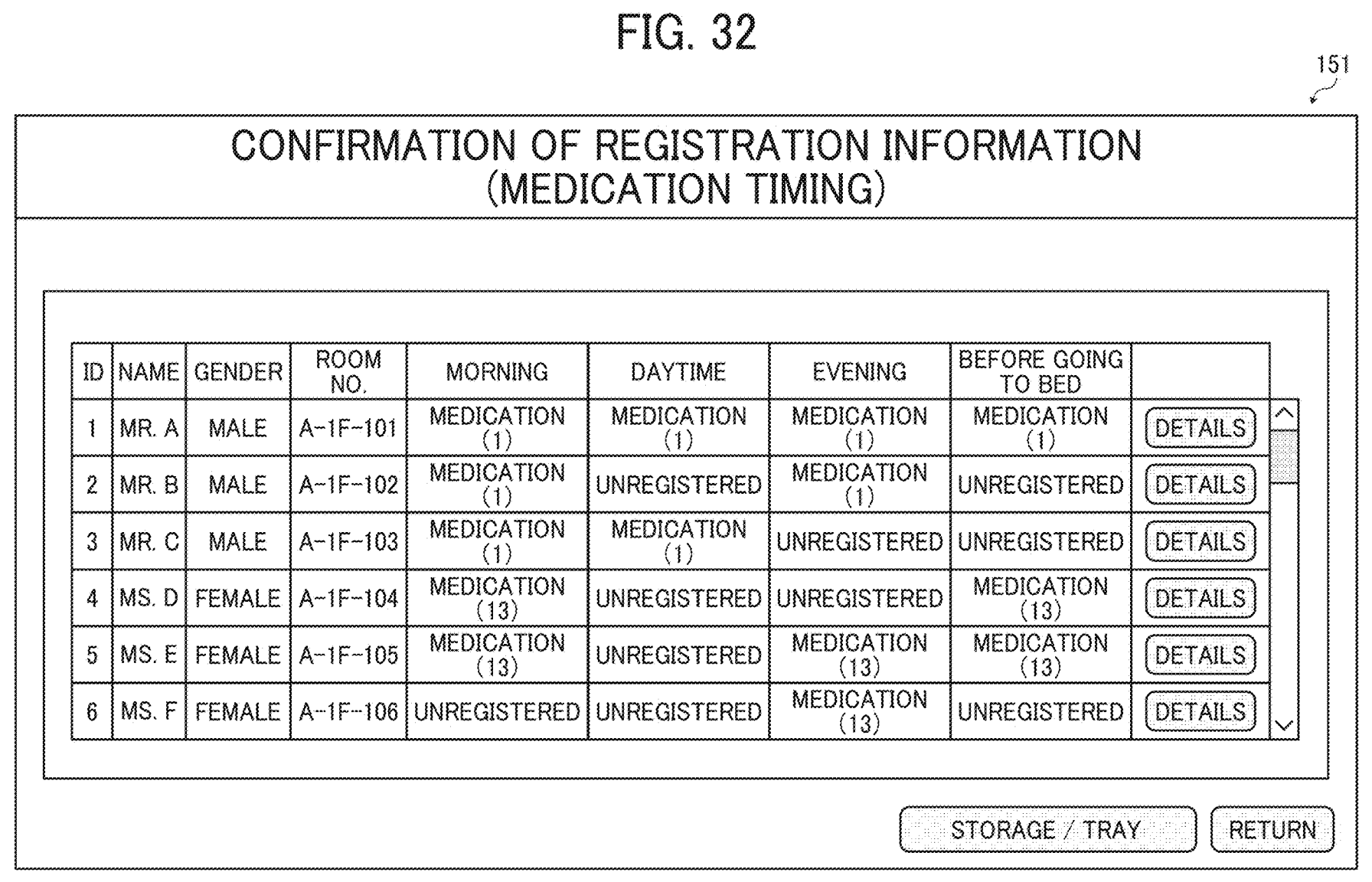

CONFIRMATION OF REGISTRATION INFORMATION
(MEDICATION TIMING)

| ID | NAME | GENDER | ROOM NO. | MORNING | DAYTIME | EVENING | BEFORE GOING TO BED | |
|----|------|--------|----------|---------|---------|---------|---------------------|---|
| 1 | MR. A | MALE | A-1F-101 | MEDICATION (1) | MEDICATION (1) | MEDICATION (1) | MEDICATION (1) | DETAILS |
| 2 | MR. B | MALE | A-1F-102 | MEDICATION (1) | UNREGISTERED | MEDICATION (1) | UNREGISTERED | DETAILS |
| 3 | MR. C | MALE | A-1F-103 | MEDICATION (1) | MEDICATION (1) | UNREGISTERED | UNREGISTERED | DETAILS |
| 4 | MS. D | FEMALE | A-1F-104 | MEDICATION (13) | UNREGISTERED | UNREGISTERED | MEDICATION (13) | DETAILS |
| 5 | MS. E | FEMALE | A-1F-105 | MEDICATION (13) | UNREGISTERED | MEDICATION (13) | MEDICATION (13) | DETAILS |
| 6 | MS. F | FEMALE | A-1F-106 | UNREGISTERED | UNREGISTERED | MEDICATION (13) | UNREGISTERED | DETAILS |

STORAGE / TRAY

RETURN

Figure 33:
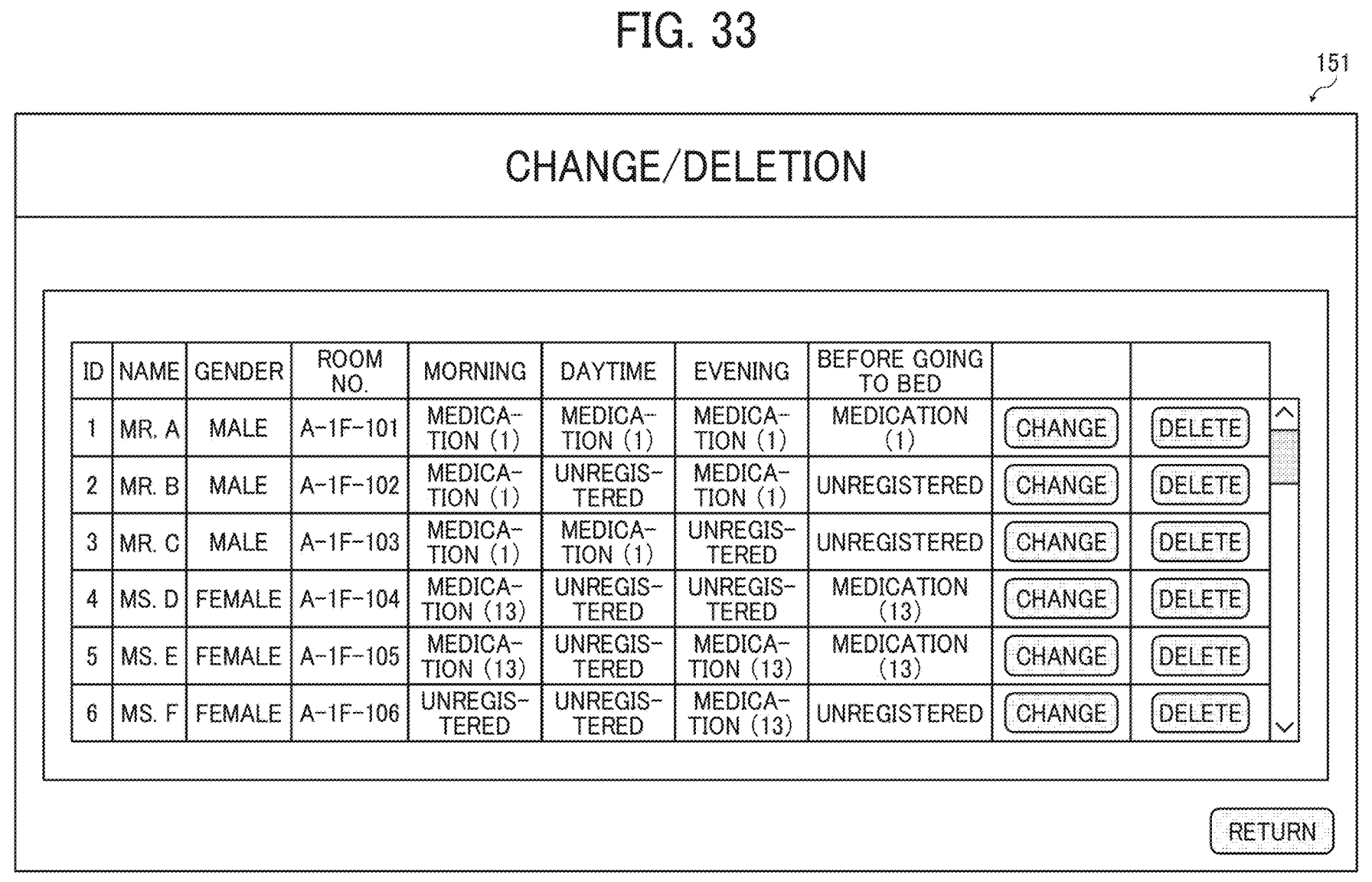

CHANGE/DELETION

| ID | NAME | GENDER | ROOM NO. | MORNING | DAYTIME | EVENING | BEFORE GOING TO BED | | |
|----|------|--------|----------|---------|---------|---------|---------------------|--|--|
| 1 | MR. A | MALE | A-1F-101 | MEDICA-TION (1) | MEDICA-TION (1) | MEDICA-TION (1) | MEDICATION (1) | CHANGE | DELETE |
| 2 | MR. B | MALE | A-1F-102 | MEDICA-TION (1) | UNREGIS-TERED | MEDICA-TION (1) | UNREGISTERED | CHANGE | DELETE |
| 3 | MR. C | MALE | A-1F-103 | MEDICA-TION (1) | MEDICA-TION (1) | UNREGIS-TERED | UNREGISTERED | CHANGE | DELETE |
| 4 | MS. D | FEMALE | A-1F-104 | MEDICA-TION (13) | UNREGIS-TERED | UNREGIS-TERED | MEDICATION (13) | CHANGE | DELETE |
| 5 | MS. E | FEMALE | A-1F-105 | MEDICA-TION (13) | UNREGIS-TERED | MEDICA-TION (13) | MEDICATION (13) | CHANGE | DELETE |
| 6 | MS. F | FEMALE | A-1F-106 | UNREGIS-TERED | UNREGIS-TERED | MEDICA-TION (13) | UNREGISTERED | CHANGE | DELETE |

RETURN

| MACHINE STATUS | | |
|---|---|---|

MACHINE STATUS  [ ERROR INFORMATION ]

| No. | OCCURRENCE  TIME | ERROR DESCRIPTION |
|---|---|---|
| 1 | 2020/05/15  07:33 | WRONG PACK DETECTED (①-A-2) |
| 2 | 2020/03/02  21:04 | WRONG PACK DETECTED (③-D-1) |
| 3 | 2020/02/10  16:57 | FAILED DELIVERY (C(EVENING)-B-3) |
| 4 | 2019/12/14  13:01 | FAILED DELIVERY (B(DAYTIME)-A-1) |
| 5 | 2019/10/22  02:41 | WRONG PACK DETECTED (②-B-1) |
| 6 | 2019/07/31  16:29 | FAILED DELIVERY (C(EVENING)-A-6) |
| 7 | 2019/07/01  08:17 | FAILED DELIVERY (A(MORNING)-B-2) |

FIG. 36A          FIG. 36 | FIG. 36A | FIG. 36B
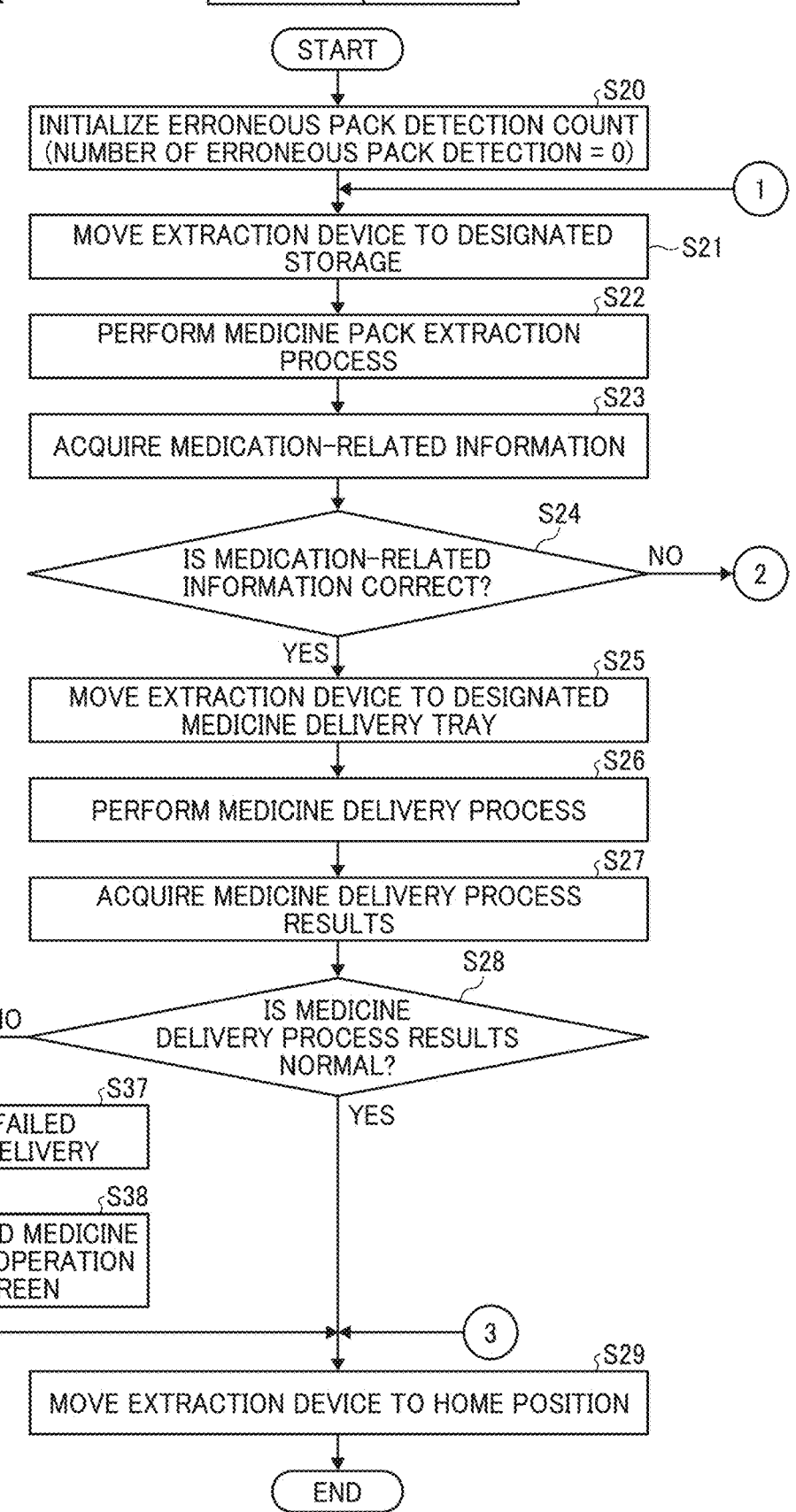

FIG. 37B

FOR MR. A AT
BREAKFAST TIME

MEDICATION SUPPORT APPARATUS AND MEDICATION SUPPORT SYSTEM

CROSS-REFERENCE TO RELATED APPLICATION

This patent application is based on and claims priority pursuant to 35 U.S.C. § 119(a) to Japanese Patent Application No. 2021-161972, filed on Sep. 30, 2021, in the Japan Patent Office, the entire disclosure of which is hereby incorporated by reference herein.

BACKGROUND

Technical Field

Embodiments of the present disclosure relate to a medication support apparatus and a medication support system.

Related Art

For the purpose of reducing the trouble of medication of a medicine recipient or a caregiver of the medicine recipient, there is known a technique of notifying a user of a medicine set in advance in a storage for each dosage opportunity and providing the medicine at a predetermined dosage time.

SUMMARY

According to an embodiment of the present disclosure, a medication support apparatus includes a storage, a medicine delivery part, an extraction device, a transfer device, a pack information reader, and processing circuitry. The storage stores a medicine pack with first medication-related information. The medicine pack includes medicine. The medicine pack is to be arranged at a specific position in the medicine delivery part. The extraction device extracts the medicine pack from the storage. The transfer device transfers the medicine pack extracted from the storage to the specific position in the medicine delivery part. The pack information reader reads the first medication-related information before the transfer device transfers the medicine pack extracted from the storage to the specific position in the medicine delivery part. The processing circuitry manages second medication-related information of the medicine pack to be arranged at the specific position in the medicine delivery part, and compares the first medication-related information read by the pack information reader with the second medication-related information to determine whether medication-related information matches between the first medication-related information and the second medication-related information.

According to another embodiment of the present disclosure, a medication support system includes the medication support apparatus, an information communication terminal owned by a system user, and an information communication device. The information communication device performs communication between the medication support apparatus and the information communication terminal via a network. The processing circuitry causes the information communication device to transmit at least one of detection information indicating that the medicine pack extracted from the storage is a wrong pack or information indicating that medicine delivery processing of the medicine pack to the medicine delivery part has failed, to the information communication terminal.

2

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 1A is a front view of an entire medication support apparatus according to an embodiment of the present disclosure;

FIG. 1B is a side view of the medication support apparatus illustrated in FIG. 1A;

FIG. 3 is an external perspective view illustrating a configuration example of a medicine delivery tray;

FIG. 11A is a front view illustrating a configuration of an extraction device;

FIG. 11B is a plan view of the configuration of the extraction device illustrated in FIG. 11A;

FIG. 12A is a front view illustrating an operation of the extraction device;

FIG. 12B is a front view illustrating an operation of the extraction device performed subsequent to FIG. 12A;

FIG. 12C is a front view illustrating an operation of the extraction device performed subsequent to FIG. 12B;

FIG. 12D is a front view illustrating an operation of the extraction device performed subsequent to FIG. 12C;

FIG. 12E is a front view illustrating an operation of the extraction device performed subsequent to FIG. 12D;

FIG. 12F is a front view illustrating an operation of the extraction device performed subsequent to FIG. 12E;

FIG. 13A is a front view illustrating an operation of the extraction device performed subsequent to FIG. 12F;

FIG. 13B is a front view illustrating an operation of the extraction device performed subsequent to FIG. 13A;

FIG. 13C is a front view illustrating an operation of the extraction device performed subsequent to FIG. 13B;

FIG. 13D is a front view illustrating an operation of the extraction device performed subsequent to FIG. 13C;

FIG. 13E is a front view illustrating an operation of the extraction device performed subsequent to FIG. 13D;

FIG. 20A1 is a diagram for describing a main overall operation flow of the medication support apparatus of FIGS. 1A and 1B;

FIG. 20A2 is a diagram for describing the main overall operation flow of the medication support apparatus of FIGS. 1A and 1B;

FIG. 20A3 is a diagram for describing the main overall operation flow of the medication support apparatus of FIGS. 1A and 1B;

FIG. 20B is a diagram for describing the main overall operation flow of the medication support apparatus of FIGS. 1A and 1B;

FIG. 20C is a diagram for describing the main overall operation flow of the medication support apparatus of FIGS. 1A and 1B;

FIG. 25 is a diagram illustrating a "Basic Information" screen displayed on the touch panel;

FIG. 26 is a diagram illustrating a "Medication Information" screen displayed on the touch panel;

FIG. 28 is a diagram illustrating a "Medication Information (Medicine Delivery Tray)" screen displayed on the touch panel;

FIG. 29 is a diagram illustrating a "Medication Information" screen displayed on the touch panel;

FIG. 30 is a diagram illustrating a "Registration OK" screen displayed on the touch panel;

FIG. 31 is a diagram illustrating a "Confirmation of Registration Information (Storage/Tray)" screen displayed on the touch panel;

FIG. 32 is a diagram illustrating a "Confirmation of Registration Information (Medication Timing)" screen displayed on the touch panel;

FIG. 33 is a diagram illustrating a "Change/Deletion" screen displayed on the touch panel;

FIG. 34C is a screen displayed on the touch panel when an error occurs in the extraction of a pack or the medicine delivery processing;

FIG. 36 including FIGS. 36A and 36B is a main flowchart describing a process of extracting packs to a process of arranging the extracted packs on the medicine delivery tray;

FIG. 37A is a front view illustrating a configuration of a storage and an extraction device according to a first modification;

FIG. 37B is an enlarged bottom view of a lowermost pack stored in the storage according to the first modification.

Figure 2A:
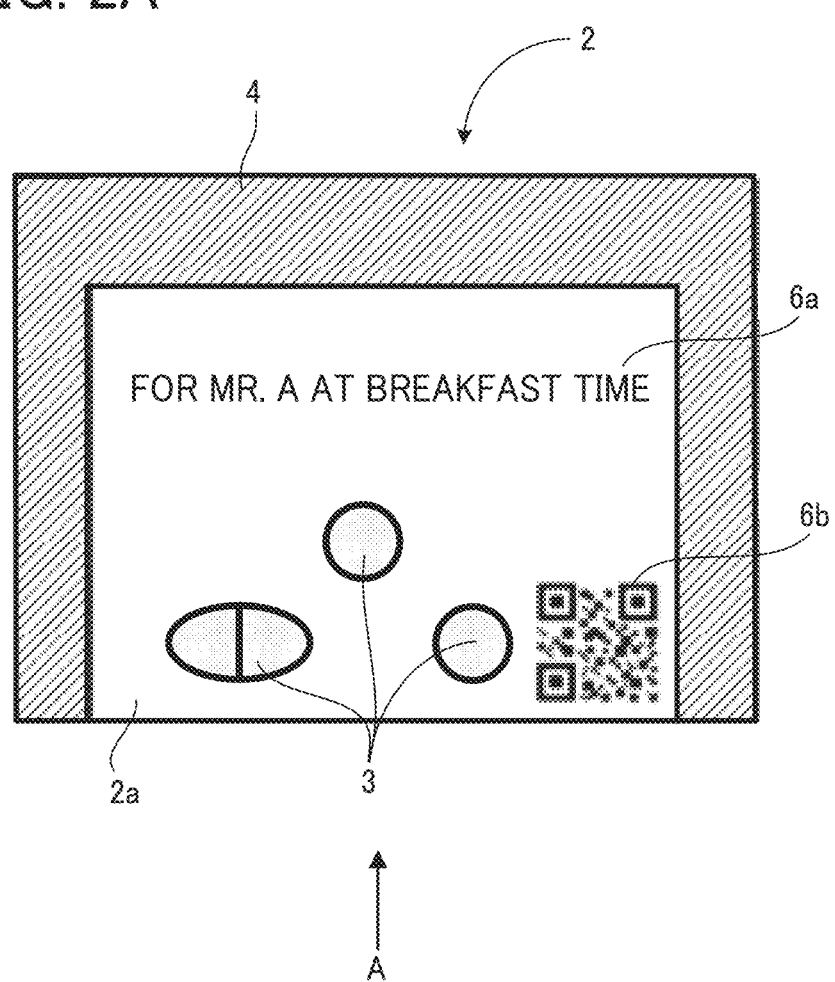
FIG. 2A is a plan view illustrating a general form of a single pack of medicine.

The accompanying drawings are intended to depict embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise.

In describing embodiments illustrated in the drawings, specific terminology is employed for the sake of clarity. However, the disclosure of this specification is not intended to be limited to the specific terminology so selected and it is to be understood that each specific element includes all technical equivalents that have a similar function, operate in a similar manner, and achieve a similar result.

Hereinafter, embodiments of the present disclosure including examples will be described in detail with reference to the drawings. Throughout the embodiments and examples, constituent elements (members, components) and the like having the same functions, shapes, and the like are once described, and thereafter duplicated description thereof is omitted with provision of the same reference signs unless there is a risk of confusion.

Figures 1A, 1B:
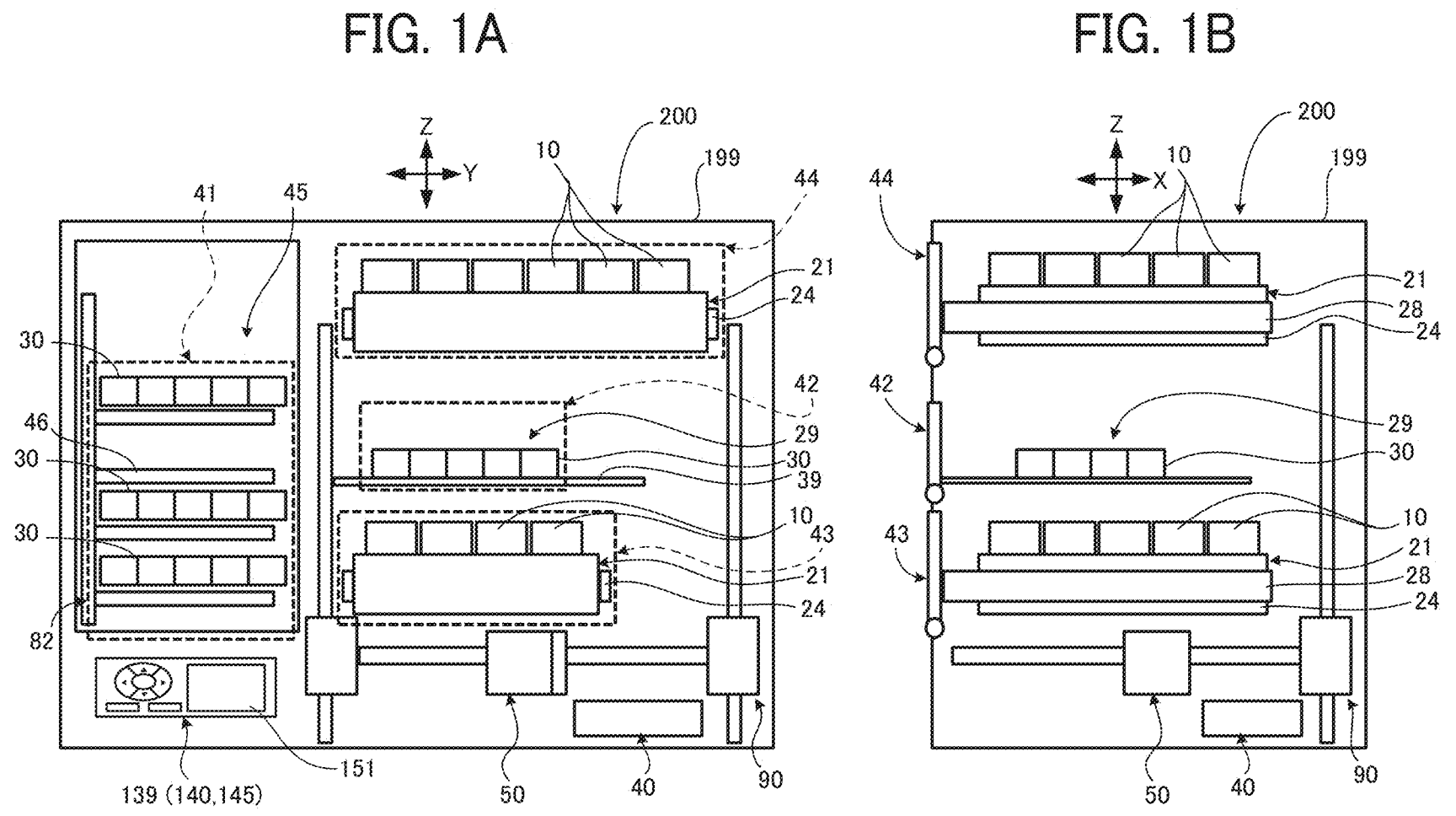

A main configuration of an entire medication support apparatus according to an embodiment of the present disclosure will be described with reference to FIGS. 1A and 1B. FIG. 1A is a front view schematically illustrating a main configuration of the entire medication support apparatus according to an embodiment of the present disclosure, and FIG. 1B is a side view schematically illustrating a side configuration of FIG. 1A.

As illustrated in FIGS. 1A and 1B, a medication support apparatus 200 according to an embodiment of the present disclosure includes a plurality of storages 10 as storages for storing a medicine pack (hereinafter, also simply referred to as a "pack") in which medicine is packaged, and a medicine delivery tray 30 as a medicine delivery part/medicine delivery table having a plurality of partitions (described later) for arranging a specific pack. Hereinafter, an installation site of the medicine delivery tray 30 (meaning a site where the pack is to be automatically delivered to the medicine delivery tray 30) will be referred to as a medicine delivery unit 29.

In FIGS. 1A and 1B, a horizontal direction or a lateral direction of the medication support apparatus 200 is defined as an X direction, a front-back direction or a depth direction is defined as a Y direction, and an up-down direction or a longitudinal direction (which is also a vertical direction) is defined as a Z direction.

The medication support apparatus 200 also includes a first inlet/outlet 41, a second inlet/outlet 42, a third inlet/outlet 43, and a fourth inlet/outlet 44 as inlet/outlet that allow the medicine delivery tray 30 to enter and exit a main body frame 199 as an apparatus main body, an extraction device 50 as an extraction device that extracts a specific pack from the storage 10, and a transfer device 90 as a transfer device that transfers the pack extracted from the storage 10.

The medication support apparatus 200 also includes a medicine delivery tray stock device 45 as a medicine delivery part container that stores a plurality of medicine delivery trays 30. In the medicine delivery tray stock device 45, disposed is a medicine delivery tray vertical movement section 82 as a medicine delivery part vertical movement device for moving the medicine delivery tray 30 in the Z direction. A detailed configuration of the medicine delivery tray stock device 45 will be described later.

The medication support apparatus 200 also includes an information system device 139 that manages information on the pack and an information system of the medicine delivery tray. The information system device 139 includes a pack information management unit 140 as a pack information management unit that manages information on a pack, and a medicine delivery information management unit 145 as a medicine delivery information management unit that manages position information of a pack extracted from the storage on the medicine delivery tray.

In a lower portion of the medication support apparatus 200, disposed is a wrong pack depository 40 as a wrong pack depository that, if a medicine pack extracted from the storage 10 is a wrong pack that should not be arranged on the medicine delivery tray 30, stores the wrong pack. Whether a medicine pack is a problem-free regular pack to be arranged on the medicine delivery tray 30 is determined by a controller 150 having a control function of the pack information management unit 140. Details thereof will be described later.

In the medication support apparatus 200, the wrong pack in the storage 10 is kept (or discarded) in the wrong pack depository 40 which is a place different from the medicine delivery tray 30. The presence of the wrong pack depository 40 makes clear the location of the wrong pack. Even if the wrong pack is extracted from the storage, the medicine delivery processing can be continued by removing the wrong pack. In addition, keeping the wrong pack in the medication support apparatus 200 (not taking out of the medication support apparatus 200) prevents the possibility of the wrong pack being mistakenly used at the time of dosage.

The storages 10 are each inserted and set into the body frame 199 from the third inlet/outlet 43 and the fourth inlet/outlet 44. The opening and closing doors of the third inlet/outlet 43 and the fourth inlet/outlet 44 are opened, a drawer 21 in which the storages 10 are set is extracted to the front, and the storage 10 is detached and attached.

The first inlet/outlet 41 allows the medicine delivery trays 30 to be collectively removed from or inserted into the main body frame 199. The second inlet/outlet 42 is provided so that the pack can be extracted immediately after being arranged (hereinafter, also referred to as "set" or "inserted") on the medicine delivery tray 30.

Figure 2B:
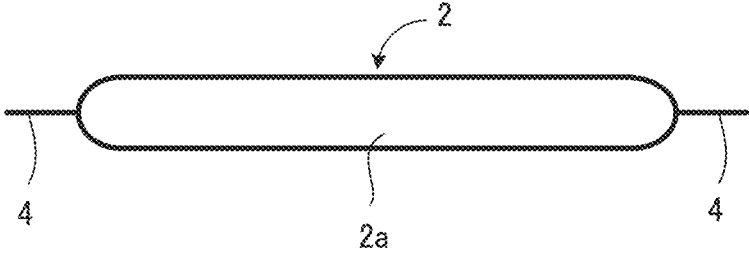
FIG. 2B is a side view of the pack of medicine illustrated in FIG. 2A as viewed from the direction of arrow A.

An outline of a single pack of medicine will be described with reference to FIGS. 2A and 2B. FIG. 2A is a plan view illustrating a general form of a single pack of medicine, and FIG. 2B is a side view of the pack of medicine of FIG. 2A as viewed from the direction of arrow A. FIG. 2B slightly schematically illustrates the pack of medicine without illustration of medicine.

As illustrated in FIGS. 2A and 2B, one pack of medicine 2 (hereinafter, also simply referred to as "pack 2") contains medicine 3 such as capsules or tablets packed in a bag. The pack 2 includes a bag 2a covering the medicine 3 and a three-side pressure-bonded portion 4 which forms a leak-proof portion for preventing leakage of the medicine 3 from the bag 2a, which is indicated by hatching.

The pack 2 is formed of, for example, a transparent or translucent resin film through which the medicine 3 can be visually recognized. In the example illustrated in FIG. 2A, the pack 2 is rectangular in shape in a plan view and has the pressure-bonded portion 4 in which three sides are pressure-bonded or welded, so that the medicine 3 is bagged therein so as not to be leaked. The side of the resin film sheet facing the bag 2a is usually folded in two, and the medicine 3 is sandwiched therebetween.

One pack 2 can be torn off by hand or cut and separated with a dedicated cutter by a medication assistant or the like so that the medicine recipient can take one dose of medicine, unlike a belt-like sheet of continuous packs in which a plurality of packs is coupled with perforations in the middle of the pressure-bonded portion between adjacent packs (a general form of medicine provided and sold to a user at pharmacies or the like, where a required number of doses for the user is cut into a continuous sheet). One pack 2 is usually a unit of medicine for a user who takes the medicine.

To the pack, first medication-related information is added as information regarding medication, such as a medicine recipient and timing of medication. In the pack 2 illustrated in FIGS. 2A and 2B, as the first medication-related information, medication-related information 6a and medication-related information 6b are added. In the medication-related information 6a, the name of the user (hereinafter, also referred to as a "medicine recipient") who takes the medicine 3 in the pack 2 and the time for taking the medicine 3 (medication timing) are represented by a character string. The medication-related information 6b is represented by a quick response (QR) code (registered trademark).

To the pack 2 illustrated in FIGS. 2A and 2B, the medication-related information 6a of the character string and the medication-related information 6b of the QR code (registered trademark) are added. However, the present disclosure is not limited thereto, and one of the medication-related information 6a and the medication-related information 6b may be added, or a radio frequency identification (RFID) tag or the like used when tag information is read using a barcode or near field communication may be added.

Furthermore, the first medication-related information also includes the type of the medicine (including the shape of the medicine) and the number of tablets prescribed in the pack, information imprinted on the medicine itself, and the like.

As the first medication-related information, individual information may be acquired and used, or a plurality of pieces of information may be acquired and used in combination. For example, if confirmation of the user is required, the information of the user alone is sufficient. If it is desired to prevent forgetting to take an important medicine, information of the number of tablets of the medicine and the shape of the medicine in the pack is confirmed together with the information of the user. That is, the medication-related information includes at least one of the name of the user, the time for taking the medicine in the pack (medication timing), and the type and number of medicines prescribed in the pack.

Figure 3:
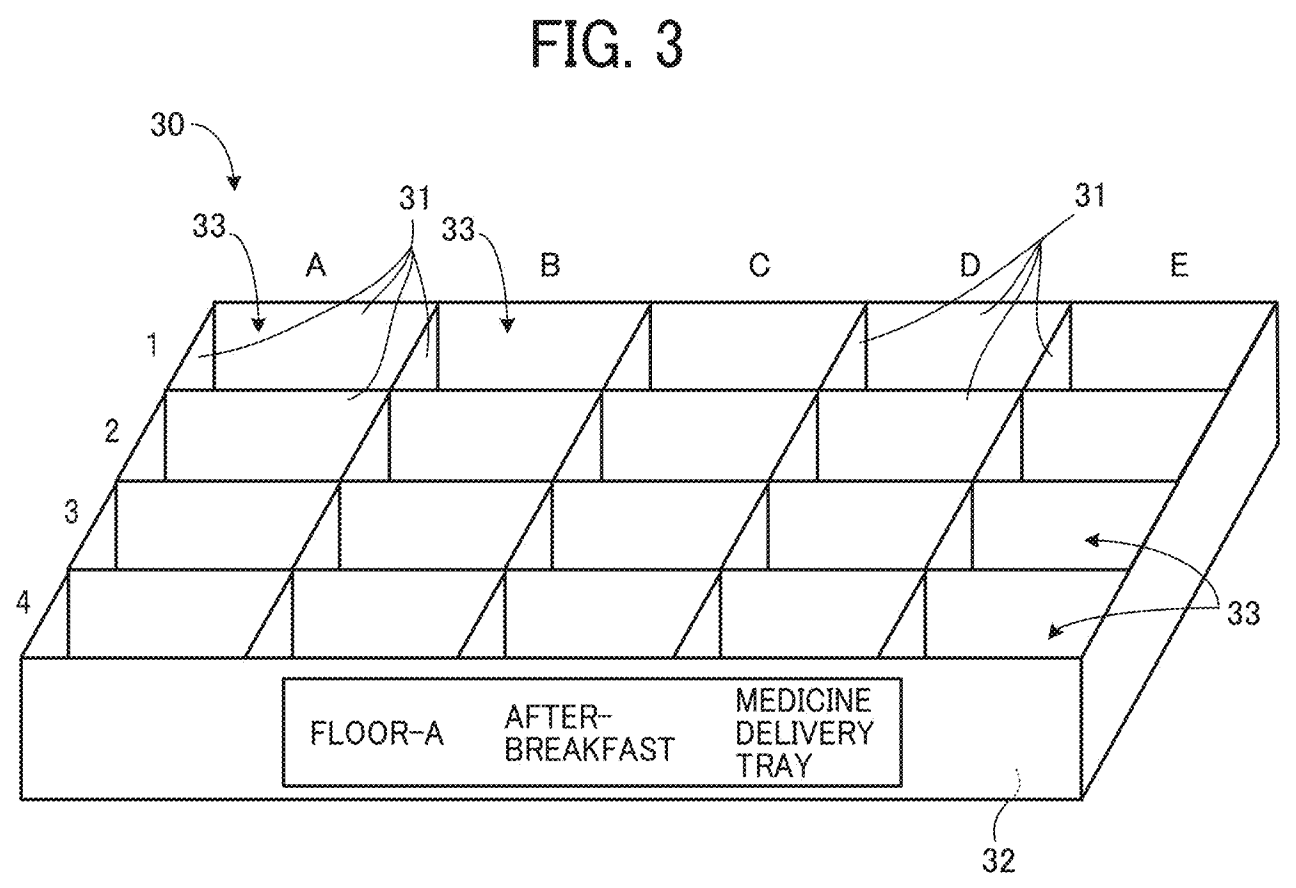

The medicine delivery tray will be described with reference to FIG. 3. FIG. 3 is an external perspective view illustrating a configuration example of the medicine delivery tray.

As illustrated in FIG. 3, the medicine delivery tray 30 has partition walls 31 which are partition members as a plurality of partitions for arranging a specific pack, and is partitioned by the four erected partition walls 31. The medicine delivery tray 30 includes a total of 20 sections 33 divided by a plurality of partition walls 31 in the example of the drawing. That is, the medicine delivery tray 30 is intended to arrange a specific pack in a predetermined (specific) section 33 as a predetermined position partitioned by the plurality of partitions.

The 20 sections 33 of the medicine delivery tray 30 can be expressed as components of a matrix including five columns of A, B, C, D, and E in the vertical direction (line feed direction) and four rows of 1, 2, 3, and 4 in the lateral direction (character feed direction). As a result, each of the 20 sections 33 of the medicine delivery tray 30 can be uniquely positioned by the components (hereinafter, also referred to as addresses) of the matrix of five columns and four rows. Further, the medicine delivery tray 30 includes a bottom wall 32 on which the arranged pack (not illustrated) is placed. In this manner, the medicine delivery tray 30 is configured such that the plurality of (four) partition walls 31 and the common bottom wall 32 ensure that a specific pack (not illustrated) is arranged in the specific section 33 without mixing with a pack (not illustrated) in another section 33 or falling off from the bottom wall 32.

In the medicine delivery tray 30 illustrated in FIG. 3, "floor-A after-breakfast medicine delivery tray" displayed on the front outer wall surface indicates, for example, a medicine delivery tray on which a pack to be taken after breakfast (which is also the breakfast time of the medication-related information 6a of the pack 2 illustrated in FIGS. 2A and 2B) of a plurality of users living on the same floor A in a nursing home or the like is arranged.

In A1 (hereinafter, "A1" is simply expressed as a matrix component), which is a specific section 33 of the medicine delivery tray 30, the regular pack 2 to be taken by the medicine recipient A illustrated in FIGS. 2A and 2B after breakfast (breakfast time) is arranged. In the specific sections 33 (A2 to A4, B1 to B4, C1 to C4, D1 to D4, E1 to E4) other than A1 of the medicine delivery tray 30, regular packs to be taken after breakfast (breakfast time) by users other than A who live on the same floor A are arranged so as not to overlap with each other.

That is, the medicine delivery tray 30 illustrated in FIG. 3 includes a total of 20 sections 33 divided by the plurality of partition walls 31, and the set/insertion positions are determined for the corresponding users depending on the packs to be taken. In other words, the plurality of (20) sections 33 in the medicine delivery tray 30 is uniquely allocated to the plurality of users (20 persons including A) at the same timing of medication. There may be a case where a specific user does not need to take medicine at a specific timing of medication, and in such a case, a pack for the specific user is not set in the corresponding section of the medicine delivery tray, and the section is in a blank state.

The medicine delivery tray 30 is not limited to the medicine delivery tray 30 illustrated in FIG. 3. For example, in addition to the "floor-A, after-breakfast medicine delivery tray" in FIG. 3, the medication timing alone may be changed to prepare a medicine delivery tray for "after lunch", "after dinner", or a medicine delivery tray for "before going to bed".

In the medicine delivery trays including the medicine delivery tray 30 of FIG. 3, the specific packs 2 are arranged in the specific sections 33 as predetermined positions partitioned by the plurality of partition walls 31, and the plurality of sections 33 of the medicine delivery tray 30 is allocated to medicine recipients at the same timing of medication.

According to the above medicine delivery tray, the sections are determined for the corresponding medicine recipients so that a staff member or the like in a nursing home and the like using the medication delivery tray for medication assistance (including a pharmacist, a nurse, a care worker, or a medication assistant, and the same applies hereinafter) picks up the medicine from the same sections (addresses) every time, which leads to prevention of erroneous medicine taking. That is, since the sections are not changed from day to day, it is possible to reduce the work of staff members and the like in a nursing home, a welfare facility, and the like.

The medicine delivery tray 30 is not limited to the above medicine delivery tray 30. The plurality of sections 33 of the medicine delivery tray 30 may be allocated to the medicine recipients by medication timing as an example. Specifically, the plurality of sections 33 may be allocated to the corresponding medicine recipients by medication timing of the pack 2 to be taken in the morning, the daytime, the evening, or before going to bed. In the medicine delivery tray 30 of such an example, it is possible to manage the medicine delivery trays 30 based on the floor or rooms in which a plurality of medicine recipients resides, and to deliver the packs 2 for the day (or several days) to the medicine delivery tray 30 in advance.

According to the above example, allocating the sections by medication timing, such as morning, daytime, evening, or before going to bed, makes it possible to prevent the medication timing for each medicine recipient from being mistaken. The present disclosure is not limited to the above-described configuration example of the medicine delivery tray 30, and various examples are conceivable by combinations of the medicine recipient and the medication timing.

Figures 4A, 4B:
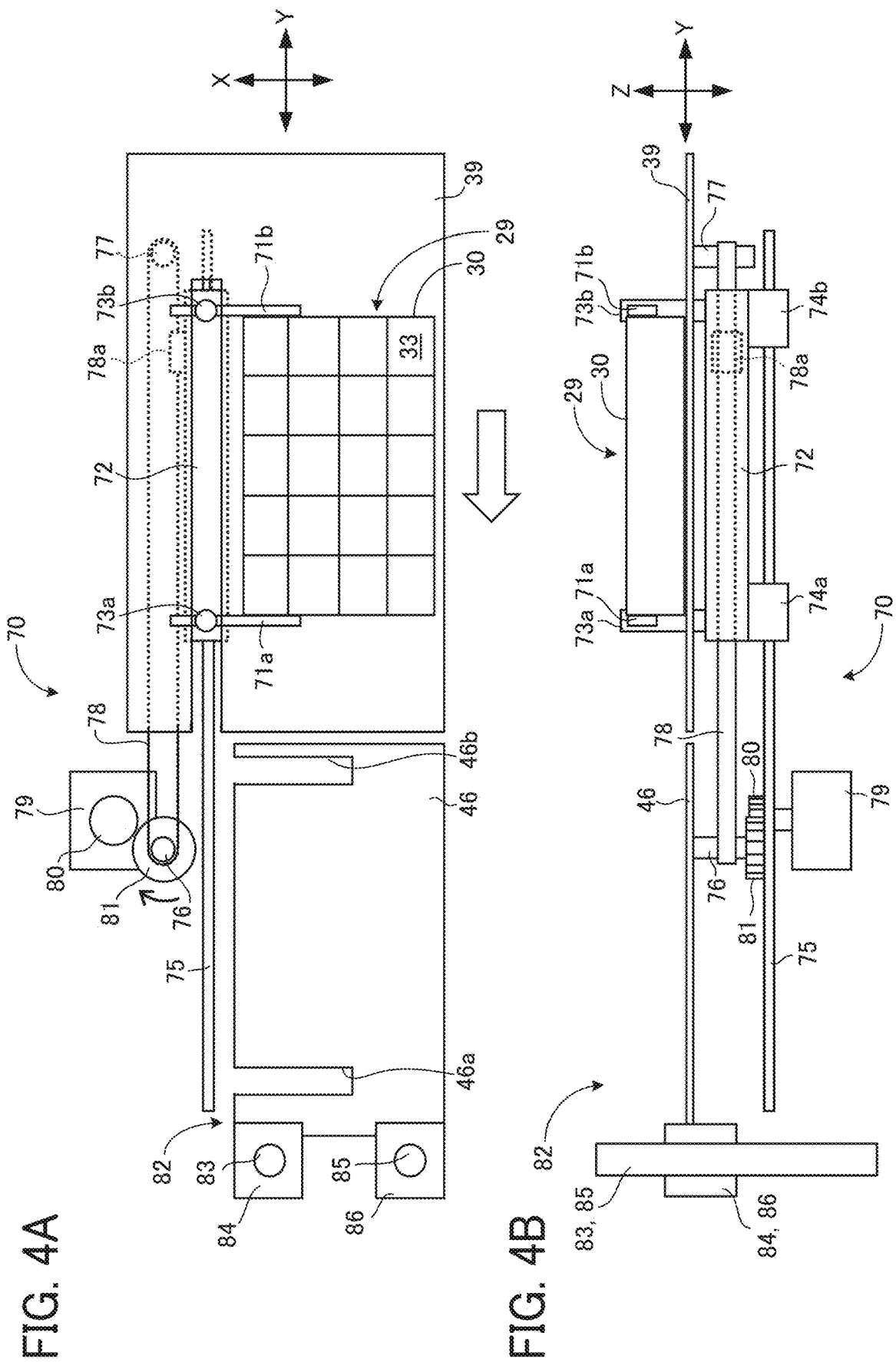
FIG. 4A is a plan view illustrating a configuration and operation of a main part of a medicine delivery tray horizontal movement section in a medicine delivery tray stock device.
FIG. 4B is a front view of the main part of the medicine delivery tray horizontal movement section illustrated in FIG. 4A.
Figures 5A, 5B:
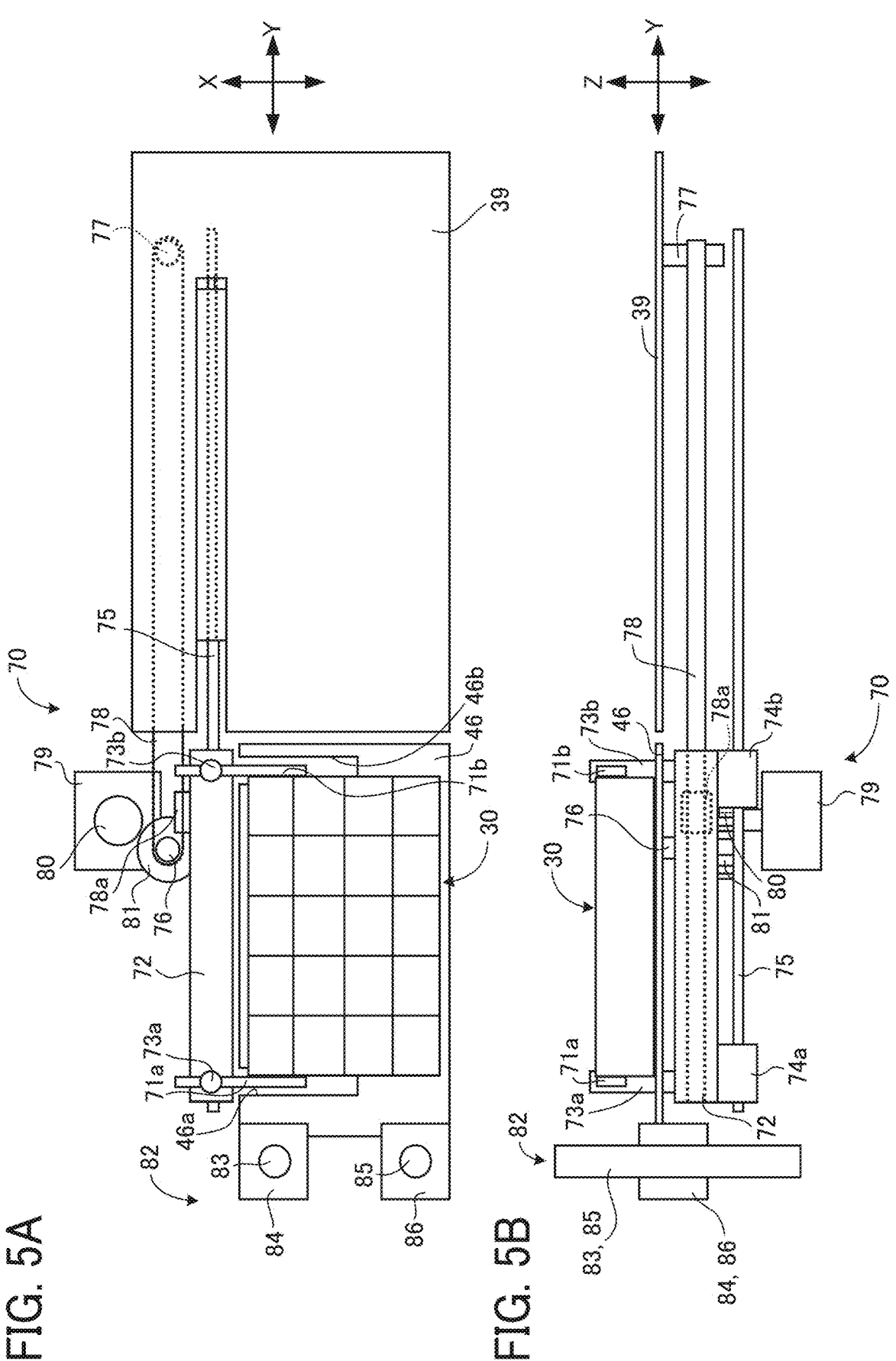
FIG. 5A is a plan view illustrating a configuration and operation of the main part of the medicine delivery tray horizontal movement section in the medicine delivery tray stock device.
FIG. 5B is a front view of the main part of the medicine delivery tray horizontal movement section illustrated in FIG. 5A.
Figure 6:
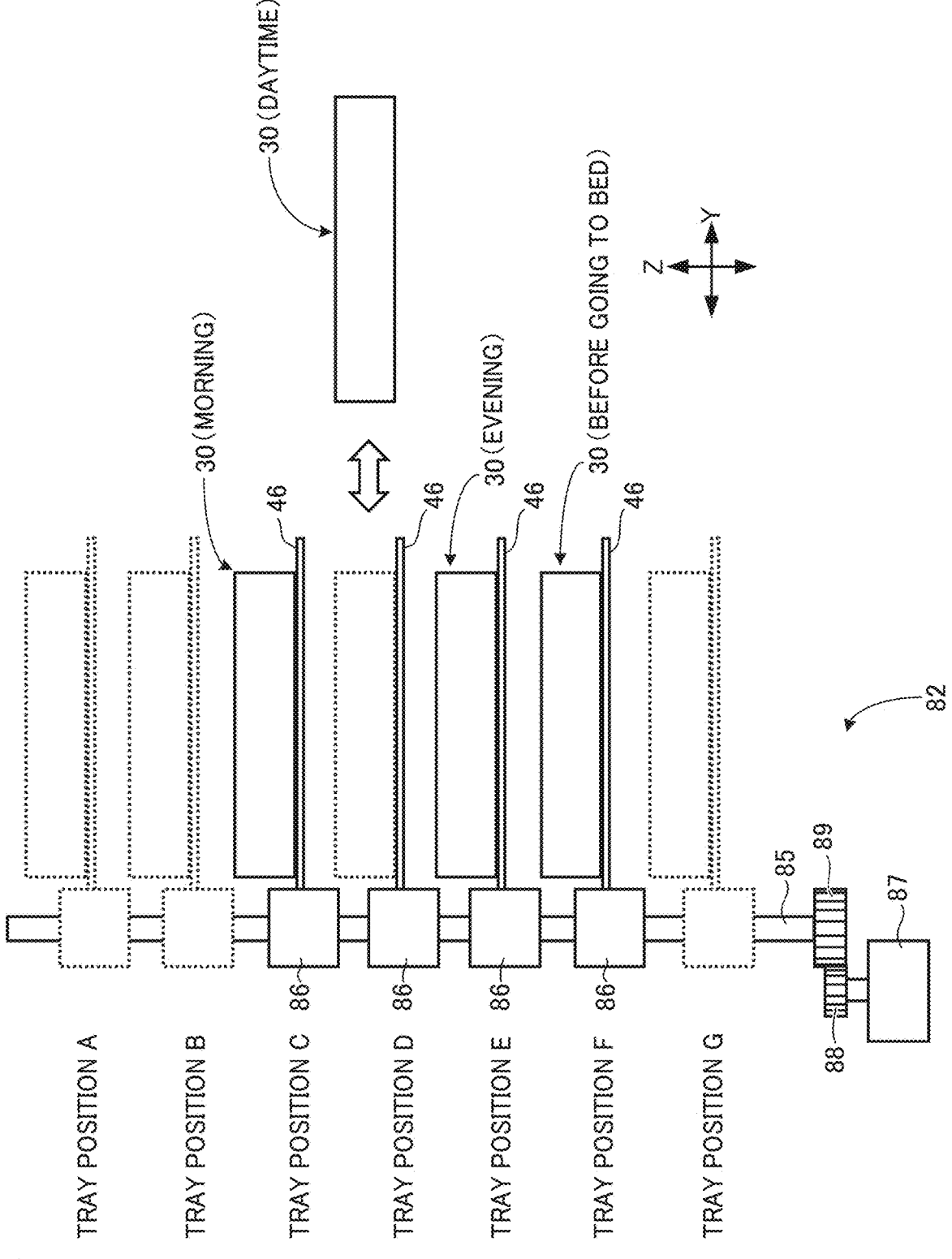
FIG. 6 is a front view illustrating a configuration and operation of a main part of a medicine delivery tray vertical movement section in the medicine delivery tray stock device.

A detailed configuration and operation of the medicine delivery tray stock device 45 of FIGS. 1A and 1B will be described with reference to FIGS. 4A to 6. FIGS. 4A and 5A are plan views illustrating a configuration and operation of a main part of a medicine delivery tray horizontal movement section provided in the medicine delivery tray stock device, FIG. 4B is a front view of the main part of a medicine delivery tray horizontal movement section illustrated in FIG. 4A, and FIG. 5B is a front view of the main part of a medicine delivery tray horizontal movement section illustrated in FIG. 5A. FIG. 6 is a front view illustrating a configuration and operation of a main part of the medicine delivery tray vertical movement section provided in the medicine delivery tray stock device.

The medicine delivery tray stock device 45 includes a medicine delivery tray horizontal movement section 70 as a medicine delivery part horizontal movement device that selects one medicine delivery tray 30 from the medicine delivery tray stock device 45 storing a plurality of medicine delivery trays 30 and moves the selected medicine delivery tray in the Y direction. The medicine delivery tray stock device 45 is provided with a medicine delivery tray stock device bottom plate 46 on which the medicine delivery tray 30 is placed. The medicine delivery tray stock device bottom plate 46 has a pair of notches 46a and 46b formed to prevent interference in the Z direction with a pair of arms 71a and 71b sandwiching the medicine delivery tray 30 as described later, and to allow the movement in the Z direction of the medicine delivery tray 30 sandwiched by the pair of arms 71a and 71b.

As illustrated in FIGS. 4A and 4B, one medicine delivery tray 30 is placed on a flat bottom plate 39. In the medicine delivery tray horizontal movement section 70, disposed are the pair of arms 71a and 71b that sandwich the left and right end portions of the medicine delivery tray 30 placed on the bottom plate 39, an arm holding member 72 that holds the arms 71a and 71b, and arm coupling members 73a and 73b that couple the arms 71a and 71b and the end portions of the arm holding member 72. In the medicine delivery tray horizontal movement section 70, also disposed are guide portions 74a and 74b fastened to the left and right end portions of the arm holding member 72 with through holes, and a guide rod 75 penetrating the holes in the guide portions 74a and 74b and integrally moving and guiding the pair of arms 71a and 71b, the arm holding member 72, and the arm coupling members 73a and 73b in the horizontal direction Y.

The medicine delivery tray horizontal movement section 70 includes a medicine delivery tray horizontal moving mechanism that integrally moves the pair of arms 71a and 71b, the arm holding member 72, and the arm coupling members 73a and 73b in the horizontal direction Y.

The medicine delivery tray horizontal moving mechanism includes an endless belt 78 wound around a driving pulley 76 and a driven pulley 77, a belt gripping portion 78a integrally coupling the belt 78 and the arm holding member 72, a pulley gear 81 secured to a shaft of the driving pulley 76, and a horizontal movement motor 79 secured to an output shaft of a motor gear 80 always meshing with the pulley gear 81 and secured to the main body frame 199 side. The horizontal movement motor 79 is a control target driving member of the medicine delivery tray horizontal movement section 70 (see FIG. 17 described later).

The horizontal movement motor 79 is preferably a stepping motor driven by pulse input in terms of accurate drive control, but may be a direct current (DC) motor or the like. The same applies to a motor which is a drive unit of each drive mechanism described later.

As illustrated in FIGS. 4A and 4B, when the horizontal movement motor 79 rotates in the counterclockwise direction in a state where both end portions of the medicine delivery tray 30 are sandwiched by the arms 71a and 71b, the driving pulley 76 and the belt 78 are rotationally driven in the clockwise direction through the rotation transmission with the pulley gear 81 meshing with the motor gear 80. As a result, the pair of arms 71a and 71b, the arm holding member 72, and the arm coupling members 73a and 73b integrally move in the leftward direction indicated by the thick arrow in the drawing, in accordance with the movement of the belt 78 while the guide portions 74a and 74b are guided by the guide rod 75.

After the pack (not illustrated) is placed on the medicine delivery tray 30, the medicine delivery tray 30 is moved to the medicine delivery tray stock device 45. The medicine delivery tray 30 illustrated in FIGS. 5A and 5B represents a state in which the medicine delivery tray 30 on the bottom plate 39 in a state of being sandwiched by the arms 71a and 71b is moved to a predetermined position where the medicine delivery tray 30 is to be delivered onto the medicine delivery tray stock device bottom plate 46 by the above-described operation illustrated in FIGS. 4A and 4B.

A medicine delivery tray detection sensor 131 (illustrated in a block diagram of FIG. 17 described later) detects that the medicine delivery tray 30 is at a predetermined position on the bottom plate 39 in the medicine delivery unit 29 of FIGS. 4A and 4B. A medicine delivery tray detection sensor 130 (illustrated in a block diagram of FIG. 17 described later) arranged in the medicine delivery tray stock device 45 detects that the medicine delivery tray 30 has moved to the predetermined position on the medicine delivery tray stock device bottom plate 46.

As illustrated in FIGS. 4A to 6, in the medicine delivery tray vertical movement section 82, disposed are four guide members 86 (indicated by solid lines) to which the medicine delivery tray stock device bottom plate 46 is secured and in which a spiral concavo-convex groove shape (screw shape, not illustrated) is formed in the inner peripheral portion, and a drive rod 85 (indicated by solid lines) to which the medicine delivery tray stock device bottom plate 46 is secured, which is arranged at a predetermined distance from the guide member 86 in the X direction, and in which a spiral concavo-convex groove shape (screw shape, not illustrated) is formed in the outer peripheral portion. The four guide members 84 have a substantially cubic shape, and are movable in the Z direction on the drive rod 85 as a drive guide member through engagement between the spiral concavo-convex groove shapes (screw shapes).

In the medicine delivery tray vertical movement section 82, disposed are four guide members 84 (hidden behind the guide member 86 and not visible in FIG. 6) to which the medicine delivery tray stock device bottom plate 46 is secured and in which no spiral concavo-convex groove shape is formed in the inner peripheral portion, and four guide rods 83 (hidden behind the drive rod 85 and not visible in FIG. 6) to which the medicine delivery tray stock device bottom plate 46 is secured, which are disposed at a predetermined distance from the guide member 84 in the X direction, and in which no spiral concavo-convex groove shape is formed in the outer peripheral portion. The four guide members 84 have a substantially cubic shape and are movable in the Z direction through engagement with the guide rod 83 as a guide member.

The medicine delivery tray vertical movement section 82 includes a medicine delivery tray vertical movement mechanism that moves the four guide members 84 securing the medicine delivery tray stock device bottom plate 46 and the four guide members 86 securing the medicine delivery tray stock device bottom plate 46 in the Z direction.

The medicine delivery tray vertical movement mechanism includes a vertical movement motor 87 secured to the main body frame 199 side and having a drive gear 88 as an output shaft, and a drive rod gear 89 secured to the drive rod 85 and always meshed with the drive gear 88. The vertical movement motor 87 is a control target drive member of the medicine delivery tray vertical movement section 82 (see FIG. 17 described later). The vertical movement motor 87 may be a stepping motor driven by pulse input or the like.

In FIG. 6, when the vertical movement motor 87 is rotationally driven in a predetermined direction, the drive rod 85 is rotated in a direction opposite to the predetermined direction via the driving force transmission from the drive rod gear 89 meshing with the drive gear 88, so that the guide members 86 move to any side in the Z direction via the engagement between the spiral concavo-convex groove shapes (screw shapes). At this time, as illustrated in FIG. 6, the medicine delivery trays 30 on the medicine delivery tray stock device bottom plates 46 are moved to the corresponding positions of the medicine delivery trays 30 ("tray position A" to "tray position G" are described in FIG. 6).

In the example illustrated in FIG. 6, the medicine delivery tray stock device bottom plate 46 on which the medicine delivery tray 30 holding the packs to be taken in the morning is placed can be moved to the tray position C, the medicine delivery tray stock device bottom plate 46 on which the medicine delivery tray 30 holding the packs to be taken in the daytime is placed can be moved to the tray position D, the medicine delivery tray stock device bottom plate 46 on which the medicine delivery tray 30 holding the packs to be taken in the evening is placed can be moved to the tray position E, and the medicine delivery tray stock device bottom plate 46 on which the medicine delivery tray 30 holding the packs to be taken before going to bed is placed can be moved to the tray position F. The drawing indicates that, at the tray position D, the medicine delivery tray 30 holding the packs to be taken in the daytime can be moved to the left in the Y direction and placed on the medicine delivery tray stock device bottom plate 46, or the medicine delivery tray 30 can be moved to the right in the Y direction and taken off from the medicine delivery tray stock device bottom plate 46.

Figures 7A, 7B:
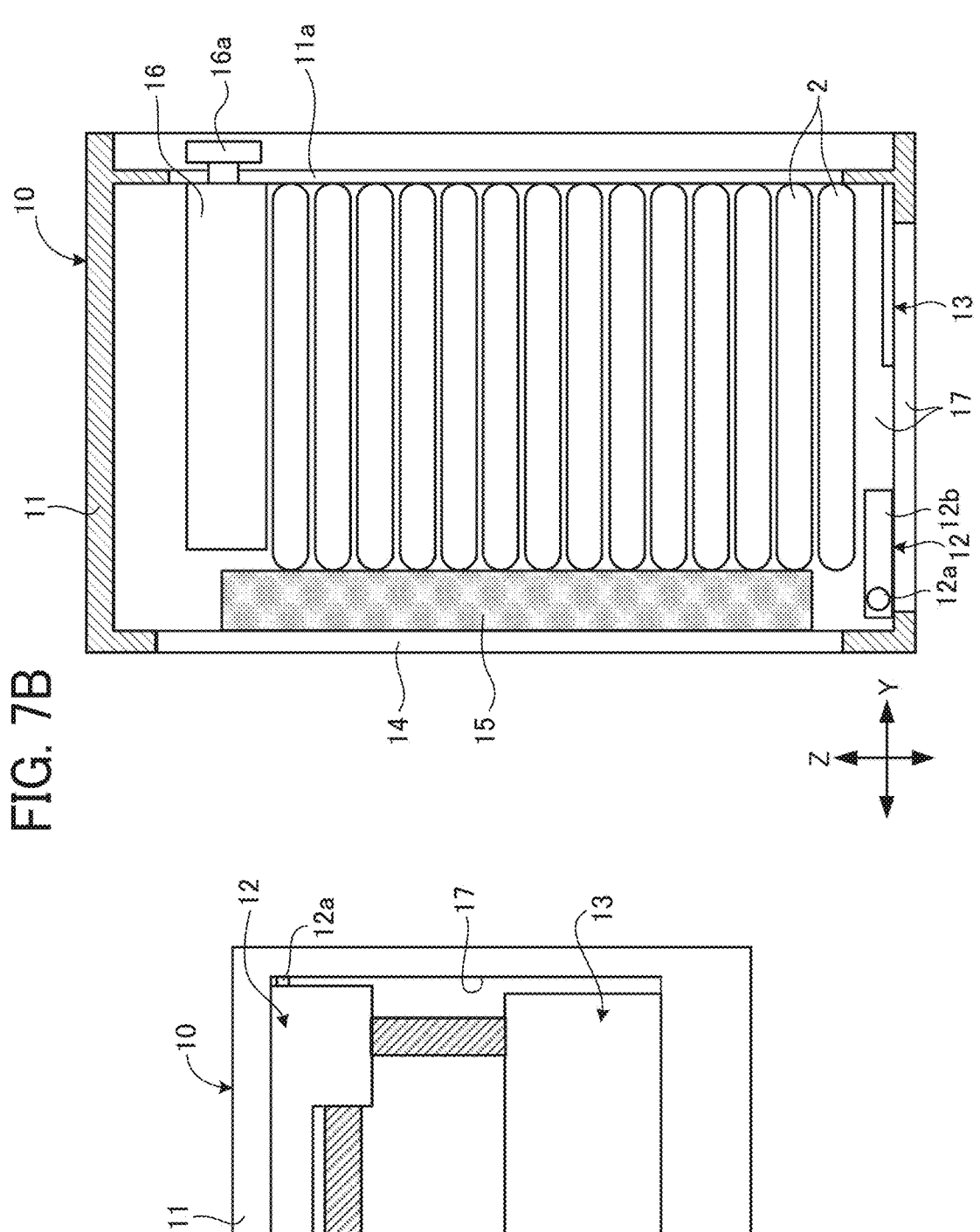
FIG. 7A is a front view of a storage.
FIG. 7B is a side cross-sectional view of the storage.
Figure 8:
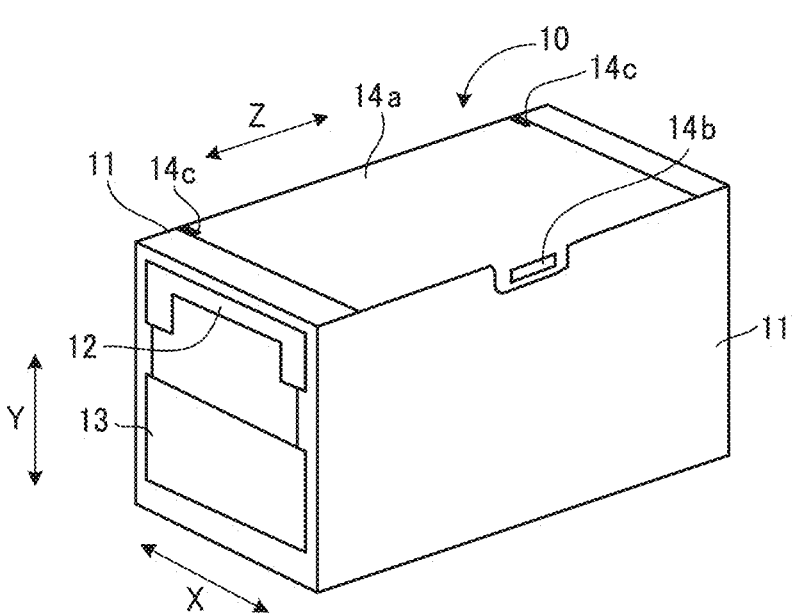
FIG. 8 is an external perspective view of the storage.

An example of a detailed configuration and operation of the storage will be described with reference to FIGS. 7A, 7B, and 8. FIG. 7A is a bottom view of the storage, and FIG. 7B is a longitudinal cross-sectional view of the storage. FIG. 8 is an external perspective view of the storage. In FIG. 7B, in order to simplify the drawing, the illustration of the pressure-bonded portions 4 of the packs 2 stored in the storage 10 is intentionally omitted, and the packs 2 are schematically illustrated in an enlarged and exaggerated manner. For the same purpose, the hatching of the cross sections of the supporter (left supporter 12, right supporter 13, and the like) is also omitted.

The storages 10 of the present embodiment are configured to store the plurality of packs 2 in a stacked manner. The "storing in a stacked manner" here means storing packs in a substantially horizontal state or a flat stacked state.

As illustrated in FIGS. 7A, 7B, and 8, each of the storages 10 includes a case 11 that stores the plurality of packs 2, a lid 14 that enables the packs 2 to be taken in and out, a movable plate 16 that prevents falling of the packs 2, and a pack posture holder 15 that holds the posture of the packs 2.

The storage 10 also includes the left supporter 12 and the right supporter 13 as supporters that support or hold the packs 2 in the case 11, and a pack extraction opening 17 that allows the packs 2 in the case 11 to be extracted and pass therethrough.

One feature of the storage 10 of the present embodiment is that an extraction target device for the extraction device 50 (see FIGS. 1A, 1B, and the like) to extract the packs 2 from the storage 10 is provided in a lower portion or a bottom portion of the storage 10. That is, the extraction target device are provided in the lower portion of the storage 10, and includes the left supporter 12 and the right supporter 13 as supporters that support the packs 2 extracted from the storage 10 at a plurality of places, and the pack extraction opening 17.

The case 11 is integrally or separately formed of resin, for example.

The pack posture holder 15 is formed of sponge rubber having appropriate elasticity. Therefore, the pack posture holder 15 and the movable plate 16 normally hold the postures of the plurality of packs 2 stored in the case 11 (hold the postures of the packs 2 in an orderly and substantially horizontal state along the Z direction).

The movable plate 16 also has a function of moving the lowermost pack 2 to the vicinity of the pack extraction opening 17 after the first pack out of the maximum number of packs 2 that can be stored in the case 11 is extracted.

In this example, the left supporter 12 is a movable flap mechanism, and the packs to be extracted can be smoothly extracted by the extraction device 50. The left supporter 12 is provided so as to be openable and closable within the range of the pack extraction opening 17 by swinging about a rotation shaft 12a provided at a left bottom wall end of the pack extraction opening 17 opened to the bottom wall of the case 11. The left supporter 12 is formed of resin or metal, for example.

The right supporter 13 is formed of an elastically deformable elastic member. As the elastic member of the right supporter 13, for example, used is an elastically deformable resin plate material or an elastically deformable metal plate material such as stainless steel or aluminum.

That is, the left supporter 12 and the right supporter 13 are configured to allow the passage of the packs 2 when the packs 2 are extracted from the storage 10 by the extraction device 50 (see FIGS. 1A, 1B, and the like). On the other hand, the left supporter 12 and the right supporter 13 are configured to restrict the passage of the packs 2 when the packs 2 are not extracted from the storage 10, so that the plurality of packs 2 is stored and held in the case 11.

Specifically, a torsion coil spring having a biasing force in a predetermined range is attached between the rotation shaft 12a of the left supporter 12 and the left bottom wall end portion. This biasing force is set so that the left supporter 12 allows passage of the packs 2 when the packs 2 are extracted from the storage 10 by the extraction device 50, and so that the maximum number of packs 2 and the movable plate 16 to be stored are stored and held in the case 11 when the packs 2 are not extracted from the storage 10. Similarly, a predetermined range of elastic force acts between the right supporter 13 and the bottom wall end portion. Accordingly, when the packs 2 are extracted from the storage 10 by the extraction device 50, the right supporter 13 is set to allow passage of the packs 2, and when the packs 2 are not extracted from the storage 10, the maximum number of packs 2 and the movable plate 16 to be stored is set to be stored and held in the case 11. The right supporter 13 may be formed integrally with the case 11.

The lid 14 is provided to allow a staff member of a nursing home or the like to take in and out the packs 2 stored in the storage 10, and is formed to be long in the Z direction of the case 11 and have a predetermined opening width as illustrated in FIG. 7B.

In order to exhibit the above-described function, the movable plate 16 is set to reliably move at least one pack 2 left in the case 11 to the vicinity of the pack extraction opening 17 by moving downward in the Z direction in the case 11 by its own weight.

As illustrated in FIG. 7B, a long groove 11a extending in the Z direction with a predetermined width in the X direction is formed in a side wall of the case 11. A shaft 16*a* with a flange is provided at one end portion of the movable plate 16 so as to protrude from the long groove 11*a*. Since the shaft 16*a* of the movable plate 16 is guided in the Z direction along the long groove 11*a*, the posture of the packs 2 can be held in an orderly and substantially horizontal state in the down orientation in the Z direction.

In setting the packs 2 in the case 11, the lid 14 is opened around an opening/closing hinge 14*b* by holding an opening/closing handle 14*a* of the lid 14 illustrated in FIG. 8, and the packs 2 are stored in order upward from the pack extraction opening 17 on the left supporter 12 and the right supporter 13 side.

It is important to note that the setting of the packs 2 in the case 11 (whether the medication-related information 6*a* and 6*b* on the bags 2*a* of the packs 2 is faced in contact with the pack extraction opening 17 or is faced in an opposite direction) enables reading of the medication-related information 6*a* and 6*b* added to the packs 2 by a camera 135 illustrated in FIGS. 11A and 11B to be described later.

The timing at which the packs 2 are added into the storage 10 may be, for example, a timing of medical examination (usually every two weeks) of medicine recipients (residents) in a nursing home or the like, or a timing at which the packs 2 in the storage 10 run out. When any pack 2 remains in the storage 10 at the time of replenish, new packs 2 are added to the remaining pack 2 from behind.

The setting of the packs 2 and the addition of the packs 2 into the storage 10 described above are performed by a staff member or the like in a nursing home or the like, but the present disclosure is not limited thereto in a configuration in which the storage is formed into a cartridge to automatically perform the setting and addition of the packs 2.

As illustrated in FIG. 7B, the plurality of packs 2 is stored in the storage 10 and is divided by medication timing such as the medicine to be taken by A in the morning for 14 days, for example. Therefore, if A takes the medicine in the daytime, in the evening, or before going to bed other than in the morning, a total of four storages are required.

The present disclosure is not limited to the above example. For example, a single storage 10 may be used for each medicine recipient (person) such that the medicine is set in a direction toward the top from the pack extraction opening 17 which is the direction of pack extraction from the storage 10: morning of the first day, daytime, evening, before going to bed, morning of the second day, daytime, evening . . . .

In the example of the storage 10 described above, the flap mechanism in which the left supporter 12 moves (swings/opens/closes) has a simple configuration using the biasing force of the torsion coil spring, but a leaf spring or an electric motor may be used depending on the application and purpose.

Figure 9:
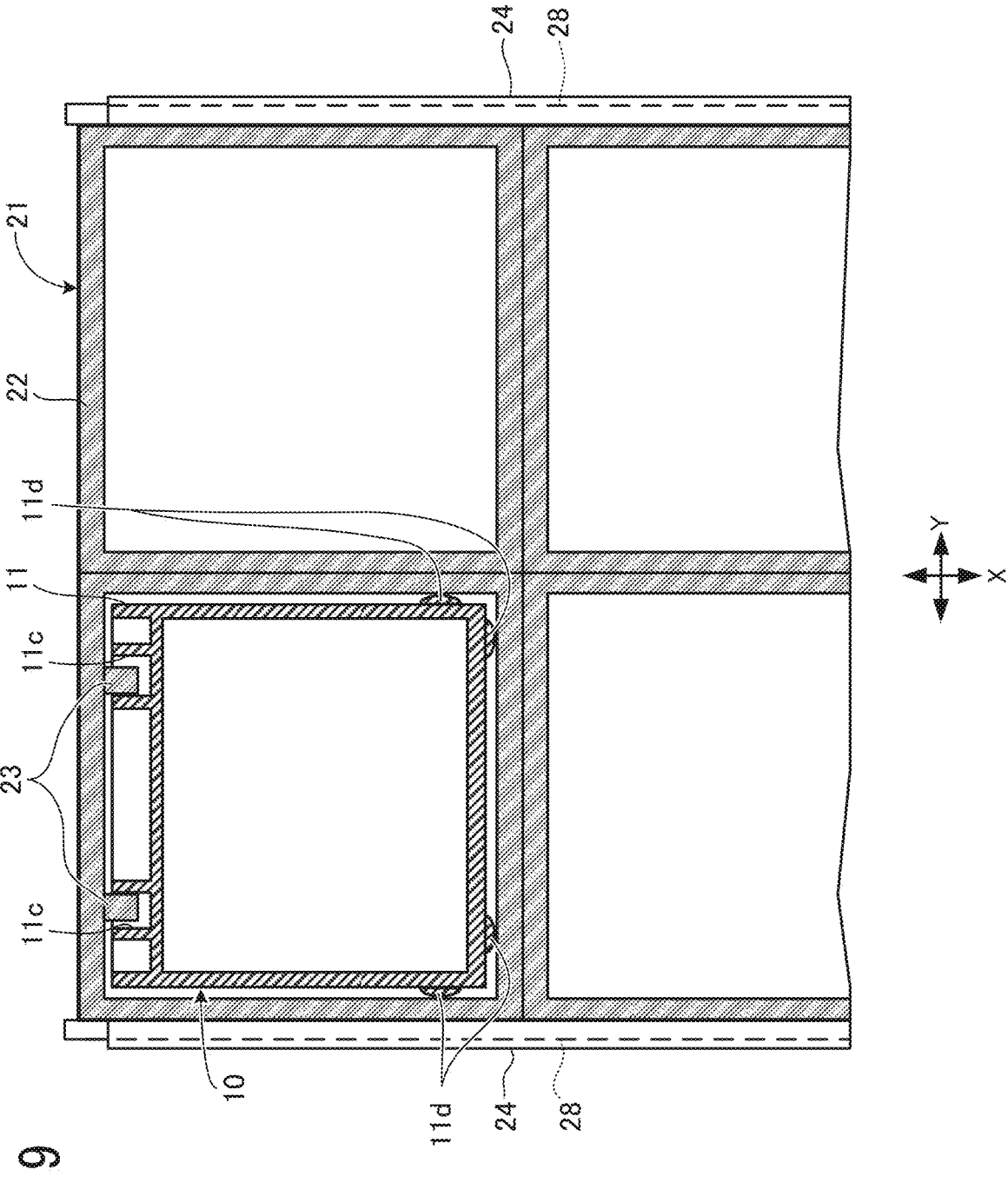
FIG. 9 is a plan cross-sectional view of a main part illustrating an attachment/detachment mechanism of the storage provided in a drawer.
Figure 10:
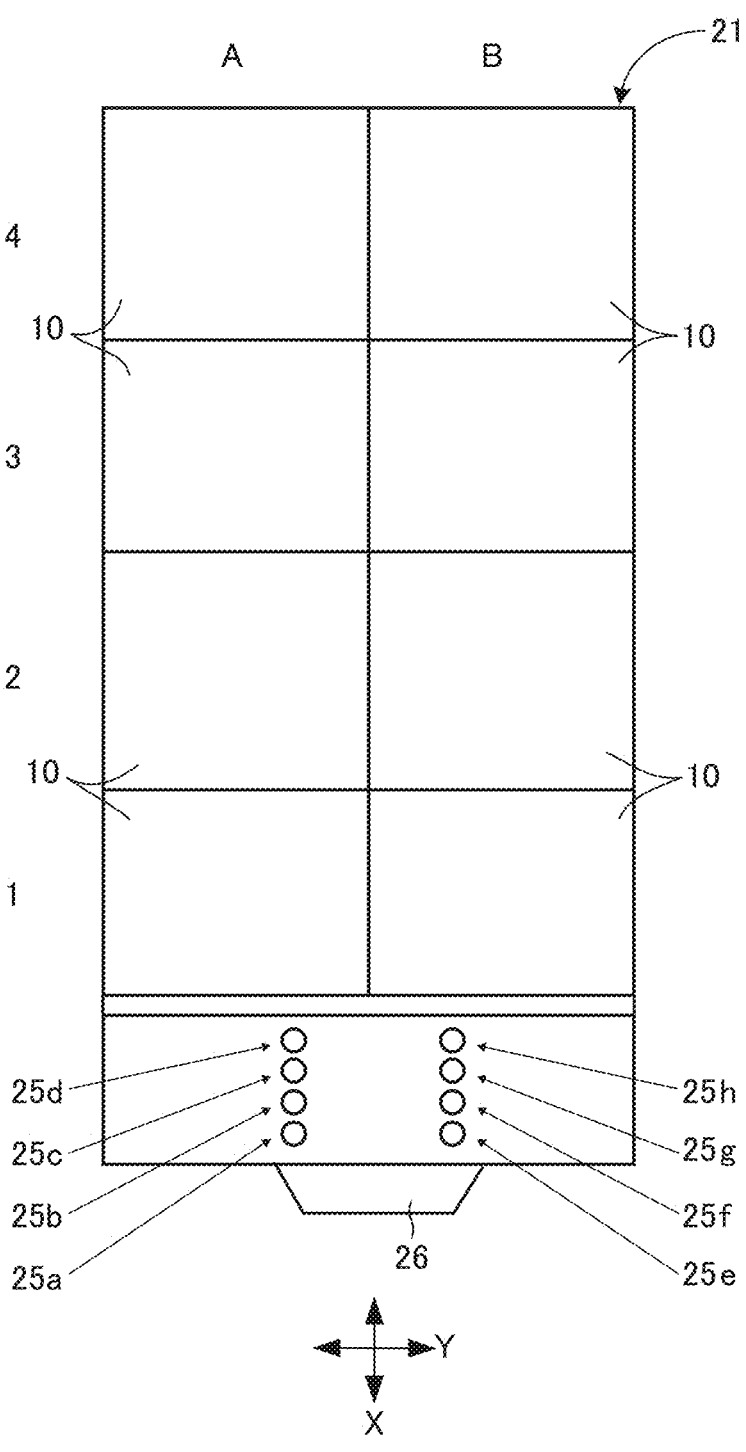
FIG. 10 is a plan view describing a configuration for identification of the storage provided in the drawer.

An attachment/detachment mechanism and operation of the storages provided in the drawer will be described with reference to FIGS. 9 and 10. FIG. 9 is a plan cross-sectional view of a main part illustrating the attachment/detachment mechanism of the storages provided in the drawer, and FIG. 10 is a schematic plan view for explaining an identification configuration of the storages provided in the drawer.

As illustrated in FIG. 9, the drawer 21 is configured to allow a plurality of storages 10 to be attached and detached. The storage 10 configured to be detachable in this manner is also generally called a "cartridge". Slide rails 24 are provided on left and right outer wall surfaces of a case 22 of the drawer 21, and the slide rails 24 are slidable on main body rails 28 disposed on the main body frame 199 (see FIGS. 1A and 1B). Thus, the drawer 21 can be extracted from the inside of the main body frame 199 (see FIGS. 1A and 1B) for attachment and detachment through the engagement between the slide rails 24 and the main body rails 28.

As illustrated in FIG. 9, attachment and detachment of the storage 10 to and from the drawer 21 are performed through engagement and detachment between a pair of convex portions 23 on the inner wall surface of the case 22 of the drawer 21 so as to protrude inward and a pair of concave portions 11*c* on the outer wall portion of the case 11 of the storage 10, and engagement and detachment between the inner wall surface of the case 22 and four hemispherical protrusions 11*d* on the outer wall of the case 11. With the above-described attachable/detachable configuration of the drawer 21, the attachment and detachment operations of the plurality of storages 10 can be easily performed with good operability.

In the above example, the storage 10 is detachably attached through fitting and engagement of the concave and convex portions, but the present disclosure is not limited to this configuration. The same effect as the above can be obtained by providing an elastic material in a gap between the inner wall surface of the case 22 and the outer wall surface of the case 11 or a snap-fit structure.

As illustrated in FIG. 10, the drawer 21 includes guide display portions such as light emitting diodes (LEDs) 25*a* to 25*h* in which installation positions of the plurality of storages 10 can be recognized in the vicinity of a handle 26 to be gripped by hand at the time of performing the attachment and detachment operation. This makes it possible to grasp at a glance where the target storage 10 is in the drawer 21. In the drawing, the LED 25*a* detects the presence or absence of the storage 10 to be attached/detached corresponding to A1 (a portion or a section uniquely determined by a vertical column and a horizontal row) of the drawer 21. Similarly, the LED 25*b*, the LED 25*c*, the LED 25*d*, the LED 25*e*, the LED 25*f*, the LED 25*g*, and the LED 25*h* detect the presence or absence of the storage 10 to be attached and detached, corresponding to a portion A2, a portion A3, a portion A4, a portion B1, a portion B2, a portion B3, and a portion B4 of the drawer 21, respectively.

In the guidance display portions such as the LEDs 25*a* to 25*h*, there is a possibility that a staff member or the like who attaches and detaches the storage 10 may make a mistake. Thus, for example, the presence or absence of the storage 10 may be electronically identified by a sensor, a switch, or the like.

In addition, in order to allow individual storages to be identified, numbers, bar codes, QR codes (registered trademark), contactless integrated circuit (IC) tags, or the like may be included in the storages to cause the system to memorize whose medicine is in which storage. Then, after the drawers to which the storages are attached are set in the apparatus body, and the apparatus body identifies each storage. As a result, the apparatus can pick up the target pack without making a mistake.

A configuration and operation of the extraction device will be described with reference to FIGS. 11A to 13E. FIG. 11A is a front view illustrating a configuration of the extraction device, FIG. 11B is a plan view of the extraction device illustrated in FIG. 11A, and FIGS. 12A to 12F and 13A to 13E are front views illustrating operations of the extraction device.

As illustrated in FIGS. 11A and 11B, the extraction device 50 includes an absorber 51 that extracts the pack 2 from the storage 10, and a holder 61 that holds the extracted pack 2. The absorber 51 includes an air suction pump 48 (not illustrated in FIGS. 11A and 11B, but illustrated in a block diagram of FIG. 17 to be described later), and absorbs the pack 2 in a negative pressure state caused by the suction pump 48.

The suction pump 48 may be disposed in the extraction device 50 or may be disposed at another portion in the medication support apparatus 200. When the suction pump 48 is disposed in the medication support apparatus 200, the absorber 51 is coupled to the suction pump 48 via a communication member such as an air tube.

The absorber 51 includes a pair of absorption pads 52 that communicates with the suction pump and absorbs the pack 2 and are provided in the X direction, an absorption duct 53 coupled to the absorption pads 52, a duct coupling member 54 coupled to the absorption duct 53, and an absorber vertical movement device 55 that moves the absorption pads 52, the absorption duct 53, and the duct coupling member 54, as an integrated component, in the Z direction.

The absorber vertical movement device 55 includes a pair of guide rods 56 provided in the X direction to guide the duct coupling member 54 in the Z direction, an endless belt 59 wound around a driving pulley 57 and a driven pulley 58, and an absorber vertical movement motor 60 coupled to the driving pulley 57 via a drive transmission member such as a gear or a belt. The duct coupling member 54 is coupled and secured to the belt 59 by a belt gripper 59a. The guide rod 56 is secured to a guide rod holding member 50b fastened to n extraction frame 50a that is a main body frame of the extraction device 50. The absorber vertical movement motor 60 is secured to the extraction frame 50a. The absorber vertical movement motor 60 is a control target drive member of the absorber vertical movement device 55 (see FIG. 17 described later).

The holder 61 includes a holding tray 62 that serves as a pedestal for temporarily holding the extracted pack 2, guide rod holding members 65 coupled to both sides of the holding tray 62 in the X direction so that the posture of the holding tray 62 can be changed, a pair of posture deformation assist members 47 that are provided in the X direction to change the posture of the holding tray 62, and a holder vertical movement device 63 that moves the holding tray 62 in the Z direction.

The holding tray 62 has a substantially housing (box) shape in order to temporarily hold the extracted pack 2, and has a recessed shape 62a in order to avoid interference with the integrated component (the absorption pads 52, the absorption duct 53, and the duct coupling member 54) of the absorber 51.

The posture deformation assist members 47 have inclined portions 47a on an upper left side as seen in the drawing.

The holder vertical movement device 63 includes a pair of guide rods 64 that are provided in the X direction to guide the holding tray 62 in the Z direction, an endless belt 68 wound around a driving pulley 66 and a driven pulley 67, and a holder vertical movement motor 69 that is coupled to the driving pulley 66 via a drive transmission member such as a gear or a belt. The holder vertical movement motor 69 is a control target drive member of the holder vertical movement device 63 (see FIG. 17 described later). The guide rod holding member 65 is coupled and secured to the belt 68 by a belt gripper 68a. The holder vertical movement motor 69 is secured to the extraction frame 50a.

The absorber vertical movement device 55 and the holder vertical movement device 63 described above are not limited to the vertical reciprocating mechanisms by belt drive, and may be reciprocating linear motion mechanisms using a rack-and-pinion system or the like.

As illustrated in FIGS. 11A and 11B, the camera 135 is installed near the left end of the holding tray 62 in the extraction device 50. The camera 135 includes a lens 135a for imaging a target subject, and has a function of a pack information reader that reads the medication-related information 6a and 6b (see FIGS. 2A and 2B) and the like added to the pack 2. The camera 135 is electrically coupled to the controller 150 illustrated in FIG. 17 described later via a signal/power cable (not illustrated) or the like. As illustrated in the operation diagram of FIGS. 13A to 13E, the holding tray 62 is movable to change its own posture, but the camera 135 is secured to the extraction frame 50a via a mounting bracket 136 so as to maintain the position not interfering with the holding tray 62. That is, the camera 135 is substantially formed as a part of the extraction device 50.

The lens 135a of the camera 135 is set in a predetermined direction to read the medication-related information 6a, 6b, and the like on the pack 2 placed in the holding tray 62 at least before the pack 2 extracted from the storage 10 moves to a specific position in the medicine delivery tray 30. The camera 135 and the mounting bracket 136 are mounted at predetermined positions illustrated in FIGS. 11A and 11B and are set in predetermined shapes.

An operation of the extraction device 50 will be described with reference to FIGS. 12A to 13E. The operation of the extraction device 50 also includes the reading operation of the medication-related information 6a and 6b on the pack 2 by the camera 135. In the operation diagrams of FIGS. 12A to 13E, in order to simplify the drawings, the illustration of the mounting bracket 136 is omitted, and the camera 135 is intentionally reduced in size as compared with other members such as the pack 2 and the holding tray 62.

The packs 2 in the storage 10 are stacked such that the medication-related information 6a and 6b (see FIG. 3) added to the bag 2a of the pack 2 always faces up to allow the medication-related information 6a, 6b and the like to be read by the camera 135.

As illustrated in FIG. 12A, the extraction device 50 is moved to directly below the storage 10 by the operation of the transfer device 90 in FIGS. 1A and 1B and is in the stopped state. In the operations illustrated in FIGS. 12A to 12E, the absorber vertical movement device 55 indicated by a solid line is in the operating state, and the holder vertical movement device 63 indicated by a broken line is in the stopped state.

At this time, the absorber vertical movement motor 60 of the absorber vertical movement device 55 is stopped, and the absorption pads 52 are positioned in the vicinity of the lower portion of the holding tray 62 in the horizontal state (the initial position of the absorption pads 52). Thereafter, as illustrated in FIG. 12B, the absorption pads 52 are moved upward by the operation of the absorber vertical movement motor 60, enter the storage 10 from the pack extraction opening 17 between the left supporter 12 and the right supporter 13, and comes into contact with the pack 2 located at the lowermost portion of the storage 10 and simultaneously absorbs the pack 2. At this time, the suction pump 48 is driven in advance so that the absorption operation can be performed.

Next, as illustrated in FIG. 12C, the absorption pads 52 are moved downward while absorbing the pack 2 by the reverse rotation operation of the absorber vertical movement motor 60, so that the pack 2 is extracted from the storage 10. The left supporter 12 that opens and closes the pack extraction opening 17 of the storage 10 has a flap shape by the biasing force in a predetermined range of the torsion coil spring (not illustrated) as described above, and the right supporter 13 is formed of an elastic member, so that the supporters are opened and closed by the extraction operation of the absorption pads 52.

Next, as illustrated in FIGS. 12D and 12E, the extracted pack 2 is held by the holding tray 62 in the lateral horizontal state. Thereafter, the absorption pads 52 descend to a position not in contact with the extracted pack 2, that is, a position (initial position) in the vicinity of the lower side of the holding tray 62 in the lateral horizontal state as illustrated in FIG. 12A. At this time, the outer bottom wall surface of the holding tray 62 is in contact with the outer upper wall surface of the posture deformation assist member 47. That is, as illustrated in FIGS. 12A to 12E, the outer bottom wall surface of the holding tray 62 is held in contact with the outer upper wall surface of the posture deformation assist member 47.

Next, as illustrated in FIG. 12F, the absorber 51 and the absorber vertical movement device 55 are brought into a stopped state as indicated by broken lines, and the holder 61 and the holder vertical movement device 63 are brought into an operating state as indicated by solid lines. Hereinafter, the operation illustrated in FIGS. 12F to 13A will be described while providing a supplementary explanation of the mechanism of the holding tray 62 holding the pack 2. The holding tray 62 can rotate by 90 degrees to change the posture of the pack 2 in the holding tray 62 from the horizontal posture to the vertical posture. A coupling portion between the holding tray 62 and the guide rod holding member 65 is rotatable.

As illustrated in FIGS. 12F to 13A, as the belt 68 rotates, the guide rod holding member 65 moves downward in the Z direction along the guide rod 64, and the outer bottom wall surface of the holding tray 62 comes into contact with the inclined portion 47a of the posture deformation assist member 47.

Figures 13A, 13B:
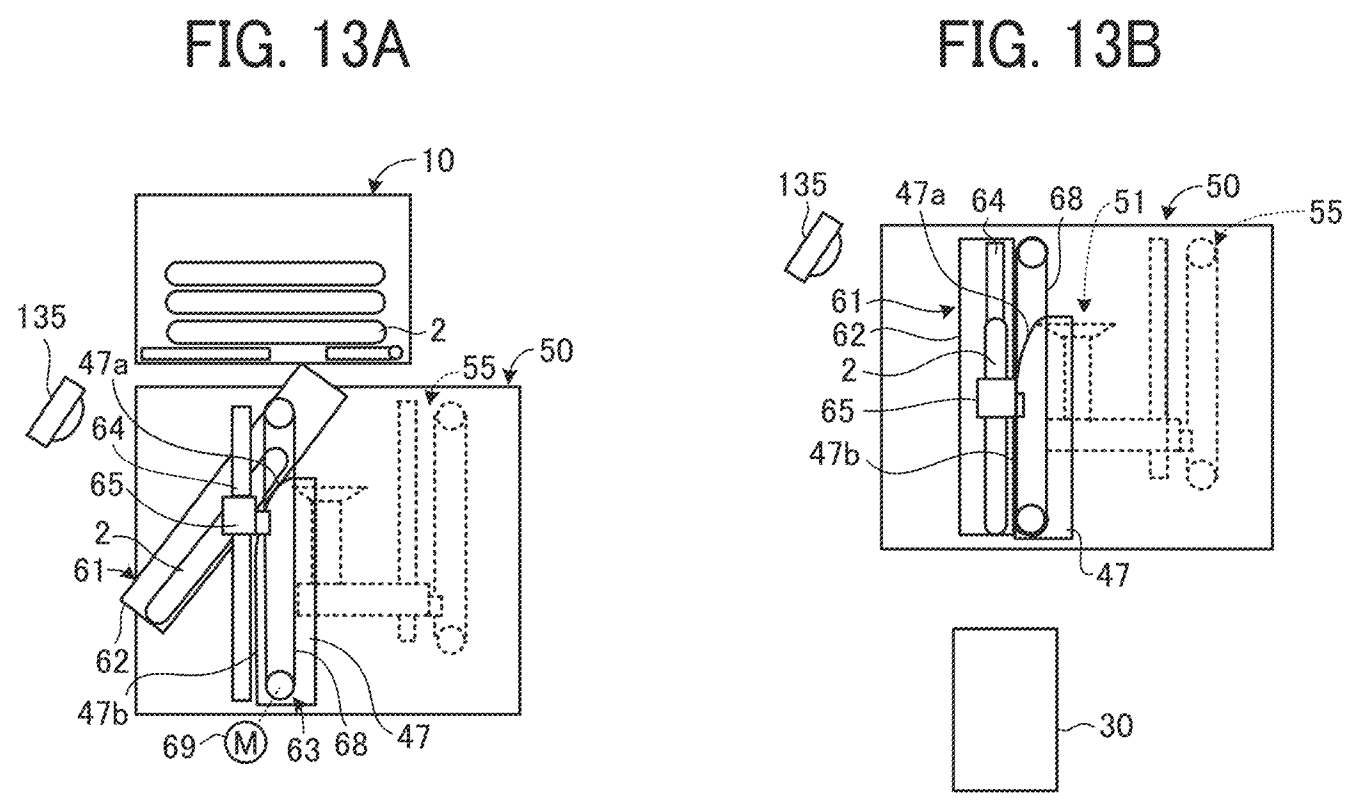

As illustrated in FIG. 13A, the holder vertical movement motor 69 is temporarily stopped so that the inclined state of the holding tray 62 is temporarily maintained. In this way, the medication-related information 6a and 6b added to the pack 2 is imaged by the camera 135 when the pack 2 held in the holding tray 62 is within the imaging range of the camera 135. As described above, the medication-related information 6a and 6b of the pack 2 can be read by the camera 135 such that the posture change of the holding tray 62 is temporarily stopped within the imaging range of the camera 135 during the transition from the state in which the pack 2 is extracted from the storage 10 and held in the holding tray 62 (FIG. 12D) to the state in which the pack 2 in the holding tray 62 is arranged in the medicine delivery tray 30.

If the medication-related information on the pack 2 read by the camera 135 is medication-related information 6a of a character string, the medication-related information 6a is converted into digital data by optical character recognition (OCR) processing, and if the medication-related information on the pack 2 read by the camera 135 is a QR code (registered trademark) such as the medication-related information 6b, the QR code (registered trademark) is read and converted into digital data. In addition, the device for reading the medication-related information (pack information reader) does not need to be the camera 135. If the medication-related information is a barcode, a barcode reader is used, and if the medication information is an RFID tag, an RFID reader is used.

Next, after the reading of the medication-related information 6a and 6b on the pack 2 by the camera 135 is completed, the operation of the holder vertical movement motor 69 kept in the state of FIG. 13A is started again, so that the outer bottom wall surface of the holding tray 62 comes into contact with a vertical portion 47b of the posture deformation assist member 47. As a result, the posture of the holding tray 62 and the posture of the pack 2 held by the holding tray 62 are changed from the oblique posture to the vertical posture. At this time, a biasing force of a spring (not illustrated) acts on the holding tray 62 in a clockwise direction in FIG. 12F so that the holding tray 62 and the pack 2 held by the holding tray 62 are always in the lateral posture.

Next, as illustrated in FIG. 13B, the extraction device 50 including the holding tray 62 in the vertical posture holding the pack 2 is transferred by the transfer device 90 of FIGS. 1A and 1B to the target medicine delivery tray 30 (here, the medicine delivery tray 30 has a single section for simplification of description). Then, as illustrated in FIG. 13C, the posture of the holding tray 62 is changed, and an operation of inserting the pack 2 in the holding tray 62 into the medicine delivery tray 30 is performed.

Next, as illustrated in FIGS. 13C, 13D, and 13E, the holding tray 62 in the holding the pack 2 in the vertical posture moves downward in the Z direction along the guide rod 64 via the guide rod holding member 65 as the belt 68 further rotationally travels. Then, when the holding tray 62 in the vertical posture comes into contact with the upper end portion of the medicine delivery tray 30, a bottom portion 62b of the holding tray 62 is opened in conjunction with the contact, and the pack 2 is moved from the holding tray 62 into the medicine delivery tray 30. As described above, the bottom portion 62b of the holding tray 62 in the vertical posture is opened and closed in conjunction with the downward movement of the holding tray 62 in the Z direction. This operation is performed, for example, by a mechanism in which a convex portion (not illustrated) is provided on the extraction device 50 so as to abut on the bottom portion 62b to open the bottom portion 62b when the holding tray 62 in the vertical posture comes to a specific position.

The convex portion in the extraction device 50 is not necessarily provided within the extraction device 50, and may be partially provided in the medicine delivery tray 30, or an intermediate member (not illustrated) provided between the drawer 21 (see FIGS. 1A, 1B, 10, and the like) and the medicine delivery tray 30 may function as the convex portion.

Next, as illustrated in FIG. 13E, after transfer of the pack 2 from the holding tray 62 into the medicine delivery tray 30, the empty holding tray 62 is moved upward in the Z direction along the guide rod 64 via the guide rod holding member 65 along with the reverse rotational traveling of the belt 68.

As described above, one feature of the extraction device 50 is to extract the pack 2 stored in the storage 10 from under the storage 10. According to this configuration, the next pack 2 left in the storage 10 is moved by its own weight to the pack extraction opening 17 (see FIGS. 7A and 7B) located underneath, so that the extraction device 50 can extract the pack 2 by the same operation regardless of the number of the packs 2 left in the storage 10.

Figures 14A, 14B:
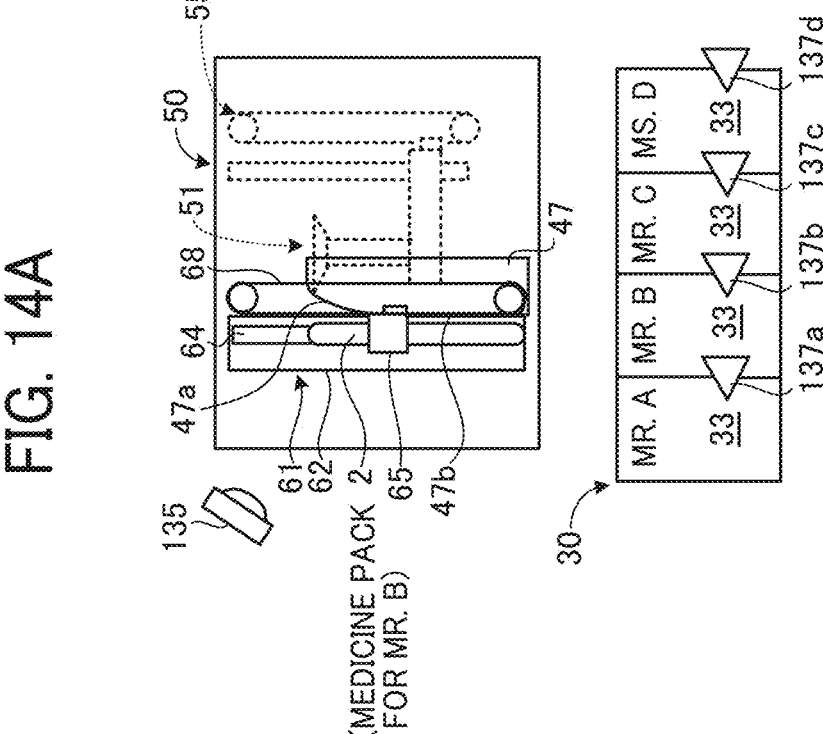
FIG. 14A is a front view illustrating a configuration example and operation of a medicine pack delivery detection sensor that detects medicine delivery processing results.
FIG. 14B is a front view illustrating the configuration example and operation of the medicine pack delivery detection sensor that detects medicine delivery processing results.

With reference to FIGS. 14A and 14B, description is provided as to a configuration example of an optical sensor that detects that a pack is arranged at a specific position in a medicine delivery tray (hereinafter, also referred to as "medicine delivery processing result") and an operation of the optical sensor. FIG. 14A is a diagram illustrating that the extraction device 50 is moved to a specific section in the medicine delivery tray in which optical sensors are arranged in corresponding sections, and FIG. 14B is a diagram illustrating a state in which the optical sensor detects that a pack from the holder of the extraction device 50 is arranged in the specific section in the medicine delivery tray.

In the medicine delivery tray 30 illustrated in FIGS. 14A and 14B, for example, medicine pack delivery detection sensors 137a to 137d as medicine delivery pack detectors for detecting the packs 2 containing the medicine to be taken by medicine recipients are disposed in correspondence with the sections 33 partitioned for four medicine recipients (A, B, C, and D). The medicine pack delivery detection sensors 137a to 137d are, for example, reflective optical sensors.

As illustrated in 14A, the extraction device 50 holds, for example, the pack 2 for B extracted from the storage 10 in a vertical posture on the holding tray 62. The extraction device 50 moves and stops over a designated section in the medicine delivery tray 30, for example, an empty section for B in which the medicine pack delivery detection sensor 137b is arranged.

As described above, the designated section for arranging the medicine pack 2 for B is empty before the delivery process of the medicine pack 2 for B. Thus, it is possible to recognize that the medicine pack delivery is normally completed by confirming that the medicine pack delivery detection sensor 137b detects the pack 2 after the end of the medicine delivery processing. The medicine delivery information management unit 145 (see FIGS. 1A and 1B) is responsible for recognizing the normal completion of the medicine pack delivery.

Figures 15A, 15B:
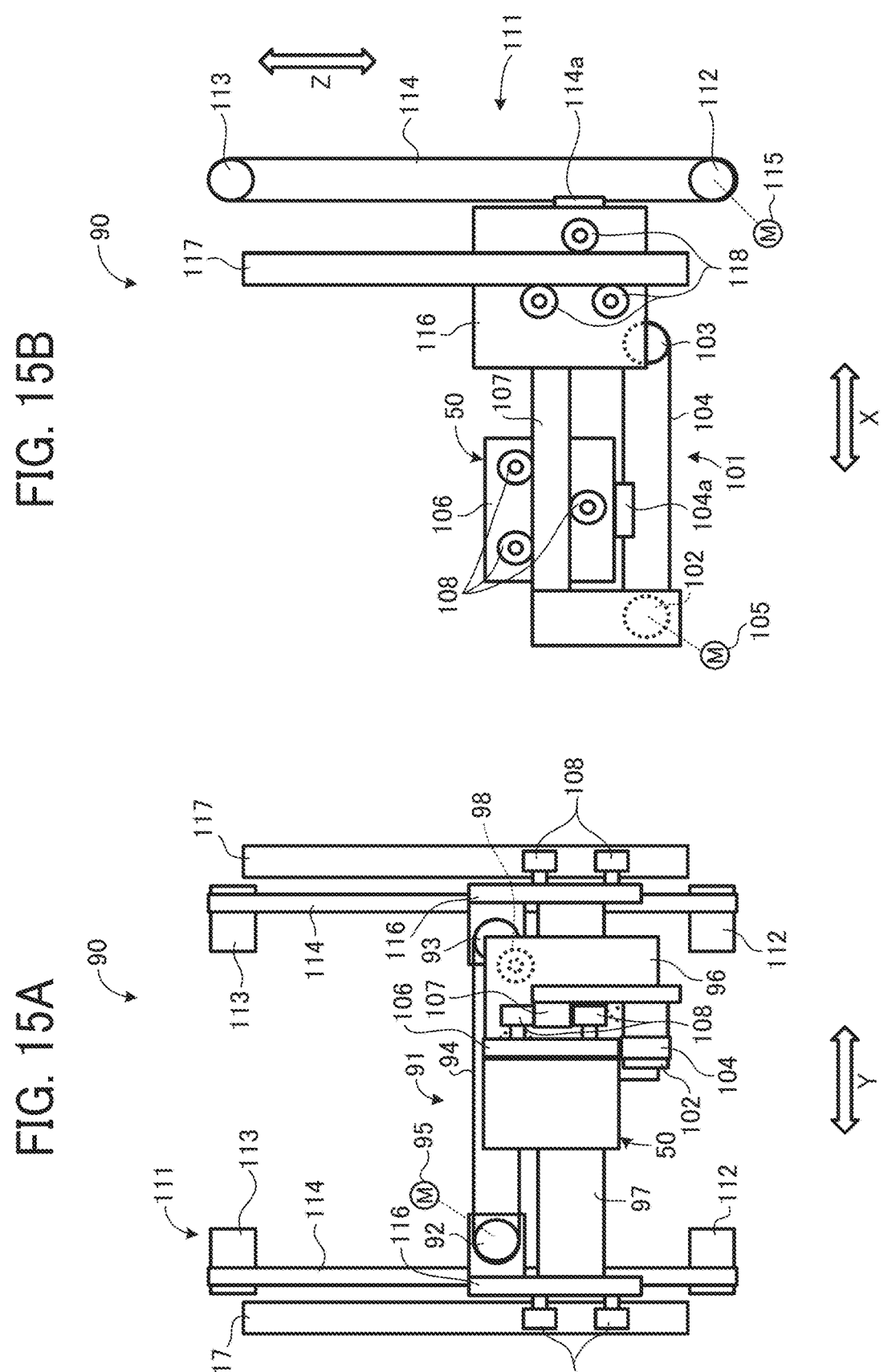
FIG. 15A is a front view illustrating a configuration of a main part of a transfer device.
FIG. 15B is a side view of the main part of a transfer device illustrated in FIG. 15A.

The configuration and operation of the transfer device 90 will be described with reference to FIGS. 15A and 15B. FIG. 15A is a front view of a configuration of a main part of the transfer device, and FIG. 15B is a side view of the main part of the transfer device illustrated in FIG. 15A.

As in the configuration of the medication support apparatus 200 of FIGS. 1A and 1B, the storages 10 are arranged on the planes of the upper and lower portions in the Z direction with the medicine delivery tray 30 in between. The medicine delivery tray 30 is located above the lowermost storage 10, so that the extraction device 50 moves in three directions of front and back/depth (X direction), left and right/horizontal (Y direction), and upper and lower/vertical (Z direction). As described above, the transfer device 90 is configured to move the extraction device 50 in the X direction, the Y direction, and the Z direction in order to transfer the pack 2 extracted from the storage 10 by the extraction device 50 to be delivered to the medicine delivery tray 30.

The component for moving the extraction device 50 in the Y direction is a Y-direction transfer device 91, the component for moving the extraction device 50 in the X direction is an X-direction transfer device 101, and the component for moving the extraction device 50 in the Z direction is a Z-direction transfer device 111, and they have similar configurations.

The Y-direction transfer device 91 includes a Y adapter 96 attached to the extraction device 50, a Y guide member 97 that guides the extraction device 50 in the Y direction via the Y adapter 96, an endless belt 94 wound around a driving pulley 92 and a driven pulley 93, and a Y-direction transfer motor 95 coupled to the driving pulley 92 via a driving force transmission member such as a gear or a belt.

Three rollers 98 (two of the three rollers are hidden behind the extraction device 50 and cannot be seen in the drawing) are rollably attached to the Y adapter 96 in a state of sandwiching the Y guide member 97. The Y adapter 96 is coupled and secured to the endless belt 94 via a belt grip (not illustrated).

According to the above-described configuration of the Y-direction transfer device 91, when the Y-direction transfer motor 95 is driven, the driving force is transmitted to the endless belt 94 via the driving force transmission member and the driving pulley 92, the endless belt 94 rotationally travels, and the extraction device 50 moves in the Y direction along the Y guide member 97 together with the Y adapter 96.

The X-direction transfer device 101 includes an X adapter 106 attached to the extraction device 50, an X guide member 107 that guides the extraction device 50 in the X direction via the X adapter 106, an endless belt 104 wound around a driving pulley 102 and a driven pulley 103, and an X-direction transfer motor 105 coupled to the driving pulley 102 via a driving force transmission member such as a gear or a belt.

Three rollers 108 are rollably attached to the X adapter 106 in a state of sandwiching the X guide member 107. The X adapter 106 is coupled and secured to the endless belt 104 via a belt gripper 104a.

According to the above-described configuration of the X-direction transfer device 101, when the X-direction transfer motor 105 is driven, the driving force is transmitted to the endless belt 104 via the driving force transmission member and the driving pulley 102, the endless belt 104 rotationally travels, and the extraction device 50 moves in the X direction along the X guide member 107 together with the X adapter 106.

The Z-direction transfer device 111 includes a pair of Z adapters 116 attached to both ends in the Y direction of the Y guide member 97, a pair of Z guide members 117 that guides the extraction device 50 in the Z direction via the Y guide member 97 and the pair of Z adapters 116, endless belts 114 wound around a corresponding driving pulley 112 and a corresponding driven pulley 113, and a Z-direction transfer motor 115 coupled to the driving pulley 112 via a driving force transmission member such as a gear or a belt.

In the Z-direction transfer device 111, the driving pulley 112, the driven pulley 113, and the endless belt 114 are provided on both sides in the X direction, but the Z-direction transfer motor 115 is provided on one of the driving pulleys 112.

Three rollers 118 are rollably attached to each of the Z adapters 116 in a state of sandwiching the corresponding Z guide member 117. In addition, each of the Z adapters 116 is coupled and secured to the corresponding endless belt 114 via a corresponding belt gripper 114a.

According to the above-described configuration of the Z-direction transfer device 111, when the Z-direction transfer motor 115 is driven, the driving force is transmitted to the endless belts 114 via the driving force transmission member and the driving pulleys 112, the endless belts 114 rotationally travel, and the extraction device 50 moves in the Z direction along the Z guide members 117 together with the Y guide member 97 and the Z adapters 116.

In FIGS. 15A and 15B, the extraction device 50 moves in the three axial directions of the X axis, the Y axis, and the Z axis. However, for example, if the storage 10 is arranged on the upper side and the medicine delivery tray 30 is arranged on the lower side with the extraction device 50 in between, the extraction device 50 merely needs to move in the front-back/depth direction (X direction) and the left-right/horizontal direction (Y direction). Therefore, the number of movement axes can be reduced by one.

Figure 16:
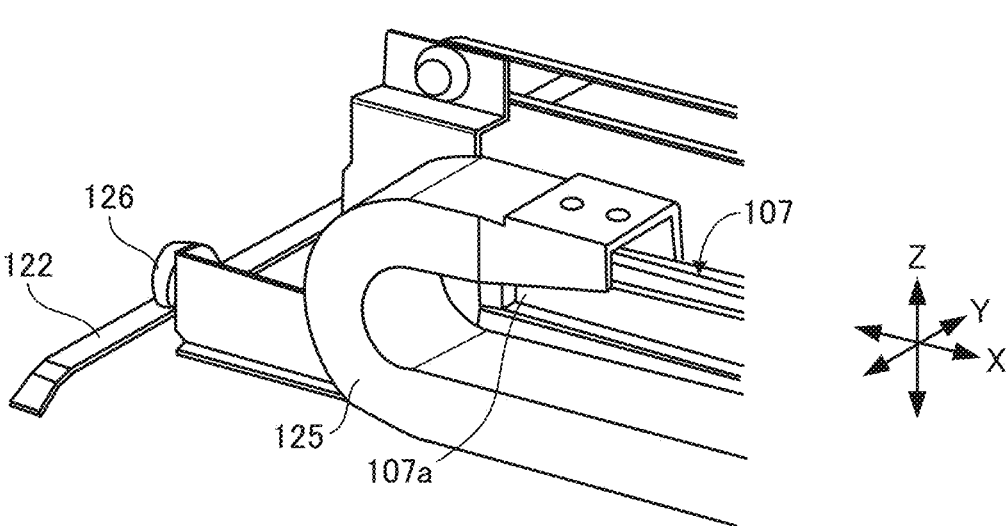
FIG. 16 is a perspective view of a main part illustrating a configuration example of holding the leading end of a Y guide in the transfer device.

In the configuration of the transfer device 90 in FIGS. 15A and 15B, an X-direction distal end of the X guide member 107 is not held. Therefore, as illustrated in FIG. 16, as a holder for a distal end portion 107a of the X guide member 107, a roller 126 may be provided at a distal end portion of a bracket member 125 in which the distal end portion 107a of the X guide member 107 is attached and supported, and the roller 126 may be rollably disposed on a receiving portion 122 provided on the main body frame 199.

According to the above configuration, the distal end portion 107a side of the X guide member 107 can be prevented from being bent by its own weight. This reduces a variation in the distance between the extraction device 50 and the storage 10 or the distance between the extraction device 50 and the medicine delivery tray 30, whereby the pack 2 can be stably extracted and inserted into the medicine delivery tray 30.

A control configuration of the medication support apparatus 200 according to the embodiment of the present disclosure will be described with reference to FIG. 17. A camera 138 surrounded by a broken line in FIG. 17 is not a control target drive member used in the embodiment, but is used in a second modification of the embodiment.

Figure 17:
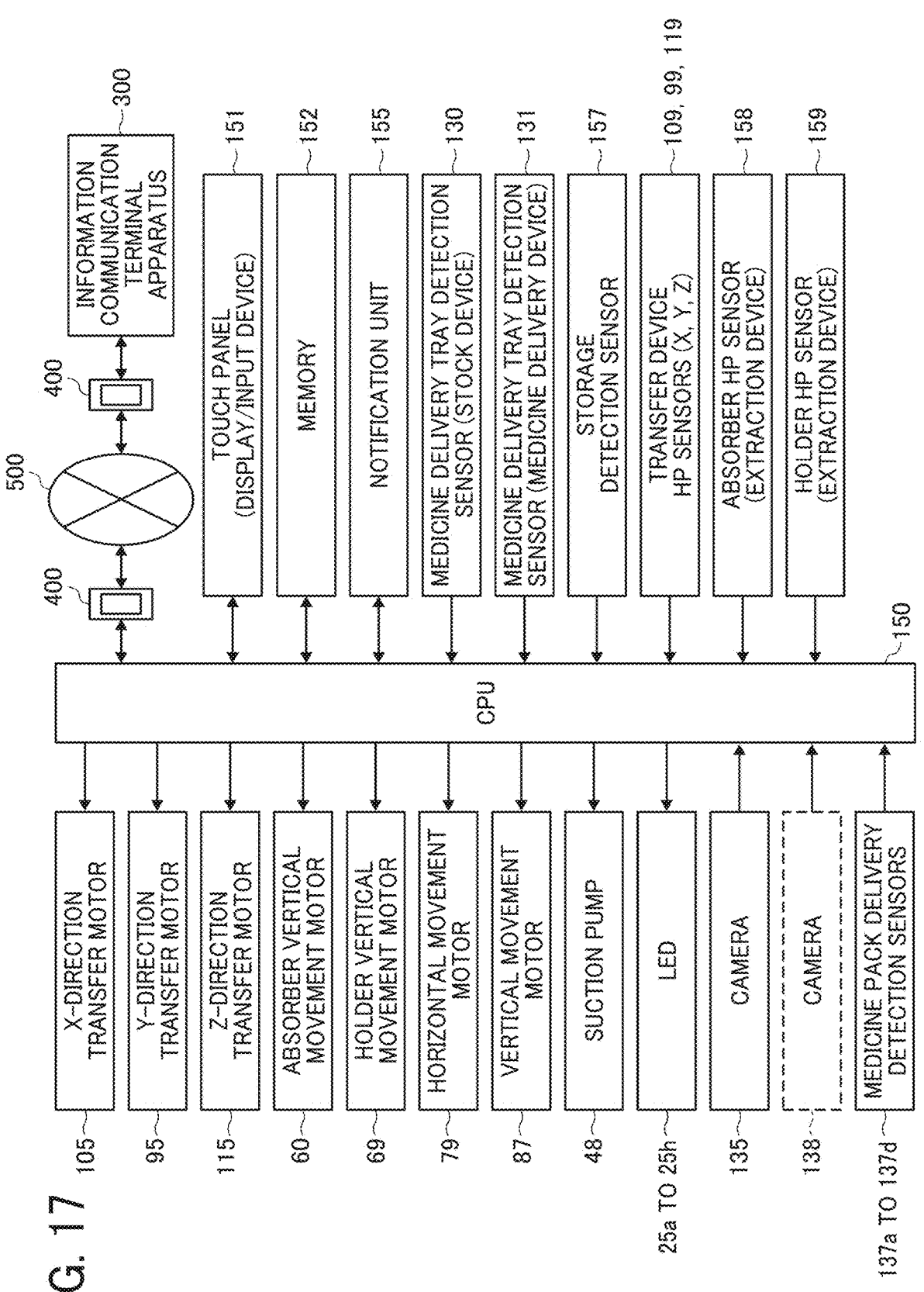
FIG. 17 is a control block diagram illustrating a main control configuration of the medication support apparatus of FIGS. 1A and 1B.

As illustrated in FIG. 17, the medication support apparatus 200 includes a central processing unit (CPU) functioning as the controller 150 that controls the operation of components of the medication support apparatus 200. The CPU incorporates a memory, a timer, and the like. The CPU issues a notification to a user, a staff member, or the like or an instruction for operation of the apparatus at timing according to the program on the basis of various inputs described later.

The pack information management unit 140 and the medicine delivery information management unit 145 constituting the information system device 139 in FIGS. 1A and 1B are configured to include at least the controller 150. Some components of the pack information management unit 140 include the controller 150, a touch panel 151, and the camera 135. Some components of the medicine delivery information management unit 145 include the controller 150, the touch panel 151, and the medicine pack delivery detection sensors 137a to 137d.

The CPU may have a calculation, a control function, and a timer (clocking) function. A memory 152 includes a read-only memory (ROM), a random access memory (RAM), an external memory, and the like. The ROM stores in advance programs (for example, such as a program for a control flowchart described later) readable by the CPU, various kinds of data, and the like. Examples of the data include relationship data handled by the pack information management unit 140 and the medicine delivery information management unit 145, relationship data between the sections 33 in the medicine delivery tray 30 allocated to medicine recipients and the packs 2, relationship data between the sections 33 in the medicine delivery tray 30 allocated by medication timing and the packs 2, relationship data between the sections 33 in the medicine delivery tray 30 allocated in medication order and the packs 2, and the like.

The touch panel 151 and the memory 152 as user interfaces are electrically connected to an input/output port of the CPU via at least one of a signal cable and a power cable. The touch panel 151 is not limited to this, and for example, an input device and a display may be separated from each other and may be a combination of a keyboard and an LED display.

The memory 152 functions as a determination result memory device that records a result of comparison between the first medication-related information and the second medication-related information by the controller 150 (pack information management unit 140) and results of detection by the medicine pack delivery detection sensors 137a to 137d. As above, the detection information of the wrong pack and the information indicating failure of the pack delivery processing to the medicine delivery tray are recorded in the memory 152 so as to be able to be checked later.

A notification device 155 as a notification device that issues a warning or the like to the user is electrically connected to the input/output port of the CPU. The notification device 155 notifies the states of the devices and components by light such as an LED, sound, or vibration. A speaker, a light, and the like are provided for notifying a user, a staff member, and the like of medication timing even if the user, the staff member, and the like are away from the apparatus.

As a specific example of operation of the notification device 155, if a pack 2 extracted from the storage 10 in which a wrong pack has been stored is determined to be a wrong pack again, the extraction of a pack 2 from the storage 10 in which the wrong pack has been stored is stopped, and the notification device 155 issues a warning to the user.

An information communication terminal apparatus 300 owned by a system user of the medication support apparatus 200 is communicably connected to the input/output port of the CPU. The CPU of the medication support apparatus 200 and the information communication terminal apparatus 300 are communicably connected to each other with an information communication unit, which is a network connection device such as routers 400, capable of communication via a network 500 such as the Internet and a local area network (LAN), and error information and the like to be described later is provided from the medication support apparatus 200 to the information communication terminal apparatus 300.

Electrically connected to the input port of the CPU are a medicine delivery tray detection sensor 130 that detects the type of the medicine delivery tray 30 stored in the medicine delivery tray stock device 45, a medicine delivery tray detection sensor 131 that detects whether the medicine delivery tray 30 is located in the medicine delivery unit 29, and a storage detection sensor 157 that detects the presence or absence of the pack 2 in the storage 10.

In addition, electrically connected to the input port of the CPU are a transfer device HP sensor 99 that detects a home position (hereinafter, abbreviated as "HP") of the Y-direction transfer device 91 in the extraction device 50, a transfer device HP sensor 109 that detects an HP of the X-direction transfer device 101 in the extraction device 50, and a transfer device HP sensor 119 that detects an HP of the Z-direction transfer device 111 in the extraction device 50.

Also electrically connected to the input port of the CPU are an absorber HP sensor 158 that detects an HP of the absorber 51 (in particular, the absorption pad 52) in the extraction device 50, and a holder HP sensor 159 that detects an HP of the holder 61 (in particular, the holding tray 62) in the extraction device 50.

Electrically connected to the input port of the CPU are the camera 135 and the medicine pack delivery detection sensors 137a to 137d via harnesses (signal cables or the like) (not illustrated).

Electrically connected to the output port of the CPU are LEDs 21a to 25h of the drawer 21, the suction pump 48, the horizontal movement motor 79 of the medicine delivery tray horizontal movement section 70, the vertical movement motor 87 of the medicine delivery tray vertical movement section 82, the absorber vertical movement motor 60, the holder vertical movement motor 69, the Y-direction transfer motor 95 of the Y-direction transfer device 91, the X-direction transfer motor 105 of the X-direction transfer device 101, and the Z-direction transfer motor 115 of the Z-direction transfer device 111.

When input information from the touch panel 151 and various signals from various sensors are input to the CPU, the CPU outputs a next command signal. That is, the CPU outputs a command signal that is an instruction for controlling the sound device and the light device of the display device (including the notification device) of the touch panel 151, the LEDs 25a to 25h, the suction pump 48, the horizontal movement motor 79, the vertical movement motor 87, the absorber vertical movement motor 60, the holder vertical movement motor 69, the Y-direction transfer motor 95, the X-direction transfer motor 105, the Z-direction transfer motor 115, and the notification device 155.

The CPU has a function of executing control operations in control flowcharts to be described later, and an example of a main control operation in the present embodiment is as follows.

The CPU (pack information management unit 140) has a function of comparing the first medication-related information read by the camera 135 with the second medication-related information managed by the CPU to determine whether there is a match between the first and second medication-related information.

The CPU (pack information management unit 140) has a function of, if there is a match between the first and second medication-related information, causing the extraction device 50 and the transfer device 90 to transfer the pack 2 to the medicine delivery tray 30, and if there is no match, determining that the pack 2 extracted from the storage 10 is a wrong pack and causing the extraction device 50 and the transfer device 90 to transfer the wrong pack to the wrong pack depository 40.

The CPU (pack information management unit 140) has a function of, after the transfer of the wrong pack to the wrong pack depository 40, causing the extraction device 50 to extract a pack again from the storage 10 in which the wrong pack has been stored and causing the transfer device 90 to transfer the pack extracted from the storage 10 again to a specific position in the medicine delivery tray 30.

The CPU (medicine delivery information management unit 145) has a function of determining that the pack has been arranged at a specific position in the medicine delivery tray, based on results of the detection by the medicine pack delivery detection sensors 137a to 137d.

The CPU (pack information management unit 140) has a function of, if the pack extracted again from the storage 10 in which the wrong pack has been stored is also determined as a wrong pack, stopping the extraction of a pack from the storage 10 in which the wrong pack has been stored, and causing the touch panel 151 or the notification device 155 to issue a warning to the user or the like.

Figure 18:
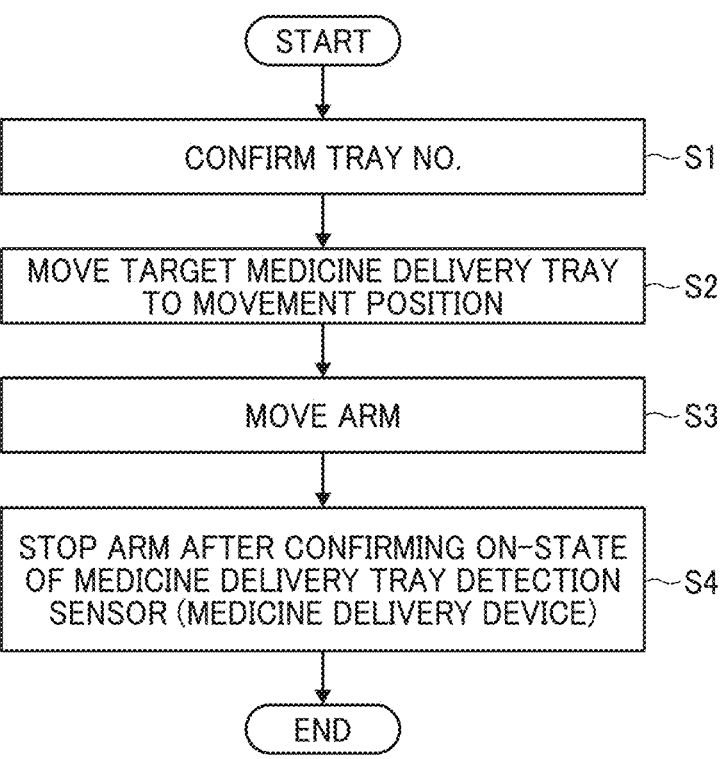
FIG. 18 is a flowchart describing an operation flow of extracting a target medicine delivery tray from the medicine delivery tray stock device.

An operation flow of extracting the target medicine delivery tray 30 from the medicine delivery tray stock device 45 (see FIGS. 5A and 5B) will be described with reference to a flowchart illustrated in FIG. 18.

First, in step S1, No. of the target medicine delivery tray 30 to be extracted from the medicine delivery tray stock device 45 is confirmed. Next, the target medicine delivery tray 30 is moved to a predetermined movement position on the bottom plate 39 of the medicine delivery unit 29. At this time, the horizontal movement motor 79 is driven to move the target medicine delivery tray 30 sandwiched between the pair of arms 71a and 71b (steps S2 and S3). Next, when the medicine delivery tray detection sensor 131 of the medicine delivery unit 29 is turned on and it is determined that the target medicine delivery tray 30 is placed at the movement position, the driving of the horizontal movement motor 79 is stopped. As a result, the movement of the pair of arms 71a and 71b is stopped (step S4).

Figure 19:
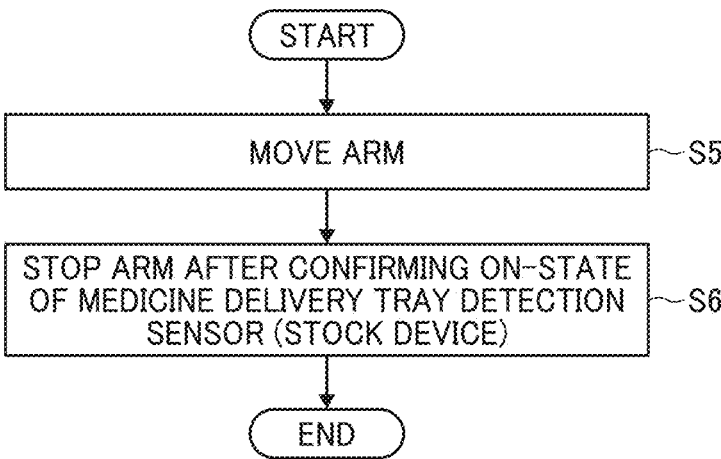
FIG. 19 is a flowchart illustrating an operation flow of returning the medicine delivery tray in a medicine delivery unit to the medicine delivery tray stock device.

An operation flow of returning the medicine delivery tray 30 from the medicine delivery unit 29 to the medicine delivery tray stock device 45 (see FIGS. 4A and 4B) will be described with reference to a flowchart illustrated in FIG. 19.

The horizontal movement motor 79 is driven to move the medicine delivery tray 30 from the medicine delivery unit 29 sandwiched between the pair of arms 71a and 71b to the medicine delivery tray stock device 45 (described as arm movement in step S5). Then, when it is confirmed that the medicine delivery tray detection sensor 130 of the medicine delivery tray stock device 45 is turned on and it is determined that the target medicine delivery tray 30 has been moved onto the medicine delivery tray stock device bottom plate 46 of the medicine delivery tray stock device 45, the driving of the horizontal movement motor 79 is stopped. As a result, the movement of the pair of arms 71a and 71b is stopped (step S6).

The main overall operation of the medication support apparatus will be described with reference to FIG. 20A1 to 20C. This operation is executed under a control command from the CPU of the controller 150.

As illustrated in FIGS. 20A1, 20A2, and 20A3, the extraction device 50 performs an operation of extracting the pack 2 from the lower side of the storage 10. This operation is as described in detail with reference to FIGS. 12A to 12E. When a pack 2 is extracted from the lower side of the storage 10, the next pack 2 moves downward (toward the pack extraction opening 17). Accordingly, the extraction device 50 can perform the same operation regardless of the number of the packs 2 left in the storage 10.

After the pack 2 extracted from the storage 10 is received by the holding tray 62, the pack 2 is held in the holding tray 62 of the extraction device 50 in the posture illustrated in FIG. 20B by the posture change operation of the holding tray 62 similar to that described with reference to FIGS. 12F to 13B. Then, as illustrated in FIG. 20B, the extraction device 50 with the pack 2 held in the holding tray 62 is transferred by the transfer device 90 to the medicine delivery unit 29 where the medicine delivery tray 30 is installed. When the extraction device 50 is conveyed to substantially directly above the medicine delivery tray 30 in the medicine delivery unit 29, the pack 2 is inserted into a predetermined section 33 at a predetermined position in the medicine delivery tray 30 by the operation described with reference to FIGS. 13C, 13D, and 13E.

After the above operation is performed a plurality of times and the necessary packs 2 are inserted into the predetermined sections 33 in the medicine delivery tray 30, the medicine delivery tray 30 is discharged to the outside of the apparatus through the second inlet/outlet 42, for example, as illustrated in FIG. 20C, and is received by a user (including a staff member or a medication assistant) in a nursing home or the like.

Figure 21:
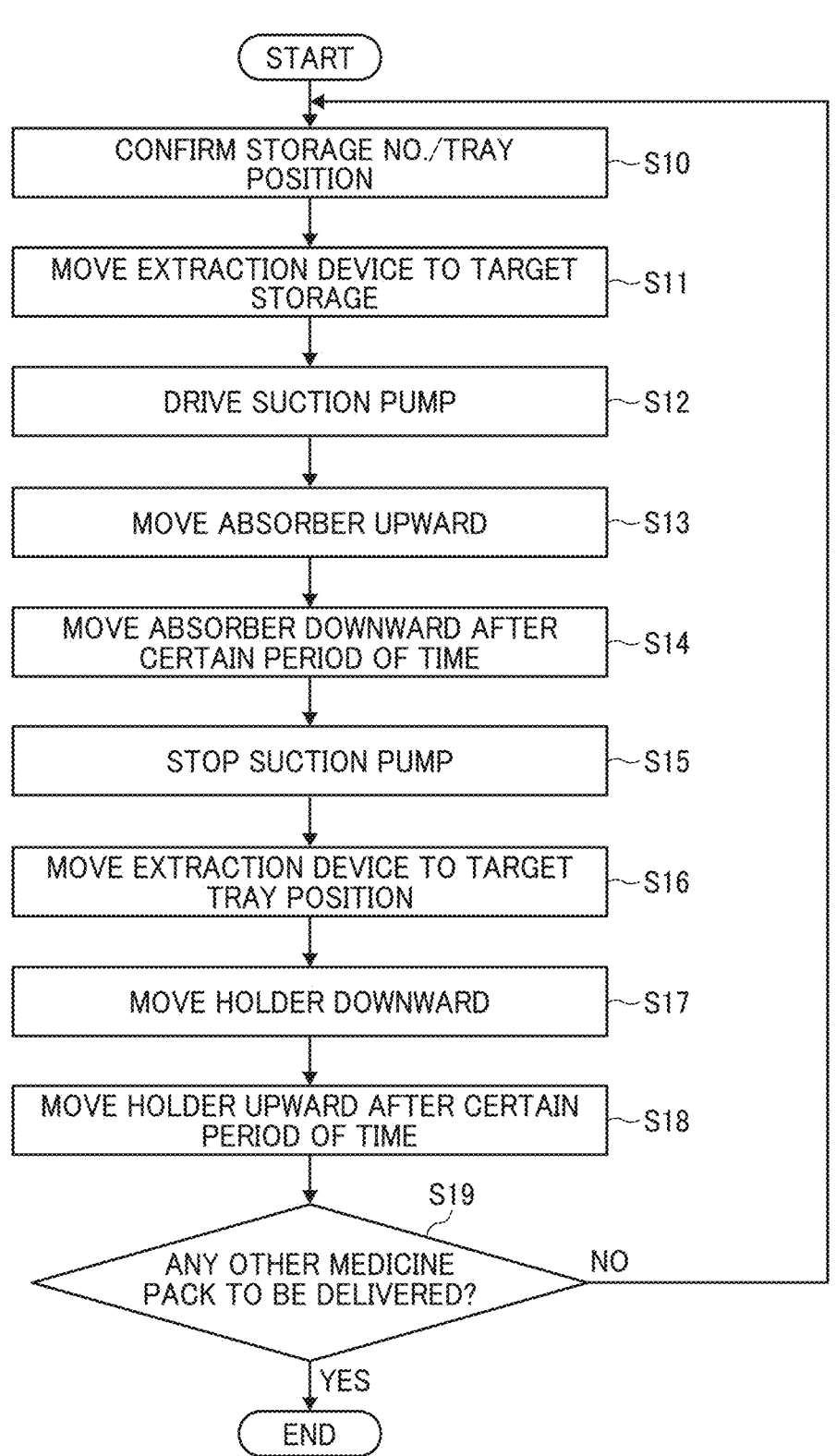
FIG. 21 is a flowchart illustrating an operation flow of the extraction device.

The operation flow of the extraction device in FIG. 20A1 to 20C will be supplemented with reference to FIG. 21. FIG. 21 is a flowchart illustrating an operation flow of the extraction device.

In step S10 of FIG. 21, No. of the target storage 10 storing the packs 2 to be delivered is confirmed, and the position of the target medicine delivery tray 30 into which the packs 2 are inserted and delivered is confirmed.

Then, the extraction device 50 is moved to the target storage 10 by the transfer operation of the transfer device 90

(step S11). Subsequently, the absorber 51 is moved upward by driving the absorber vertical movement motor 60 while driving the suction pump 48 (steps S12 and S13). After a certain period of time in which the lowermost pack 2 in the storage 10 is absorbed and held by the absorption pads 52, the absorber 51 is moved downward by reversely driving the absorber vertical movement motor 60. Thereafter, the suction pump 48 is stopped (steps S14 and S15).

Then, the extraction device 50 is moved to the position of the target medicine delivery tray 30 by the transfer operation of the transfer device 90. When the extraction device 50 is moved to the position of the target medicine delivery tray 30, the holder 61 is moved downward by driving the holder vertical movement motor 69 (steps S16 and S17). After a certain period of time necessary for the holder 61 to be moved downward and the packs 2 in the holding tray 62 to be inserted into and delivered to the predetermined sections 33 in the medicine delivery tray 30, the holder 61 is moved upward by reversely driving the holder vertical movement motor 69 (step S18). Then, it is checked whether there is no other pack 2 to be delivered, and when there is no other pack 2 to be delivered, a series of steps in the operation flow is terminated (step S19).

On the other hand, when it is determined there is another pack 2 to be delivered in step S19, the process returns to step S10, and the same operation as described above is repeated.

A selection display screen (hereinafter, simply abbreviated as a "screen") and the medication-related information (storage, medicine delivery tray, storage/medicine delivery tray) on the touch panel 151 will be described with reference to FIGS. 22 to 33.

FIGS. 22 to 33 illustrate screen displays on the touch panel 151 for indicating the second medication-related information managed by the pack information management unit 140 of the information system device 139 in the medication support apparatus 200 and the position information of the pack extracted from the storage and placed in the medicine delivery tray, which is managed by the medicine delivery information management unit 145.

The information on a resident (medicine recipient) related to the second medication-related information includes a name, a room number, a type of pack (type of medicine), medication timing (morning, daytime, evening, before going to bed, or the like), additional medicine, and deleted medicine. These pieces of information are registered in advance in the medication support apparatus 200 or the control system. An example of screen displays on the touch panel 151 for this registration is illustrated in FIGS. 22 to 33.

Figure 22:
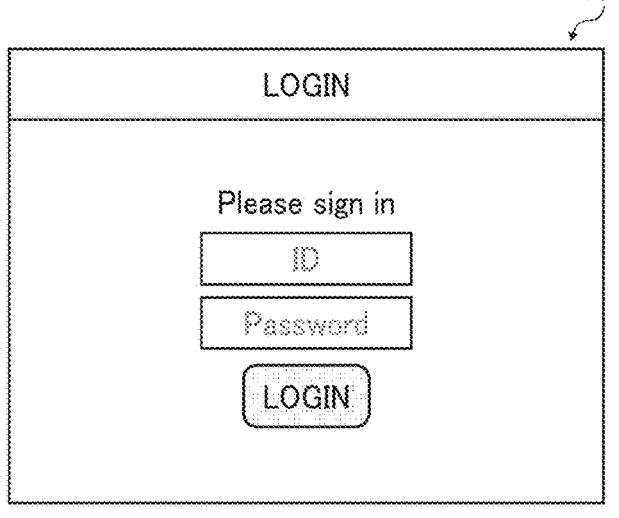
FIG. 22 is a diagram illustrating an initial screen displayed on a touch panel.

FIG. 22 illustrates an initial screen displayed on the touch panel 151 after the medication support apparatus 200 is powered on. FIG. 22 and the subsequent drawings illustrate selection screen displays (hereinafter, simply abbreviated as "screen") on the touch panel 151 for explaining, as needed, the second medication-related information managed by the pack information management unit 140 in the medication support apparatus 200 and the position information of the pack extracted from the storage and placed in the medicine delivery tray, which is managed by the medicine delivery information management unit 145.

Figure 23:
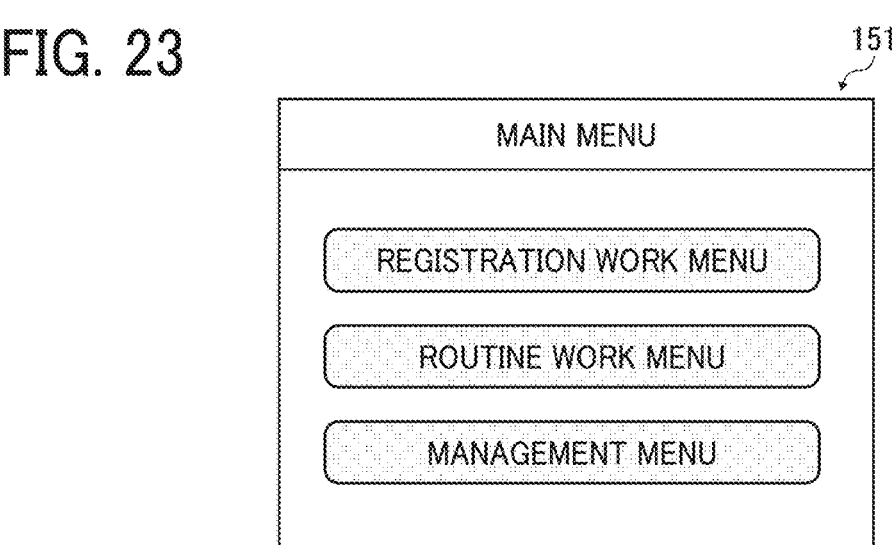
FIG. 23 is a diagram illustrating a "Main Menu" screen displayed on the touch panel.

When "Login" button displayed in gray is touched in the initial screen displayed on the touch panel 151 of FIG. 22, the screen moves to "Main menu" screen illustrated in FIG. 23. When "Registration Work Menu" button is touched in the "Main Menu" screen of FIG. 23, the screen moves to "Registration Work Menu" screen illustrated in FIG. 24. The "Registration Work Menu" screen includes buttons of "New Registration", "Change/Deletion", and "Confirmation of Registration Information". It is possible to change/delete registration information described later and confirm the registration information as appropriate by using the "Change/Deletion" and "Confirmation of Registration Information" buttons as appropriate.

Figure 24:
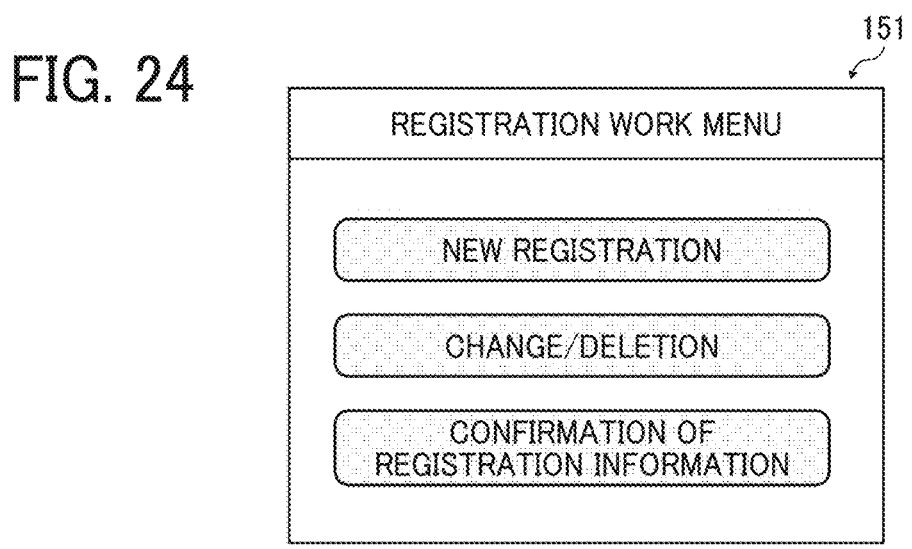
FIG. 24 is a diagram illustrating a "Registration Menu" screen displayed on the touch panel.

When the "New Registration" button illustrated in FIG. 24 is selected, the screen moves to "Basic Information" screen illustrated in FIG. 25, where the detailed information such as the name, room number, and age as the basic information of the resident can be registered. In addition, on "Medication Information" screen in FIG. 26, it is possible to register the details of a pack (medicine) to be taken by the resident as the second medication-related information. Specifically, as an example, a pack No. (1) (in FIG. 26 and the like, numeric characters with circles are used, and the same applies hereinafter) containing two tablets of medicine A and one capsule of medicine B is registered as medicine to be taken by the resident A.

Figure 27:
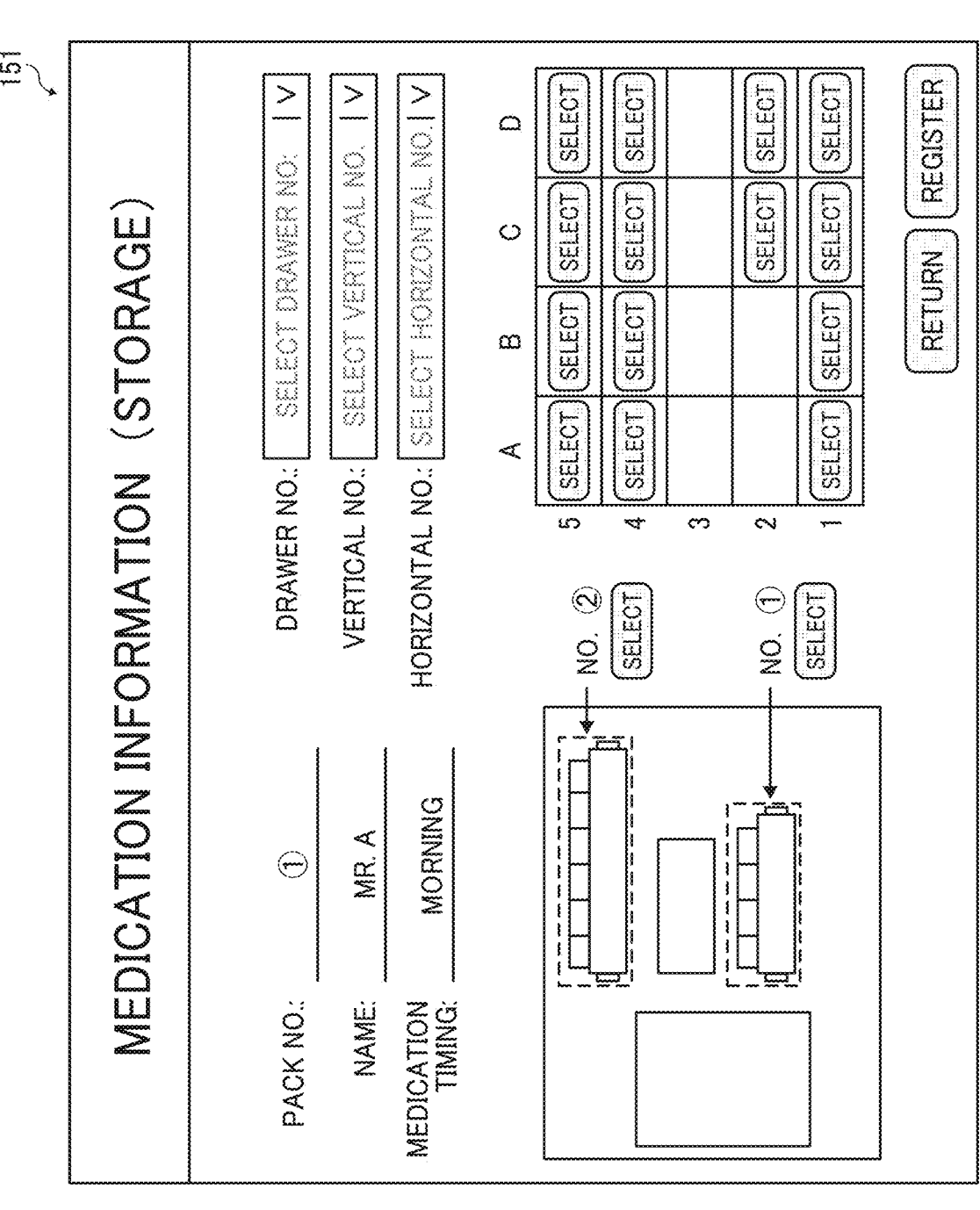
FIG. 27 is a diagram illustrating a "medication information (storage)" screen displayed on the touch panel.

As illustrated in FIG. 27, the pack information management unit 140 manages the information (second medication-related information) on the name of the user, the medication timing, and the place where the storage is stored (drawer No./vertical No./horizontal No.) for each storage.

On "Medication Information (Storage)" screen in FIG. 27, it is possible to select, as the storage 10 that stores the pack No. (1) to be taken by A at the medication timing in the morning registered as illustrated in FIG. 26, either one of the drawer 21 No. (1) (in FIG. 27 and the like, numeric characters with circles are used, and the same applies hereinafter) illustrated in the lower part of FIGS. 1A and 1B or the drawer 21 No. (2) arranged in the upper part of FIGS. 1A and 1B.

It is possible to determine that the pack is correct by comparing the medication-related information (first medication-related information) added to the pack extracted from the storage at the time of the medicine delivery processing with the information (second medication-related information) managed by the pack information management unit 140 (refer to the description with reference to FIG. 13A and the like).

As illustrated in FIG. 28, for the medicine delivery tray prepared in accordance with the medication timing, the medicine delivery information management unit 145 manages information on whose pack is to be arranged in which section (tray No./vertical No./horizontal No.). At the time of medicine delivery work, the pack extracted from the storage is subjected to the medicine delivery processing according to the information on the section in which the pack is to be arranged managed by the medicine delivery information management unit 145, and the success or failure of medicine delivery can be determined by the medicine pack delivery detector (for example, the medicine pack delivery detection sensors 137a to 137d illustrated in FIGS. 14A and 14B).

As in "Medication Information (Medicine Delivery Tray)" screen illustrated in FIG. 28, medicine position information indicating a predetermined section in the medicine delivery tray in which the pack is to be placed is also included in advance in the resident information. As in "Medication Information" screen illustrated in FIG. 29, numbers, barcodes/QR codes (registered trademark), contactless IC tags, and the like are provided for the storages so that each storage can be recognized. At the time of arranging a pack into a storage, the storage No. and the resident information (what medicine to be taken by whom at what time) are associated with each other On the "Medication Information" screen illustrated in FIG. 29, with regard to the pack No. 1 to be taken by A, the storage provided at a position with vertical No. A and horizontal No. 1 in the drawer No. (1) is set, and a predetermined section provided in tray No. A (morning) at a position with vertical No. A and horizontal No. 1 is set.

Then, on "Medication Information" screen illustrated in FIG. 30, "Registration OK" appears to confirm that the registration information described above can be registered.

It is possible to return to the "Registration Work Menu" screen in FIG. 24 by touching the "Return" button as necessary. Then, by touching the "Confirmation of Registration Information" button in FIG. 24, a table of medication timing can be created on the basis of the setting information described above on the "Confirmation of Registration Information (Storage/Tray)" screen illustrated in FIG. 31 and the "Confirmation of Registration Information (Medication Timing)" screen illustrated in FIG. 32.

FIG. 31 is a diagram for describing screen display of the touch panel 151 indicating the medication management information ("Confirmation of Registration Information (Storage/Tray)") managed by the pack information management unit 140 and the medicine delivery information management unit 145. As illustrated in the drawing, arrangement information of the storages and the medicine delivery trays for a plurality of persons is managed. That is, one medication support apparatus 200 can collectively manage medication information of a plurality of medicine recipients.

Accordingly, for example, at the time of preparing a morning medicine delivery tray, it is possible to recognize that the pack to be taken by A in the morning is to be transferred from the storage No. (1)-A-1 to the medicine delivery tray No. A (morning)-A-1, and the pack to be taken by B in the morning is to be transferred from the storage No. (1)-B-1 to the medicine delivery tray No. A (morning)-A-2. By repeating these operations, the morning medicine delivery tray 30 is completed.

The completed medicine delivery tray 30 is temporarily returned to the medicine delivery tray stock device 45 (see FIGS. 1A and 1B), and can be stored until the time when the staff member or the like takes out the medicine delivery tray. At that time, preparation of the subsequent medicine delivery trays 30 for the daytime and afterward may be started. In this manner, preparing the medicine delivery tray 30 in advance makes it possible to smoothly provide medication assistance to the residents, and it is possible to check in advance (whether the medicine is suitable for the states of the residents at that time).

The "Change/Deletion" screen illustrated in FIG. 33 is intended to change or delete the "Confirmation of Registration Information (Medication Timing)" illustrated in FIG. 32.

Figure 34A:
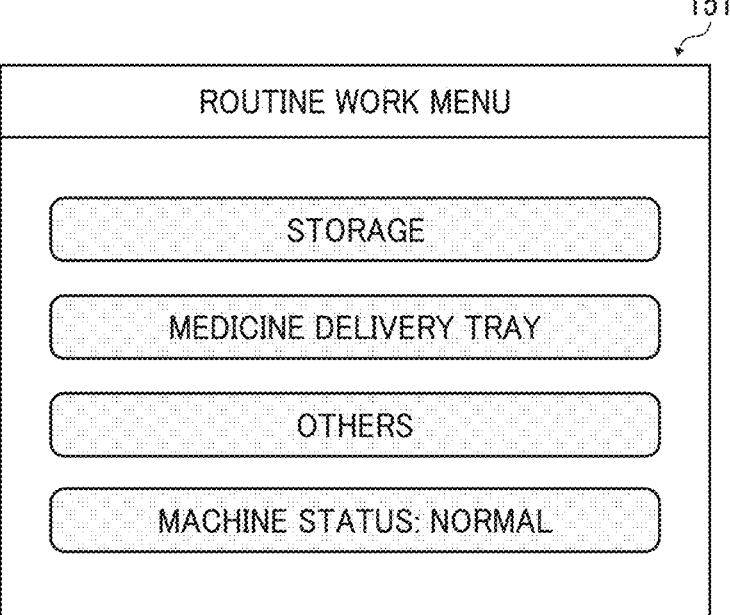
FIG. 34A is a screen displayed on the touch panel when an error occurs in the extraction of a pack or the medicine delivery processing.
Figure 34B:
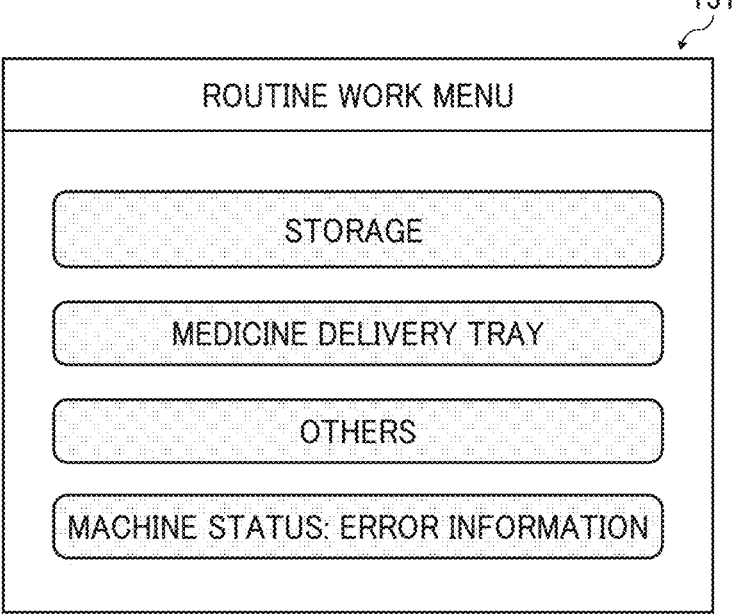
FIG. 34B is a screen displayed on the touch panel when an error occurs in the extraction of a pack or the medicine delivery processing.

With reference to FIGS. 34A to 34C, a method for checking an error in the pack extraction or the medicine delivery processing will be described. FIGS. 34A to 34B are screens displayed on the touch panel when an error occurs in the pack extraction or the medicine delivery processing. The screen on the touch panel 151 illustrated in FIG. 34A is displayed when the pack extraction, the medicine delivery processing, and the like are normally performed. If an error has occurred in the pack extraction, the medicine delivery processing, or the like, the occurrence of an error is indicated on the screen of the touch panel 151 in the information system device 139 (see FIGS. 1A and 1B) as illustrated in FIGS. 34B and 34C, and information including error details and an error history is managed Based on the error information displayed on the screen of the touch panel 151, the user can remove the wrong pack, re-execute the medicine delivery processing, and the like.

Figure 35:
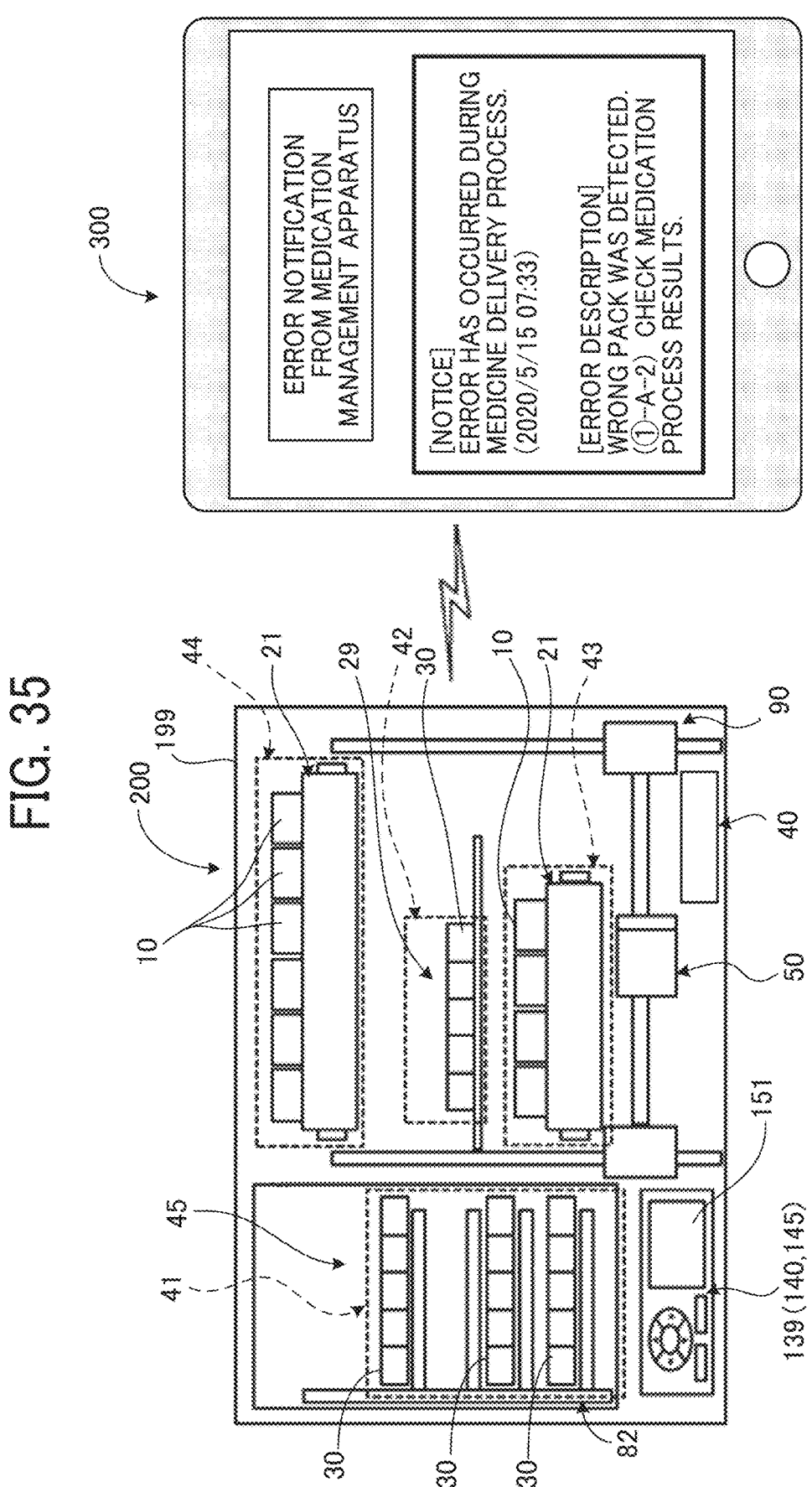
FIG. 35 is a conceptual diagram when the medication support apparatus provides information to an information terminal device.

Information provided from the medication support apparatus to an information communication terminal device will be described with reference to FIG. 35. FIG. 35 is a conceptual diagram of provision of information from the medication support apparatus to the information terminal device.

Referring to FIG. 35, the medication support apparatus 200 (in particular, the CPU illustrated in FIG. 17) is communicably connected to the information communication terminal apparatus 300 via an information communication unit, which is a network connection device such as the routers 400 (illustrated in FIG. 17), capable of communication via a network 500 such as the Internet and a LAN. The information communication terminal apparatus 300 is, for example, a movable information communication terminal owned by a system user. By setting the information communication terminal apparatus 300 as notification destination in the medication support apparatus 200, it is possible to notify the information communication terminal apparatus 300 of the state of the medication support apparatus 200.

The information to be provided from the medication support apparatus 200 to the information communication terminal apparatus 300 includes at least one of detection information indicating that the pack extracted from the storage is a wrong pack and information indicating that the medicine delivery processing of the pack to the medicine delivery tray has failed.

For example, as illustrated in FIG. 35, in the event of occurrence of an error during the medicine delivery processing, the outline and detailed information of the error similar to the information illustrated in FIG. 34C is provided to the information communication terminal apparatus 300 so that it is possible to quickly take measures at the occurrence of the error.

The information to be provided from the medication support apparatus 200 to the information communication terminal apparatus 300 may be not only the error information as described above but also information indicating that the medicine delivery processing has been normally completed or that the packs in the storage have run out.

According to the configuration illustrated in FIG. 35, the details of error information at the time of preparing the medicine delivery tray can be acquired at any time. This saves recovery work time and unnecessary time until an error is noticed.

Figure 36B:
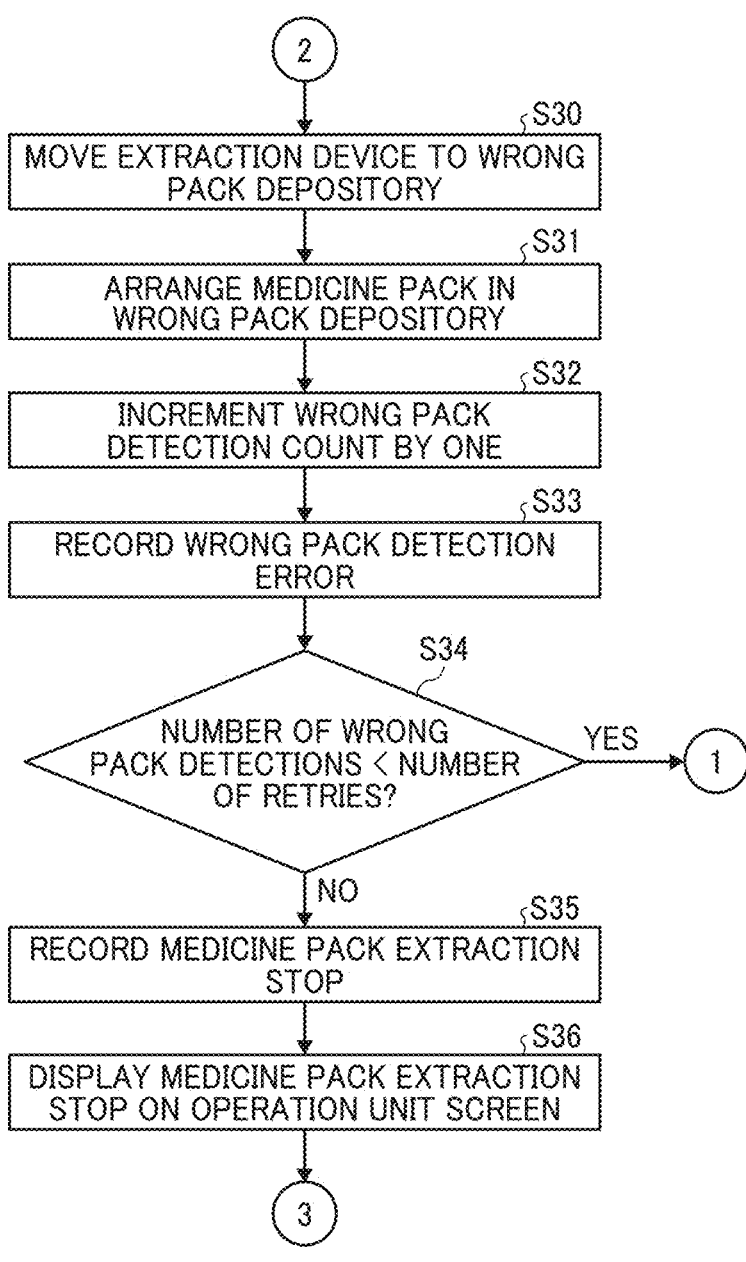

With reference to FIG. 36, a main operation flow from the processing of extracting a pack to the processing of delivering the extracted pack to the medicine delivery tray will be described. FIG. 36 including FIGS. 36A and 36B illustrates a main flowchart from the processing of extracting a pack to the processing of arranging the extracted pack in the medicine delivery tray.

The flow of FIG. 36 starts from step S20 in which the number of erroneous packs detections is initialized (the number of erroneous pack detection=0). Then, as illustrated in FIG. 12A, the extraction device 50 is moved to the designated storage 10 (step S21). As illustrated in FIGS. 12B to 12E, the pack 2 is extracted from the storage 10 by the extraction device 50 (step S22).

As illustrated in FIG. 13A, the first medication-related information of the extracted pack 2 is acquired by imaging with the camera 135 (step S23). The pack information management unit 140 (the controller 150) compares the first medication-related information of the pack 2 acquired by imaging with the camera 135 with the second medication-related information managed by the pack information management unit 140 (the controller 150) to determine whether there is a match between the first medication-related information and the second medication-related information match (step S24). That is, in step S24, when there is a match between the first medication-related information and the second medication-related information, no error occurs and processing can be normally performed. Thus, it is determined that "the medication-related information is correct: YES", and the extracted pack 2 is correct. Accordingly, as illustrated in FIG. 13B, the extraction device 50 holding the extracted correct pack 2 is moved to the designated medicine delivery tray (step S25). Then, as illustrated in FIGS. 13C, 13D, and 13E, the medicine delivery processing (insertion into a specific section in the medicine delivery tray 30) of the extracted correct pack 2 is performed (step S26).

Next, as illustrated in FIG. 14B, the medicine pack delivery detection sensors 137a to 137d acquire the medicine delivery processing result (whether the correct packs 2 extracted are inserted into specific sections in the medicine delivery tray 30) (step S27). Next, the processing proceeds to step S28. If the medicine delivery processing result is normal: YES, no error occurs and the processing can be performed normally. Thus, the extraction device 50 is moved to the home position (for example, the position illustrated in FIG. 12A) (step S29), and the processing is ended.

On the other hand, in step S24, as a result of the comparison between the first medication-related information of the pack 2 acquired through the imaging by the camera 135 and the second medication-related information managed by the pack information management unit 140 (the controller 150), if it is determined that there is no match between the first medication-related information and the second medication-related information (if the medication-related information is wrong), it is determined that "the medication-related information is correct: NO". Accordingly, the extraction device 50 is moved to the wrong pack depository 40 illustrated in FIGS. 1A and 1B (step S30). Then, an operation of arranging the wrong pack extracted by the extraction device 50 in the wrong pack depository 40 is performed (step S31).

The pack information management unit 140 (the controller 150) performs arithmetic processing of incrementing the count of the number of wrong pack detections by one (step S32). The count of the number of wrong pack detections is recorded in the memory 152 illustrated in FIG. 17 (step S33).

The processing proceeds to step S34. The pack information management unit 140 (the controller 150) compares the number of retries set in the system of the medication support apparatus 200 with the number of wrong pack detections. If "the number of wrong pack detection<the number of retries: YES", the processing returns to step S21. The extraction device 50 is moved again to the storage 10 to execute the extraction of the pack 2.

If "the number of wrong pack detections<the number of retries: NO", the extraction of the medicine pack is stopped. Then, the error is notified to the user by displaying on the operation unit screen of the touch panel 151 or by using the notification device 155 that the extraction of the medicine pack has been stopped.

In step S34, if "the number of wrong pack detections<the number of retries: NO", the process proceeds to step S35. The pack information management unit 140 (the controller 150) records the "pack extraction cancel error" in the memory 152. Further, the pack information management unit 140 (the controller 150) displays the cancellation of extraction of the pack 2 from the storage 10 on the operation unit screen of the touch panel 151 (step S36).

If the medication-related information is correct but the medicine delivery processing result is not normal (if the medicine delivery processing has failed) in step S28, an error has occurred and the processing cannot be performed normally. Therefore, the processing proceeds to step S37, and the pack information management unit 140 (the controller 150) records the "medicine delivery failure error" in the memory 152. The pack information management unit 140 (the controller 150) further displays the "medicine delivery failure error" on the operation unit screen of the touch panel 151 to notify the user of the error (step S38).

As described above, if no error occurs and processing can be performed normally, it is determined that "the medication-related information is correct: YES" (step S24) and "the medicine delivery processing result is normal: YES" (step S28), and the pack 2 extracted from the storage 10 is normally arranged in the section in the medicine delivery tray 30 without any trouble.

As described above, according to the medication support apparatus 200 and the medication support system of the embodiment described with reference to FIGS. 1A to 36, it is possible to prevent improper use of medicine (including erroneous medicine taking and forgetting to take medicine) by checking whether there is a match between the medicine pack before being transferred to the specific position in the medicine delivery part and the specific medicine pack to be arranged at the specific position in the medicine delivery part.

First Modification

Figures 37A, 37B:
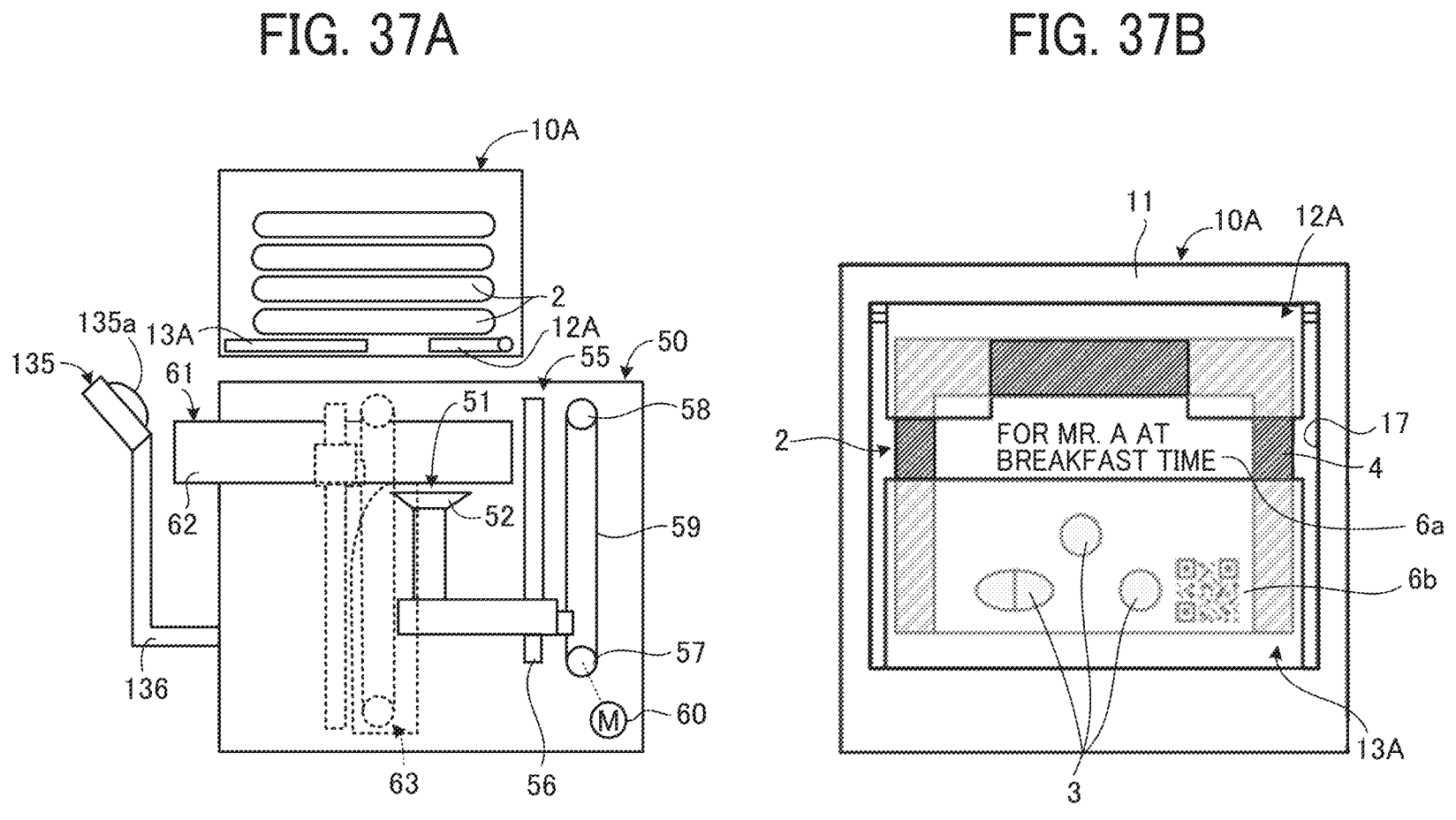

A first modification of the above embodiment will be described with reference to FIGS. 37A and 37B. FIG. 37A is a front view illustrating a configuration of a storage and an extraction device according to the first modification, and FIG. 37B is an enlarged bottom view of a lowermost pack stored in the storage according to the first modification.

The first modification is different from the storage 10 and the extraction device 50 illustrated in FIGS. 2A, 2B, 11A, 11B, and the like, mainly in that a storage 10A is used instead of the storage 10 and that the orientation of a camera 135 that is a pack information reader is changed.

The storage 10A is different from the storage 10, mainly in that at least one of a left supporter 12A and a right supporter 13A formed of transparent members is used, and that packs 2 to which first medication-related information is added are stacked in the storage 10A such that the bottom surface of the lowermost pack 2 is in contact with the left supporter 12A and the right supporter 13A.

The camera 135 is integrally installed on the extraction device 50 via a mounting bracket 136, and a lens 135a faces the lowermost portion of the storage 10A. Accordingly, the camera 135 can perform image capture and acquire at least the first medication-related information (medication-related information 6 a) of the pack 2 from the gap between the left supporter 12A and the right supporter 13A attached to the storage 10A.

Since at least one of the left supporter 12A and the right supporter 13A is formed of a transparent member, it is possible to capture an image of the first medication-related information (medication-related information 6a and 6b, the type of medicine 3, the number of tablets, and the like) on the surface of the lowermost pack 2 stacked in layers at the lowermost portion of the storage 10A and acquire the first medication-related information.

As described above, in the first modification, the first medication-related information of the pack 2 can be read by the camera 135 in a state where the pack 2 is stored in the storage 10A. Then, the first medication-related information of the pack 2 read by the camera 135 can be compared with second medication-related information managed by a pack information management unit 140.

According to the first modification, if there is no match between the first and second medication-related information, it is possible to prevent a wrong pack from being extracted from the storage. This eliminates the need for wrong pack processing, thereby improving productivity in the completion of the medicine delivery tray.

Second Modification

Figure 38:
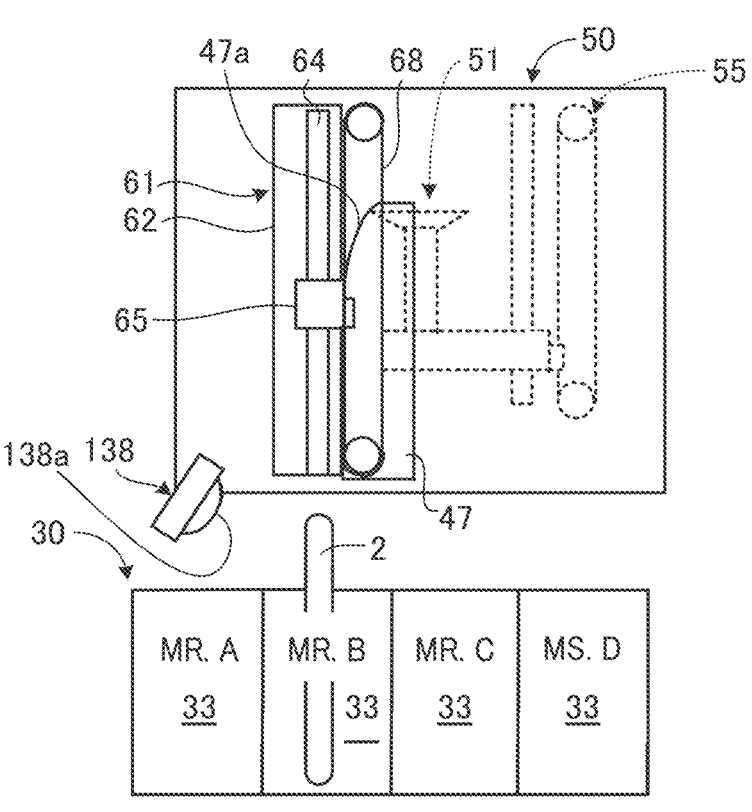
FIG. 38 is a front view illustrating a configuration of an extraction device according to a second modification.

A second modification of the above embodiment will be described with reference to FIG. 38. FIG. 38 is a front view illustrating a configuration of an extraction device according to the second modification.

The second modification is different mainly in that a camera 138 is used instead of the medicine pack delivery detection sensors 137a to 137d including the optical sensors illustrated in FIGS. 14A and 14B. The camera 138 is different from the camera 135 (not illustrated in FIG. 38) as the pack information reader illustrated in FIGS. 11A, 11B, and the like. The camera 138 has a function of a medicine pack delivery detector that detects that the pack 2 is arranged at a specific position (section) in the medicine delivery tray 30 (medicine delivery processing result).

The camera 138 is attached to an extraction device 50 with a mounting bracket (not illustrated) such that a lens 138a faces in a direction in which sections in the medicine delivery tray 30 can be imaged, and determines whether the medicine delivery processing is normal from images captured before and after the medicine delivery processing. That is, the camera 138 is formed as a part of the extraction device 50.

In order to detect that the pack 2 is arranged at a specific position (section) in the medicine delivery tray 30, the medicine pack delivery detector has to be moved to the vicinity of the specific position (section) in the medicine delivery tray 30. However, the entire structure of the apparatus can be simplified by using the camera 138 as the medicine pack delivery detector as a part of the extraction device 50, that is, by using the camera 138 also as a drive mechanism of the extraction device 50. In other words, there is no need for a plurality of drive mechanisms similar to the drive mechanism of the extraction device 50 in order to detect that the pack 2 is arranged at a specific position (section) in the medicine delivery tray 30.

As illustrated in FIGS. 14A and 14B, in the case of using an optical sensor (medicine pack delivery detector) to detect that the pack 2 is arranged at a specific position (section) in the medicine delivery tray 30 (medicine delivery processing result), the optical sensor has to be provided for each section.

If the optical sensor is installed for each section in the medicine delivery tray 30, the number of sensors and harnesses (cables) to the sensors become enormous. On the contrary, it is possible to avoid complication due to the sensors and the harnesses by providing the camera 138 as a means for detecting the medicine delivery result of the pack on the extraction device 50 as illustrated in FIG. 38.

The camera 138 used in the second modification has been described as being different from the camera 135 as the pack information reader illustrated in FIGS. 11A, 11B, and the like. However, the camera 138 is not limited to this configuration. That is, focusing on the fact that the image capture timings of the camera 135 and the camera 138 are different, the camera 135 as the pack information reader can also be used as the medicine pack delivery detector and can be structured to be movable in the extraction device 50, so that the camera 135 alone may be provided in the apparatus.

It can be said that the following aspects and advantageous effects are substantially described in the above embodiments, modifications, and the like.

A first aspect is a medication support apparatus including: a storage such as the storages 10 and 10A configured to store a medicine pack such as a medicine pack 2 to which first medication-related information is added and in which medicine such as medicine 3 is packaged; a medicine delivery part such as a medicine delivery tray 30 configured to arrange the specific medicine pack at a specific position; an extraction device such as an extraction device 50 configured to extract the specific medicine pack from the storage; a transfer device such as a transfer device 90 configured to transfer the medicine pack extracted from the storage to a specific position in the medicine delivery part; a pack information reader such as a camera 135 configured to read the first medication-related information before transferring the medicine pack extracted from the storage to the specific position in the medicine delivery part; and a pack information management unit such as a pack information management unit 140 configured to manage second medication-related information of the specific medicine pack to be arranged at the specific position in the medicine delivery part, wherein the pack information management unit compares the first medication-related information read by the pack information reader with the second medication-related information to determine whether there is a match between both of the medication-related information.

With such a configuration, according to the first aspect, it is possible to prevent improper use of medicine (including erroneous medicine taking and forgetting to take medicine) by checking whether there is a match between the medicine pack before being transferred to the specific position in the medicine delivery part and the specific medicine pack to be arranged at the specific position in the medicine delivery part.

According to a second aspect, in the medication support apparatus in the first aspect, as a result of the comparison between the first medication-related information and the second medication-related information, when there is a match between the first medication-related information and the second medication-related information, the pack information management unit causes the extraction device and the transfer device to transfer and arrange the medicine pack to the medicine delivery part, and when there is no match between the first medication-related information and the second medication-related information, the pack information management unit determines that the medicine pack extracted from the storage is a wrong pack and causes the extraction device and the transfer device to transfer the medicine pack to a wrong pack depository such as the wrong pack depository 40 configured to store the wrong pack.

With such a configuration, according to the second aspect, since the method for processing the wrong pack is clarified, it is possible to continue the process of preparing the medicine delivery part excluding the step with the wrong pack. In other words, moving the wrong pack to the dedicated wrong pack depository makes it possible to prevent the medicine in the wrong pack from being used for medication.

According to a third aspect, the medication support apparatus in the first or second aspect includes: a medicine pack delivery detector such as medicine pack detection sensors 137a to 137d configured to detect that the medicine pack is arranged at a specific position in the medicine delivery part; and a medicine delivery information management unit such as a medicine delivery information management unit 145 configured to manage position information of the medicine pack extracted from the storage, in the medicine delivery part, wherein the medicine delivery information management unit determines that the medicine pack is arranged at the specific position in the medicine delivery part, based on a result of detection by the medicine pack delivery detector.

With such a configuration, according to the third aspect, the medicine delivery information management unit determines that the medicine pack actually extracted from the storage is arranged at a specific position in the medicine delivery part based on the result of detection by the medicine pack delivery detector, whereby it is possible to prevent improper use of medicine.

According to a fourth aspect, in the medication support apparatus in the second aspect, after the medicine pack determined to be the wrong pack is transferred to the wrong pack depository, an extraction process is performed again by the extraction device of extracting the medicine pack from the storage in which the wrong pack has been stored, and a medicine delivery process is performed again by the transfer device of transferring the medicine pack extracted from the storage to a specific position in the medicine delivery part.

With such a configuration, according to the fourth aspect, when the wrong pack is mixed in the storage, after transferring the wrong pack to the wrong pack depository, the extraction processing and the medicine delivery processing are repeatedly executed to increase the possibility of completing the medicine delivery part.

According to a fifth aspect, the medication support apparatus in the third aspect further includes a determination result memory device such as the memory 152 configured to record a result of comparison between the first medication-related information and the second medication-related information or a result of detection by the medicine pack delivery detector, wherein detection information of the wrong pack or information indicating that the medicine delivery processing of the medicine pack to the medicine delivery part has failed is recorded in the determination result memory device so as to be able to be checked later.

With such a configuration, according to the fifth aspect, the correctness of the medicine pack and the success or failure of the medicine delivery processing can be left as evidence.

According to a sixth aspect, the medication support apparatus in the fourth aspect further include a notification device configured to issue a warning to a user, wherein when it is determined that the medicine pack extracted by executing again the extraction of the medicine pack from the storage in which the wrong pack has been stored is the wrong pack again, the extraction of the medicine pack from the storage in which the wrong pack has been stored is stopped, and the notification device issues the warning to the user.

With such a configuration, according to the sixth aspect, issuing the warning to the user allows the user to check the medicine pack stored in the storage.

According to a seventh aspect, in the medication support apparatus in any one of the first to sixth aspects, the pack information reader is configured as a part of the extraction device.

With such a configuration, according to the seventh aspect, it is necessary to move the pack information reader to the storage in order to read the first medication-related information. However, the configuration of the entire device can be simplified by using the pack information reader as a part of the extraction device, that is, by using the pack information reader also as a drive mechanism of the extraction device. In other words, it is not necessary to have a plurality of drive mechanisms similar to the drive mechanism of the extraction device for reading the first medication-related information by the pack information reader.

According to an eighth aspect, in the medication support apparatus in the third aspect, the medicine pack delivery detector is configured as a part of the extraction device.

With such a configuration, according to the eighth aspect, it is necessary to move the medicine pack delivery detector to the vicinity of the specific position of the medicine delivery part in order to detect that the medicine pack is disposed at the specific position of the medicine delivery part, but the configuration of the entire device can be simplified by using the medicine pack delivery detector as a part of the extraction device, that is, by using the medicine pack delivery detector also as the drive mechanism of the extraction device. In other words, it is not necessary to provide a plurality of drive mechanisms similar to the drive mechanism of the extraction device in order to detect that the medicine pack is disposed at a specific position of the medicine delivery part by the medicine pack delivery detector.

According to a ninth aspect, in the medication support apparatus in any one of the first to eighth aspects, in a state where the medicine pack is stored in the storage, the pack information reader reads the first medication-related information and the pack information management unit performs the comparison.

With such a configuration, according to the ninth aspect, in a case where there is no match between the first and second medication-related information, the medicine pack is not extracted from the storage means, so that the processing of the wrong pack is unnecessary, and productivity in the completion of the medicine delivery part can be improved.

According to a tenth aspect, in the medication support apparatus in any one of the first to ninth aspects, the medication-related information is a name of a recipient who is to take the medicine in the medicine pack.

With such a configuration, according to the tenth aspect, it is possible to allow the corresponding recipient to take the medicine in the medicine pack prescribed.

According to an eleventh aspect, in the medication support apparatus in any one of the first to tenth aspects, the medication-related information is a time to take the medicine in the medicine pack.

With such a configuration, according to the eleventh aspect, it is possible to allow the corresponding recipient to take the medicine in the medicine pack at the prescribed timing.

According to a twelfth aspect, in the medication support apparatus in any one of the first to eleventh aspects, the medication-related information is a type and number of tablets of the medicine prescribed in the medicine pack.

With this configuration, according to the twelfth aspect, it is possible to detect an error in the medicine and the number of tablets in the medicine pack by checking the information on the medicine and the number of tablets prescribed in the medicine pack, so that it is possible to allow the recipient to correctly take the prescribed number of tablets in the medicine.

A thirteenth aspect is a medication support system including an information communication unit capable of performing communication via a network in the medication support apparatus in any one of the first to twelfth aspects, wherein at least one of detection information indicating that the medicine pack extracted from the storage is a wrong pack and information indicating that medicine delivery processing of the medicine pack to the medicine delivery part has failed is transmitted to an information communication terminal owned by a system user.

With such a configuration, according to the thirteen aspect, the details of error information at the time of preparing the medicine delivery part (for example, a medicine delivery table or a medicine delivery tray) can be acquired at any time so that it is possible to save recovery work time and unnecessary time until an error is noticed.

The above-described embodiments are illustrative and do not limit the present disclosure. Thus, numerous additional variations are possible in light of the above teachings. For example, elements and features of different illustrative embodiments may be combined with each other and substituted for each other within the scope of the present disclosure. For example, the technical matters described in the above embodiments and modifications may be combined as appropriate.

The effects appropriately described in the above-described embodiments and examples of the present disclosure are merely listing examples of the effects obtained from embodiments of the present disclosure, and the effects according to the present disclosure are not limited to those described in the embodiments and examples of the present disclosure.

The above-described embodiments are illustrative and do not limit the present invention. Thus, numerous additional modifications and variations are possible in light of the above teachings. For example, elements and/or features of different illustrative embodiments may be combined with each other and/or substituted for each other within the scope of the present invention.

Any one of the above-described operations may be performed in various other ways, for example, in an order different from the one described above.

Each of the functions of the described embodiments may be implemented by one or more processing circuits or circuitry. Processing circuitry includes a programmed processor, as a processor includes circuitry. A processing circuit also includes devices such as an application specific integrated circuit (ASIC), digital signal processor (DSP), field programmable gate array (FPGA), and conventional circuit components arranged to perform the recited functions.

The invention claimed is:

1. A medication support apparatus, comprising:
a storage configured to store a medicine pack with first medication-related information, the stored medicine pack including medicine, the first medication-related information indicating at least a name of a recipient who is to take the medicine in the stored medicine pack, a type and number of tablets of the medicine prescribed in the stored medicine pack, and a timing of medication of the medicine in the stored medicine pack;
a medicine delivery part in which the stored medicine pack is to be arranged at a specific position;
an extraction device configured to extract the stored medicine pack from the storage;
a transfer device configured to transfer the extracted medicine pack from the storage to the specific position in the medicine delivery part;
a pack information reader configured to read the first medication-related information by capturing an image of the extracted medicine pack before the transfer device transfers the extracted medicine pack from the storage to the specific position in the medicine delivery part; and
processing circuitry configured to:

manage second medication-related information of the medicine pack to be arranged at the specific position in the medicine delivery part, the second medication-related information indicating at least a name of a recipient who is to take medicine in the medicine pack to be arranged at the specific position in the medicine delivery part, a type and number of tablets of the medicine prescribed in the medicine pack to be arranged at the specific position in the medicine delivery part, and a timing of medication to be arranged at the specific position in the medicine delivery part; and
compare the first medication-related information read by the pack information reader with the second medication-related information to determine whether the first medication-related information matches the second medication-related information.

2. The medication support apparatus according to claim 1, further comprising:
a wrong pack depository configured to store at least one wrong pack,
wherein the processing circuitry is configured to:
in response to the first medication-related information matching the second medication-related information, cause the extraction device and the transfer device to transfer and arrange the medicine pack to the medicine delivery part; and
in response to the first medication-related information not matching the second medication-related information, determine that the extracted medicine pack from the storage is the wrong pack and cause the extraction device and the transfer device to transfer the medicine pack to the wrong pack depository.

3. The medication support apparatus according to claim 2, wherein the processing circuitry is configured to:
in response to the medicine pack determined to be the wrong pack being transferred to the wrong pack depository, cause the extraction device and the transfer device to extract another medicine pack from the storage, and transfer the another medicine pack to the specific position in the medicine delivery part.

4. The medication support apparatus according to claim 3, further comprising:
a notification device configured to issue an alert to a user, wherein the processing circuitry is configured to cause the notification device to:
in response to determining that the another medicine pack extracted from the storage is the wrong pack,
cause the extraction device to stop extraction of still another medicine pack from the storage; and
cause the notification device to issue the alert to the user.

5. The medication support apparatus according to claim 1, further comprising:
a medicine pack delivery detector configured to detect that the medicine pack is arranged at the specific position in the medicine delivery part,
wherein the processing circuitry is configured to,
manage position information of the extracted medicine pack from the storage, in the medicine delivery part, and
determine whether the medicine pack is arranged at the specific position in the medicine delivery part based on a result of detection by the medicine pack delivery detector.

6. The medication support apparatus according to claim 5, further comprising:

a memory configured to record a comparison result between the first medication-related information and the second medication-related information or a detection result by the medicine pack delivery detector, wherein the processing circuitry is configured to record, in the memory, detection information of a wrong pack or information indicating that medicine delivery processing of the medicine pack to the medicine delivery part has failed, to allow the detection information or the information to be checked later.

7. The medication support apparatus according to claim 5, wherein the medicine pack delivery detector is part of the extraction device.

8. The medication support apparatus according to claim 5, wherein the medicine pack delivery detector is configured to read the second medication-related information from the medicine pack to be arranged at the specific position in the medicine delivery part using a second camera.

9. The medication support apparatus according to claim 1, wherein the pack information reader is part of the extraction device.

10. The medication support apparatus according to claim 1, wherein in a state where the medicine pack is stored in the storage, the pack information reader is configured to read the first medication-related information, and the processing circuitry is configured to compare the first medication-related information read by the pack information reader with the second medication-related information.

11. The medication support apparatus according to claim 1, wherein the storage includes at least one transparent member on a bottom surface of the storage; and the pack information reader is configured to capture the image of the extracted medicine pack through the at least one transparent member.

12. A medication support system, comprising:

a medication support apparatus including, a storage configured to store a medicine pack with first medication-related information, the stored medicine pack including medicine, the first medication-related information indicating at least a name of a recipient who is to take the medicine in the stored medicine pack, a type and number of tablets of the medicine prescribed in the stored medicine pack, and a timing of medication of the medicine in the stored medicine pack, a medicine delivery part in which the stored medicine pack is to be arranged at a specific position, an extraction device configured to extract the stored medicine pack from the storage, a transfer device configured to transfer the extracted medicine pack from the storage to the specific position in the medicine delivery part, a pack information reader configured to read the first medication-related information by capturing an image of the extracted medicine pack before the transfer device transfers the extracted medicine pack from the storage to the specific position in the medicine delivery part, and processing circuitry configured to:

manage second medication-related information of the medicine pack to be arranged at the specific position in the medicine delivery part, the second medication-related information indicating at least a name of a recipient who is to take medicine in the medicine pack to be arranged at the specific position in the medicine delivery part, a type and number of tablets of the medicine prescribed in the medicine pack to be arranged at the specific position in the medicine delivery part, and a timing of medication to be arranged at the specific position in the medicine delivery part, and compare the first medication-related information read by the pack information reader with the second medication-related information to determine whether the first medication-related information matches the second medication-related information;

an information communication terminal; and an information communication device configured to perform communication between the medication support apparatus and the information communication terminal via a network, wherein the processing circuitry is configured to cause the information communication device to transmit at least one of detection information indicating that the extracted medicine pack from the storage is a wrong pack or information indicating that medicine delivery processing of the medicine pack to the medicine delivery part has failed, to the information communication terminal.

13. The medication support system according to claim 12, further comprising:

a wrong pack depository configured to store at least one wrong pack, wherein the processing circuitry is configured to:

in response to the first medication-related information matching the second medication-related information, cause the extraction device and the transfer device to transfer and arrange the medicine pack to the medicine delivery part; and in response to the first medication-related information not matching the second medication-related information, determine that the extracted medicine pack from the storage is the wrong pack and cause the extraction device and the transfer device to transfer the medicine pack to the wrong pack depository.

14. The medication support system according to claim 13, wherein the processing circuitry is configured to:

in response to the medicine pack determined to be the wrong pack being transferred to the wrong pack depository, cause the extraction device and the transfer device to extract another medicine pack from the storage, and transfer the another medicine pack to the specific position in the medicine delivery part.

15. The medication support system according to claim 14, further comprising:

a notification device configured to issue an alert to a user, wherein the processing circuitry is configured to cause the notification device to:

in response to determining that the another medicine pack extracted from the storage is the wrong pack, cause the extraction device to stop extraction of still another medicine pack from the storage; and cause the notification device to issue the alert to the user.

16. The medication support system according to claim 12, further comprising:

a medicine pack delivery detector configured to detect that the medicine pack is arranged at the specific position in the medicine delivery part, wherein the processing circuitry is configured to, manage position information of the extracted medicine pack from the storage, in the medicine delivery part, and determine whether the medicine pack is arranged at the specific position in the medicine delivery part based on a result of detection by the medicine pack delivery detector.

17. The medication support system according to claim 16, further comprising:

a memory configured to record a comparison result between the first medication-related information and the second medication-related information or a detection result by the medicine pack delivery detector, wherein the processing circuitry is configured to record, in the memory, detection information of the wrong pack or information indicating that medicine delivery processing of the medicine pack to the medicine delivery part has failed, to allow the detection information or the information to be checked later.

18. The medication support system according to claim 16, wherein the medicine pack delivery detector is part of the extraction device.

19. The medication support system according to claim 12, wherein the pack information reader is part of the extraction device.

20. The medication support system according to claim 12, wherein in a state where the medicine pack is stored in the storage, the pack information reader is configured to read the first medication-related information, and the processing circuitry is configured to compare the first medication-related information read by the pack information reader with the second medication-related information.

* * * * *